United States Patent
Desai et al.

(10) Patent No.: US 11,298,123 B2
(45) Date of Patent: Apr. 12, 2022

(54) SURGICAL END EFFECTORS

(71) Applicant: Covidien LP, Mansfield, MA (US)

(72) Inventors: Arpan Desai, Hamden, CT (US); Paul C. DiCesare, Easton, CT (US); Danial Ferreira, Woodbridge, CT (US); Brandon Michael Zalewski, Plymouth, CT (US)

(73) Assignee: COVIDIEN LP, Mansfield, MA (US)

( * ) Notice: Subject to any disclaimer, the term of this patent is extended or adjusted under 35 U.S.C. 154(b) by 896 days.

(21) Appl. No.: 15/678,160

(22) Filed: Aug. 16, 2017

(65) Prior Publication Data

US 2018/0110512 A1    Apr. 26, 2018

Related U.S. Application Data

(60) Provisional application No. 62/410,879, filed on Oct. 21, 2016.

(51) Int. Cl.
*A61B 17/04* (2006.01)
*A61B 17/06* (2006.01)
(Continued)

(52) U.S. Cl.
CPC ...... *A61B 17/0491* (2013.01); *A61B 17/0493* (2013.01); *A61B 17/06166* (2013.01);
(Continued)

(58) Field of Classification Search
CPC .......... A61B 17/0491; A61B 17/06166; A61B 17/0493; A61B 2017/3409;
(Continued)

(56) References Cited

U.S. PATENT DOCUMENTS 3,596,528 A    8/1971 Dittrich et al.
3,866,510 A    2/1975 Eibes et al.
(Continued)

FOREIGN PATENT DOCUMENTS

EP    0374088 A1    6/1990
JP    S60129041 A    7/1985
(Continued)

OTHER PUBLICATIONS

Misumi, Basic Elements of Automation Clever Mechanisms: Rotary-Linear Motion Conversion Mechanism Aug. 1, 2016, https://www.misumi-techcentral.com/tt/en/lca/2016/08/ (Year: 2016).*
(Continued)

*Primary Examiner* — Elizabeth Houston
*Assistant Examiner* — Michael G Mendoza

(57) ABSTRACT

According to an aspect of the present disclosure, an end effector for use with a surgical device is provided. The end effector includes a drive assembly, a driver, a needle assembly, and a follower. The drive assembly includes a first helical groove. Rotation of the drive assembly in a first direction causes distal translation of the driver with respect to the drive assembly. The needle assembly is disposed in mechanical cooperation with the driver. Distal translation of the driver causes a corresponding distal translation of the needle assembly. The follower is configured to engage the first helical groove of the drive assembly. When the follower is engaged with the first helical groove, rotation of the drive assembly in the first direction causes distal translation of the follower with respect to the drive assembly.

19 Claims, 40 Drawing Sheets

(51) Int. Cl.
  *A61B 17/00* (2006.01)
  *A61B 17/34* (2006.01)
  *A61F 2/00* (2006.01)

(52) U.S. Cl.
  CPC . *A61B 17/0469* (2013.01); *A61B 2017/00367* (2013.01); *A61B 2017/00473* (2013.01); *A61B 2017/0472* (2013.01); *A61B 2017/06176* (2013.01); *A61B 2017/3409* (2013.01); *A61F 2/0063* (2013.01); *A61F 2002/0072* (2013.01)

(58) Field of Classification Search
  CPC .. A61B 2017/0472; A61B 2017/00473; A61B 2017/00367; A61B 17/0469; A61B 2017/06176; A61F 2002/0072; A61F 2/0063
  See application file for complete search history.

(56) References Cited

U.S. PATENT DOCUMENTS

| | | |
|---|---|---|
| 4,350,491 A | 9/1982 | Steuer |
| 4,708,147 A * | 11/1987 | Haaga ............... A61B 10/0266 600/566 |
| 4,730,726 A | 3/1988 | Holzwarth |
| 4,884,572 A | 12/1989 | Bays et al. |
| 4,926,218 A * | 5/1990 | Fukao ............... G03G 21/105 399/327 |
| 5,085,661 A | 2/1992 | Moss |
| 5,144,942 A | 9/1992 | Decarie et al. |
| 5,156,267 A | 10/1992 | Yates, Jr. et al. |
| 5,171,247 A | 12/1992 | Hughett et al. |
| 5,171,249 A | 12/1992 | Stefanchik et al. |
| 5,176,306 A | 1/1993 | Heimerl et al. |
| 5,207,697 A | 5/1993 | Carusillo et al. |
| 5,228,256 A | 7/1993 | Dreveny |
| 5,236,563 A | 8/1993 | Loh |
| 5,246,441 A | 9/1993 | Ross et al. |
| 5,246,450 A | 9/1993 | Thornton et al. |
| 5,249,583 A | 10/1993 | Mallaby |
| 5,312,023 A | 5/1994 | Green et al. |
| 5,330,487 A | 7/1994 | Thornton et al. |
| 5,344,061 A | 9/1994 | Crainich |
| 5,353,929 A | 10/1994 | Foster |
| 5,356,064 A | 10/1994 | Green et al. |
| 5,381,896 A | 1/1995 | Simons |
| 5,382,254 A | 1/1995 | McGarry et al. |
| 5,398,861 A | 3/1995 | Green |
| 5,403,327 A | 4/1995 | Thornton et al. |
| 5,407,070 A | 4/1995 | Bascos et al. |
| 5,433,721 A | 7/1995 | Hooven et al. |
| 5,439,468 A | 8/1995 | Schulze et al. |
| 5,466,243 A | 11/1995 | Schmieding et al. |
| 5,467,911 A | 11/1995 | Tsuruta et al. |
| 5,474,566 A | 12/1995 | Alesi et al. |
| 5,474,567 A | 12/1995 | Stefanchik et al. |
| 5,522,844 A | 6/1996 | Johnson |
| 5,527,319 A | 6/1996 | Green et al. |
| 5,553,765 A | 9/1996 | Knodel et al. |
| 5,562,685 A | 10/1996 | Mollenauer et al. |
| 5,564,615 A | 10/1996 | Bishop et al. |
| 5,582,615 A | 12/1996 | Foshee et al. |
| 5,582,616 A | 12/1996 | Bolduc et al. |
| 5,584,425 A | 12/1996 | Savage et al. |
| 5,588,581 A | 12/1996 | Conlon et al. |
| 5,601,571 A | 2/1997 | Moss |
| 5,601,573 A | 2/1997 | Fogelberg et al. |
| 5,607,436 A | 3/1997 | Pratt et al. |
| 5,626,613 A | 5/1997 | Schmieding |
| 5,628,752 A | 5/1997 | Asnis et al. |
| 5,649,931 A | 7/1997 | Bryant et al. |
| 5,662,662 A | 9/1997 | Bishop et al. |
| 5,681,330 A | 10/1997 | Hughett et al. |
| 5,683,401 A | 11/1997 | Schmieding et al. |
| 5,685,474 A | 11/1997 | Seeber |
| 5,697,935 A | 12/1997 | Moran et al. |
| 5,702,420 A | 12/1997 | Sterling et al. |
| 5,704,534 A | 1/1998 | Huitema et al. |
| 5,709,692 A | 1/1998 | Mollenauer et al. |
| 5,728,116 A | 3/1998 | Rosenman |
| 5,730,744 A | 3/1998 | Justin et al. |
| 5,732,806 A | 3/1998 | Foshee et al. |
| 5,735,854 A | 4/1998 | Caron et al. |
| 5,741,268 A | 4/1998 | Schutz |
| 5,762,255 A | 6/1998 | Chrisman et al. |
| 5,782,844 A | 7/1998 | Yoon et al. |
| 5,792,165 A | 8/1998 | Klieman et al. |
| 5,810,882 A | 9/1998 | Bolduc et al. |
| 5,824,008 A | 10/1998 | Bolduc et al. |
| 5,830,221 A | 11/1998 | Stein et al. |
| 5,843,087 A | 12/1998 | Jensen et al. |
| 5,897,564 A | 4/1999 | Schulze et al. |
| 5,904,693 A | 5/1999 | Dicesare et al. |
| 5,910,105 A | 6/1999 | Swain et al. |
| 5,911,722 A | 6/1999 | Adler et al. |
| 5,928,244 A | 7/1999 | Tovey et al. |
| 5,928,252 A | 7/1999 | Steadman et al. |
| 5,931,844 A | 8/1999 | Thompson et al. |
| 5,941,439 A | 8/1999 | Kammerer et al. |
| 5,954,259 A | 9/1999 | Viola et al. |
| 5,961,524 A | 10/1999 | Crombie |
| 5,964,772 A | 10/1999 | Bolduc et al. |
| 5,976,160 A | 11/1999 | Crainich |
| 5,997,552 A | 12/1999 | Person et al. |
| 6,010,513 A | 1/2000 | Tormala et al. |
| 6,013,991 A | 1/2000 | Philipp |
| 6,039,753 A | 3/2000 | Meislin |
| 6,074,395 A | 6/2000 | Trott et al. |
| 6,099,537 A | 8/2000 | Sugai et al. |
| 6,126,670 A | 10/2000 | Walker et al. |
| 6,132,435 A | 10/2000 | Young |
| 6,146,387 A | 11/2000 | Trott et al. |
| 6,183,479 B1 | 2/2001 | Tormala et al. |
| 6,228,098 B1 | 5/2001 | Kayan et al. |
| 6,235,058 B1 | 5/2001 | Huene |
| 6,241,736 B1 | 6/2001 | Sater et al. |
| 6,261,302 B1 | 7/2001 | Voegele et al. |
| 6,296,656 B1 | 10/2001 | Bolduc et al. |
| 6,330,964 B1 | 12/2001 | Kayan et al. |
| 6,387,113 B1 | 5/2002 | Hawkins et al. |
| 6,402,701 B1 * | 6/2002 | Kaplan ............... A61B 10/0233 600/567 |
| 6,402,757 B1 | 6/2002 | Moore, III et al. |
| 6,402,780 B2 | 6/2002 | Williamson, IV et al. |
| 6,425,900 B1 | 7/2002 | Knodel et al. |
| 6,439,446 B1 | 8/2002 | Perry et al. |
| 6,440,136 B1 | 8/2002 | Gambale et al. |
| 6,450,391 B1 | 9/2002 | Kayan et al. |
| 6,457,625 B1 | 10/2002 | Tormala et al. |
| 6,551,333 B2 | 4/2003 | Kuhns et al. |
| 6,562,051 B1 | 5/2003 | Bolduc et al. |
| 6,572,626 B1 | 6/2003 | Knodel et al. |
| 6,589,249 B2 | 7/2003 | Sater et al. |
| 6,592,593 B1 | 7/2003 | Parodi et al. |
| 6,626,916 B1 | 9/2003 | Yeung et al. |
| 6,632,228 B2 | 10/2003 | Fortier et al. |
| 6,652,538 B2 | 11/2003 | Kayan et al. |
| 6,663,656 B2 | 12/2003 | Schmieding et al. |
| 6,666,854 B1 | 12/2003 | Lange |
| 6,695,867 B2 | 2/2004 | Ginn et al. |
| 6,733,506 B1 | 5/2004 | McDevitt et al. |
| 6,743,240 B2 | 6/2004 | Smith et al. |
| 6,749,621 B2 | 6/2004 | Pantages et al. |
| 6,755,836 B1 | 6/2004 | Lewis |
| 6,773,438 B1 | 8/2004 | Knodel et al. |
| 6,800,081 B2 | 10/2004 | Parodi |
| 6,811,552 B2 | 11/2004 | Weil, Sr. et al. |
| 6,824,548 B2 | 11/2004 | Smith et al. |
| 6,837,893 B2 | 1/2005 | Miller |
| 6,840,943 B2 | 1/2005 | Kennefick et al. |
| 6,843,794 B2 | 1/2005 | Sixto, Jr. et al. |
| 6,869,435 B2 | 3/2005 | Blake, III |
| 6,884,248 B2 | 4/2005 | Bolduc et al. |
| 6,887,244 B1 | 5/2005 | Walker et al. |

(56) References Cited

U.S. PATENT DOCUMENTS

| | | |
|---|---|---|
| 6,893,446 B2 | 5/2005 | Sater et al. |
| 6,905,057 B2 | 6/2005 | Swayze et al. |
| 6,929,661 B2 | 8/2005 | Bolduc et al. |
| 6,942,674 B2 | 9/2005 | Belef et al. |
| 6,945,979 B2 | 9/2005 | Kortenbach et al. |
| 6,960,217 B2 | 11/2005 | Bolduc |
| 6,966,919 B2 | 11/2005 | Sixto, Jr. et al. |
| 6,988,650 B2 | 1/2006 | Schwemberger et al. |
| 7,000,819 B2 | 2/2006 | Swayze et al. |
| 7,070,601 B2 | 7/2006 | Culbert et al. |
| 7,122,028 B2 | 10/2006 | Looper et al. |
| 7,128,754 B2 | 10/2006 | Bolduc |
| 7,147,657 B2 | 12/2006 | Chiang et al. |
| 7,204,847 B1 | 4/2007 | Gambale |
| 7,261,716 B2 | 8/2007 | Strobel et al. |
| 7,357,287 B2 | 4/2008 | Shelton, IV et al. |
| 7,380,696 B2 | 6/2008 | Shelton, IV et al. |
| 7,404,508 B2 | 7/2008 | Smith et al. |
| 7,410,086 B2 | 8/2008 | Ortiz et al. |
| 7,434,717 B2 | 10/2008 | Shelton, IV et al. |
| 7,461,574 B2 | 12/2008 | Lewis et al. |
| 7,491,232 B2 | 2/2009 | Bolduc et al. |
| 7,544,198 B2 | 6/2009 | Parodi |
| 7,591,842 B2 | 9/2009 | Parodi |
| 7,611,521 B2 | 11/2009 | Lubbers et al. |
| 7,637,905 B2 | 12/2009 | Saadat et al. |
| 7,637,932 B2 | 12/2009 | Bolduc et al. |
| 7,670,362 B2 | 3/2010 | Zergiebel |
| 7,740,159 B2 | 6/2010 | Shelton, IV et al. |
| 7,758,612 B2 | 7/2010 | Shipp |
| 7,811,312 B2 | 10/2010 | Stevens et al. |
| 7,819,884 B2 | 10/2010 | Lee et al. |
| 7,823,267 B2 | 11/2010 | Bolduc |
| 7,828,838 B2 | 11/2010 | Bolduc et al. |
| 7,862,573 B2 | 1/2011 | Darois et al. |
| 7,867,252 B2 | 1/2011 | Criscuolo et al. |
| 7,905,890 B2 | 3/2011 | Whitfield et al. |
| 7,913,892 B2 | 3/2011 | Cole et al. |
| 7,922,061 B2 | 4/2011 | Shelton, IV et al. |
| 7,922,063 B2 | 4/2011 | Zemlok et al. |
| 7,931,660 B2 | 4/2011 | Aranyi et al. |
| 7,959,663 B2 | 6/2011 | Bolduc |
| 7,959,670 B2 | 6/2011 | Bolduc |
| 8,002,811 B2 | 8/2011 | Corradi et al. |
| 8,006,365 B2 | 8/2011 | Levin et al. |
| 8,034,076 B2 | 10/2011 | Criscuolo et al. |
| 8,062,306 B2 | 11/2011 | Nobis et al. |
| 8,075,570 B2 | 12/2011 | Bolduc et al. |
| 8,083,752 B2 | 12/2011 | Bolduc |
| 8,087,142 B2 | 1/2012 | Levin et al. |
| 8,092,519 B2 | 1/2012 | Bolduc |
| 8,114,099 B2 | 2/2012 | Shipp |
| 8,114,101 B2 | 2/2012 | Criscuolo et al. |
| 8,152,820 B2 | 4/2012 | Mohamed et al. |
| 8,181,840 B2 | 5/2012 | Milliman |
| 8,216,254 B2 | 7/2012 | McLean et al. |
| 8,216,272 B2 | 7/2012 | Shipp |
| 8,231,639 B2 | 7/2012 | Bolduc et al. |
| 8,282,670 B2 | 10/2012 | Shipp |
| 8,292,933 B2 | 10/2012 | Zergiebel |
| 8,323,314 B2 | 12/2012 | Blier |
| 8,328,823 B2 | 12/2012 | Aranyi et al. |
| 8,333,776 B2 | 12/2012 | Cheng et al. |
| 8,343,176 B2 | 1/2013 | Criscuolo et al. |
| 8,343,184 B2 | 1/2013 | Blier |
| 8,377,044 B2 | 2/2013 | Coe et al. |
| 8,382,773 B2 | 2/2013 | Whitfield et al. |
| 8,382,778 B2 | 2/2013 | Criscuolo et al. |
| 8,414,627 B2 | 4/2013 | Corradi et al. |
| 8,424,740 B2 | 4/2013 | Shelton, IV et al. |
| 8,465,520 B2 | 6/2013 | Blier |
| 8,474,679 B2 | 7/2013 | Felix |
| 8,579,919 B2 | 11/2013 | Bolduc et al. |
| 8,579,920 B2 | 11/2013 | Nering et al. |
| 8,597,311 B2 | 12/2013 | Criscuolo et al. |
| 8,603,135 B2 | 12/2013 | Mueller |
| 8,672,209 B2 | 3/2014 | Crainich |
| 8,684,247 B2 | 4/2014 | Scirica et al. |
| 8,685,044 B2 | 4/2014 | Bolduc et al. |
| 8,690,889 B2 | 4/2014 | Colesanti et al. |
| 8,690,897 B2 | 4/2014 | Bolduc |
| 8,728,098 B2 | 5/2014 | Daniel et al. |
| 8,728,099 B2 | 5/2014 | Cohn et al. |
| 8,728,102 B2 | 5/2014 | Criscuolo et al. |
| 8,728,120 B2 | 5/2014 | Blier |
| 8,777,969 B2 | 7/2014 | Kayan |
| 8,821,514 B2 | 9/2014 | Aranyi |
| 8,821,522 B2 | 9/2014 | Criscuolo et al. |
| 8,821,557 B2 | 9/2014 | Corradi et al. |
| 8,852,215 B2 | 10/2014 | Criscuolo et al. |
| 8,894,669 B2 | 11/2014 | Nering et al. |
| 8,920,439 B2 | 12/2014 | Cardinale et al. |
| 8,926,637 B2 | 1/2015 | Zergiebel |
| 9,017,345 B2 | 4/2015 | Taylor et al. |
| 9,023,065 B2 | 5/2015 | Bolduc et al. |
| 9,028,495 B2 | 5/2015 | Mueller et al. |
| 9,186,138 B2 | 11/2015 | Corradi et al. |
| 9,259,221 B2 | 2/2016 | Zergiebel |
| 9,282,961 B2 | 3/2016 | Whitman et al. |
| 9,332,983 B2 | 5/2016 | Shipp |
| 9,345,462 B2 | 5/2016 | Weitzner et al. |
| 9,351,728 B2 | 5/2016 | Sniffin et al. |
| 9,351,733 B2 | 5/2016 | Fischvogt |
| 9,358,004 B2 | 6/2016 | Sniffin et al. |
| 9,358,010 B2 | 6/2016 | Wenchell et al. |
| 9,364,231 B2 | 6/2016 | Wenchell |
| 9,364,274 B2 | 6/2016 | Zergiebel |
| 9,386,983 B2 | 7/2016 | Swensgard et al. |
| 9,402,623 B2 | 8/2016 | Kayan |
| 9,445,814 B2 | 9/2016 | Ranucci et al. |
| 9,486,218 B2 | 11/2016 | Criscuolo et al. |
| 9,526,498 B2 | 12/2016 | Reed |
| 9,615,830 B2 | 4/2017 | Ranucci et al. |
| 9,655,621 B2 | 5/2017 | Abuzaina et al. |
| 9,662,106 B2 | 5/2017 | Corradi et al. |
| 9,668,730 B2 | 6/2017 | Sniffin et al. |
| 9,783,329 B2 | 10/2017 | Sniffin et al. |
| 9,788,833 B2 | 10/2017 | Zergiebel et al. |
| 2003/0009441 A1 | 1/2003 | Holsten et al. |
| 2003/0208209 A1* | 11/2003 | Gambale ............ A61B 17/0625 606/144 |
| 2004/0015177 A1 | 1/2004 | Chu |
| 2004/0092937 A1 | 5/2004 | Criscuolo et al. |
| 2005/0222665 A1 | 10/2005 | Aranyi |
| 2006/0129152 A1 | 6/2006 | Shipp |
| 2007/0038220 A1 | 2/2007 | Shipp |
| 2007/0088390 A1 | 4/2007 | Paz et al. |
| 2007/0106317 A1 | 5/2007 | Shelton et al. |
| 2007/0162030 A1 | 7/2007 | Aranyi et al. |
| 2008/0097523 A1 | 4/2008 | Bolduc et al. |
| 2008/0312687 A1 | 12/2008 | Blier |
| 2009/0112234 A1 | 4/2009 | Crainich et al. |
| 2009/0118776 A1 | 5/2009 | Kelsch et al. |
| 2009/0131872 A1 | 5/2009 | Popov |
| 2009/0216154 A1 | 8/2009 | Lin Lee |
| 2010/0270354 A1 | 10/2010 | Rimer et al. |
| 2011/0022065 A1 | 1/2011 | Shipp |
| 2011/0295282 A1 | 12/2011 | Glick et al. |
| 2012/0059397 A1 | 3/2012 | Criscuolo et al. |
| 2012/0109157 A1 | 5/2012 | Criscuolo et al. |
| 2012/0323261 A1 | 12/2012 | Gaynor et al. |
| 2013/0116709 A1 | 5/2013 | Ziniti et al. |
| 2013/0325038 A1* | 12/2013 | Sato ...................... A61B 17/11 606/139 |
| 2014/0005678 A1 | 1/2014 | Shelton, IV et al. |
| 2014/0014707 A1 | 1/2014 | Onukuri et al. |
| 2014/0200587 A1 | 7/2014 | Pompee et al. |
| 2014/0243855 A1 | 8/2014 | Sholev et al. |
| 2014/0276967 A1 | 9/2014 | Fischvogt et al. |
| 2015/0032130 A1 | 1/2015 | Russo |
| 2015/0133970 A1 | 5/2015 | Ranucci et al. |
| 2015/0150558 A1 | 6/2015 | Zergiebel |
| 2015/0327859 A1 | 11/2015 | Bolduc |
| 2016/0007991 A1 | 1/2016 | Bolduc |

(56) References Cited

U.S. PATENT DOCUMENTS

| | | | |
|---|---|---|---|
| 2016/0007996 A1 | 1/2016 | Bolduc | |
| 2016/0045222 A1 | 2/2016 | Lee | |
| 2016/0074034 A1 | 3/2016 | Shipp | |
| 2016/0166255 A1 | 6/2016 | Fischvogt | |
| 2016/0249912 A1 | 9/2016 | Fischvogt | |
| 2016/0270778 A1 | 9/2016 | Zergiebel | |
| 2016/0270835 A1 | 9/2016 | Reed | |
| 2016/0278766 A1 | 9/2016 | Wenchell et al. | |
| 2016/0302824 A1* | 10/2016 | Sato | A61B 1/00 |
| 2016/0338694 A1 | 11/2016 | Kayan | |
| 2016/0345967 A1 | 12/2016 | Sniffin et al. | |

FOREIGN PATENT DOCUMENTS

| | | |
|---|---|---|
| JP | 09149906 | 6/1997 |
| WO | 93/16644 A1 | 9/1993 |
| WO | 03/037194 A1 | 5/2003 |

OTHER PUBLICATIONS

Thang010146, Barrel cam mechanism BT1a, Jan. 3, 2013, https://youtu.be/LLIwVdaRViM (Year 2013).*

Extended European Search Report corresponding to counterpart Patent Appln. EP 17 19 7477.7 dated Jul. 23, 2018.

Partial European Search Report corresponding to counterpart European Patent Appln. No. EP 17 19 7448.8 dated Jan. 12, 2018.

Extended European Search Report corresponding to EP 14 15 8946.5, completed Jun. 20, 2014 and dated Jul. 8, 2014; (9 pp).

Extended European Search Report corresponding to EP 14 17 8107.0, completed Nov. 24, 2014 and dated Dec. 3, 2014; (5 pp).

Extended European Search Report corresponding to EP 14 17 4656.0, completed Jan. 16, 2015 and dated Jan. 26, 2015; (7 pp).

Extended European Search Report corresponding to EP 14 18 4907.5, completed Jan. 12, 2015 and dated Jan. 27, 2015; (9 pp).

EP Search Report corresponding to EP 14 18 1900.3, completed Mar. 31, 2015 and dated Apr. 9, 2015; 7pp.

Extended European Search Report corresponding to counterpart application EP 14 19 7885.8 dated Apr. 30, 2015; 9pp.

Extended European Search Report corresponding to EP No. 11 25 0549.0, completed Sep. 9, 2013 and dated Sep. 17, 2013; 9 pages.

Extended European Search Report corresponding to EP 14 15 9394.7, completed Apr. 16, 2014 and dated Apr. 29, 2014; 8 pages.

European Search Report corresponding to EP No. 10 01 2659.8, completed Dec. 21, 2010; dated Jan. 3, 2011; 3 pages.

European Search Report corresponding to EP No. 10 01 2646.5, completed Feb. 11, 2011; dated Feb. 22, 2011.

Extended European Search Report corresponding to Int'l Application No. EP 14 15 1663.3 dated Jun. 7, 2016.

Supplementary European Search Report dated Feb. 2, 2017 in corresponding European Patent Application No. 14817036, 8 pages.

European Search Report dated May 10, 2017 in corresponding European Patent Application No. 17157259.7, 12 pages.

Extended European Search Report corresponding to counterpart European Patent Appln. No EP 17 19 7455.3 dated Jan. 17, 2018.

Extended European Search Report corresponding to counterpart EP Appln. No. 17 19 7448.8 dated May 15, 2018.

European Office Action dated Mar. 25, 2020 corresponding to counterpart Patent Application EP 17197448.8.

* cited by examiner

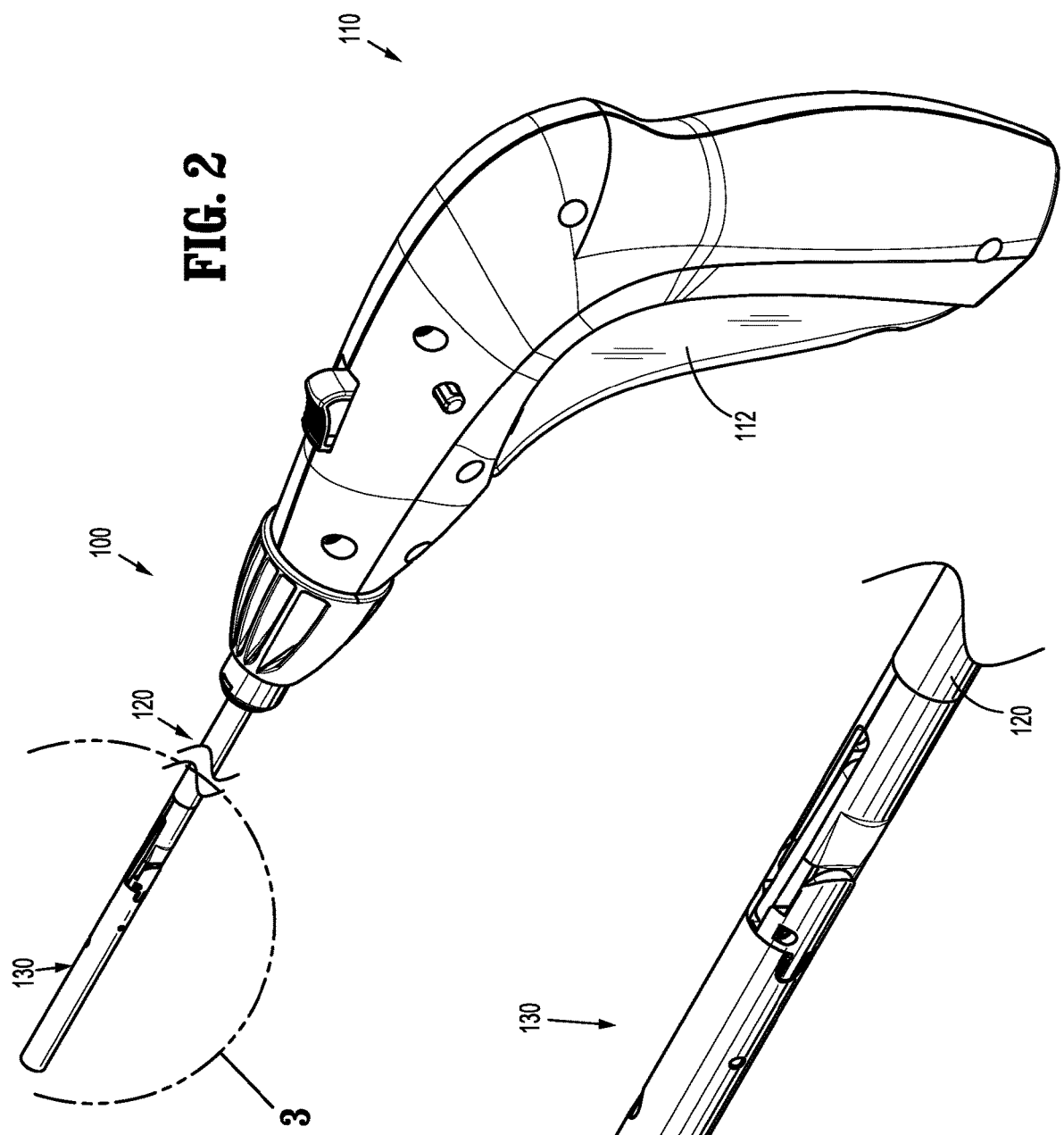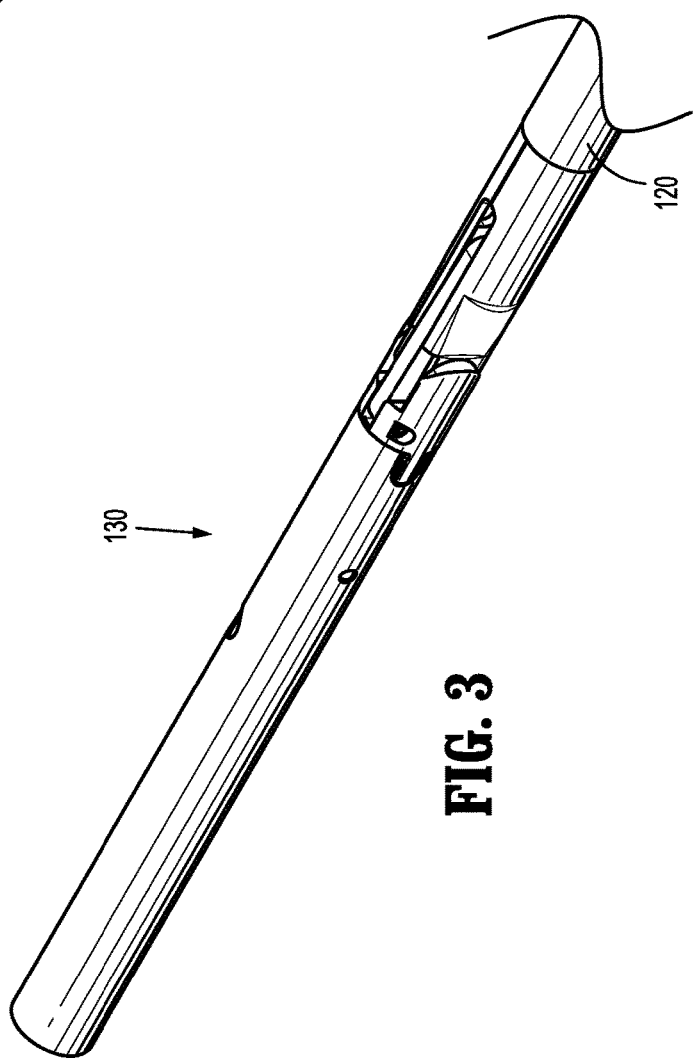

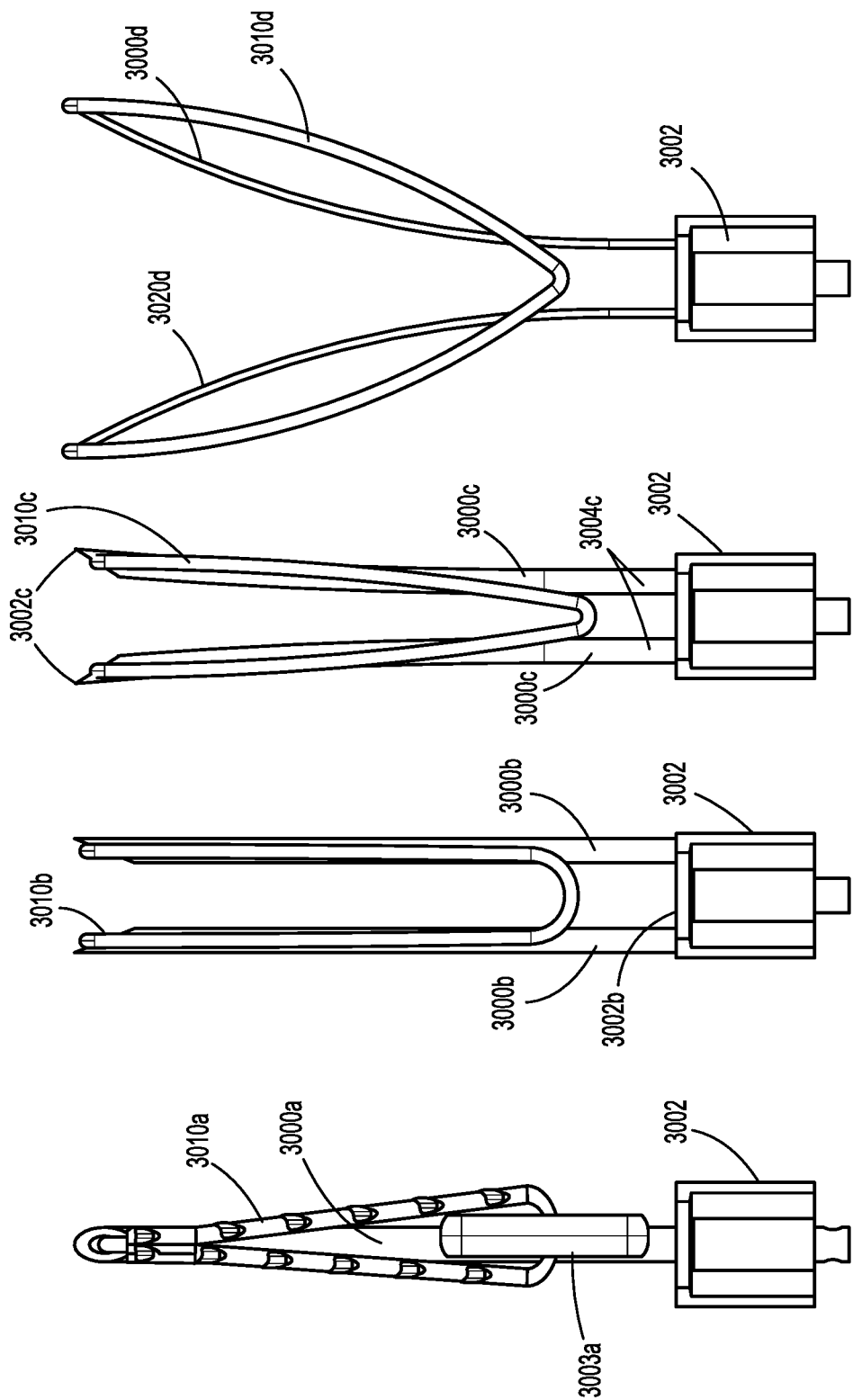

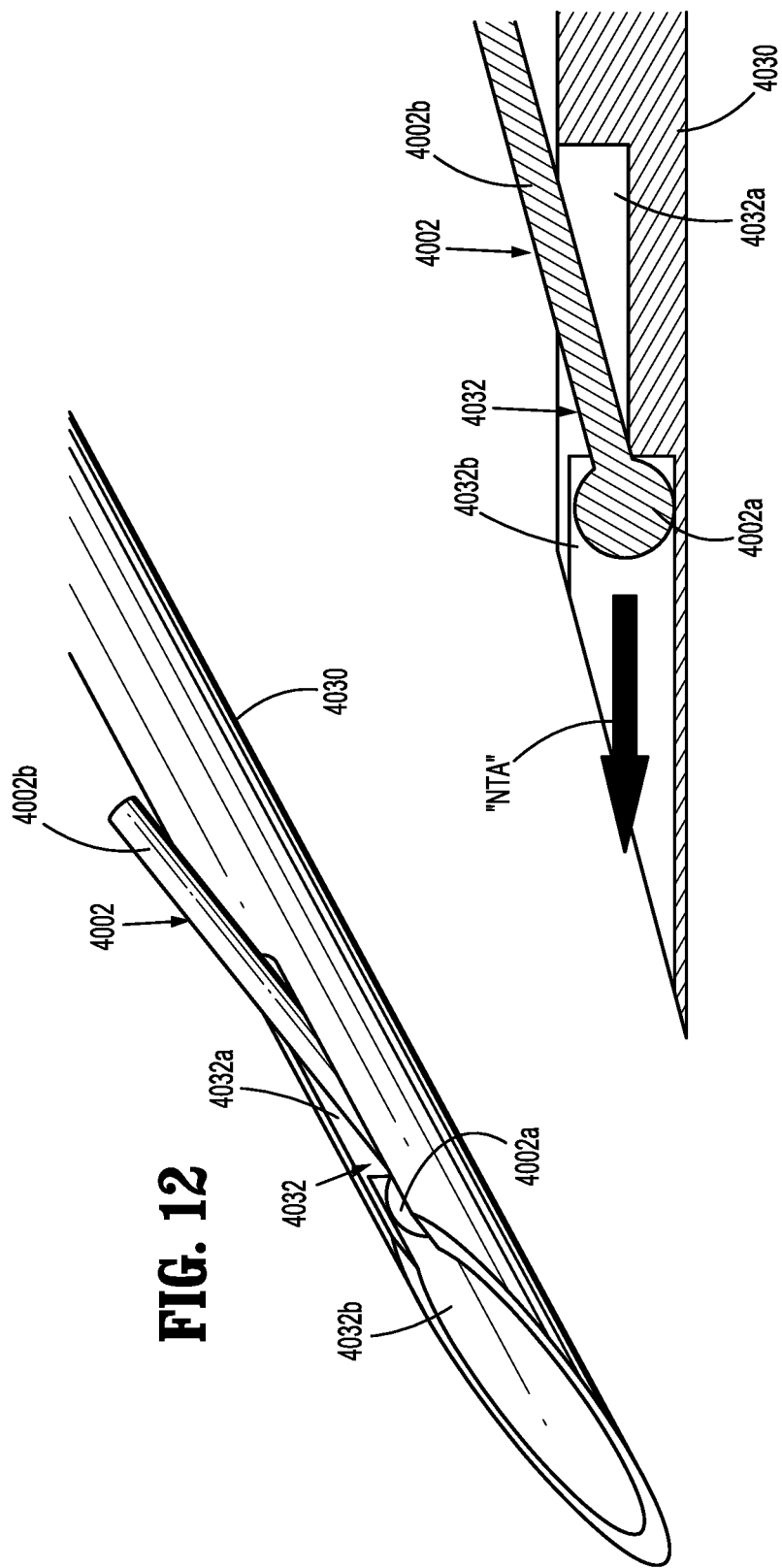

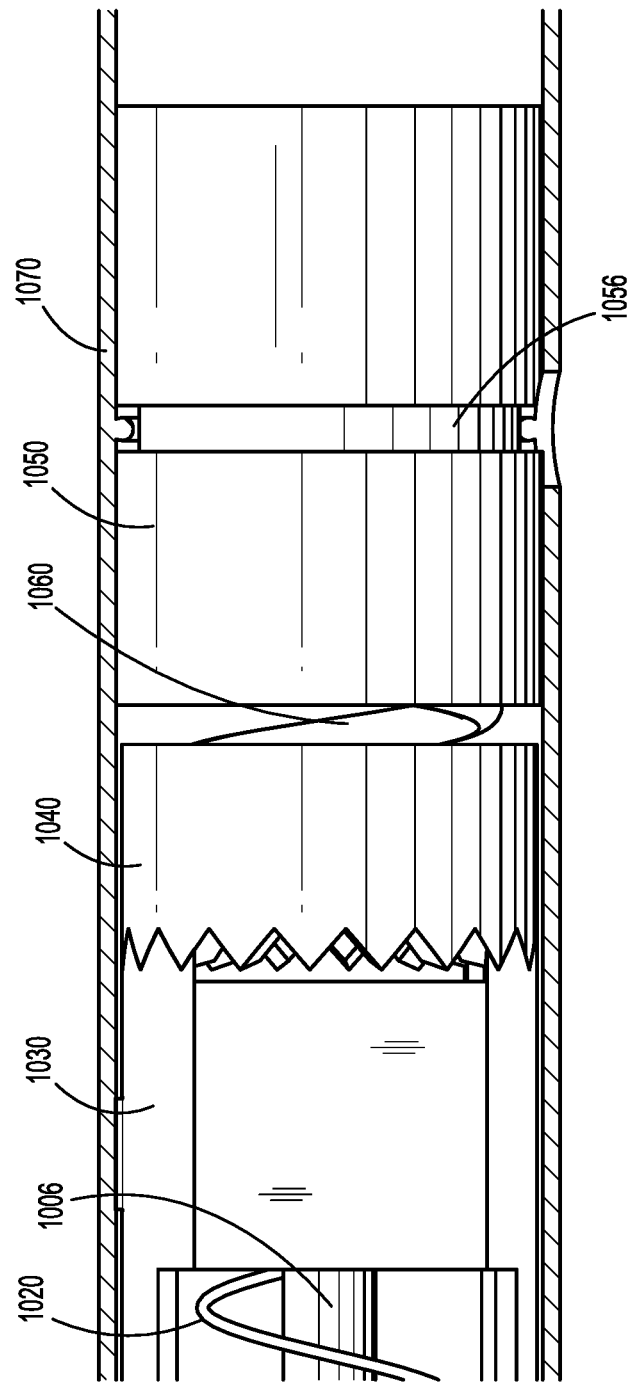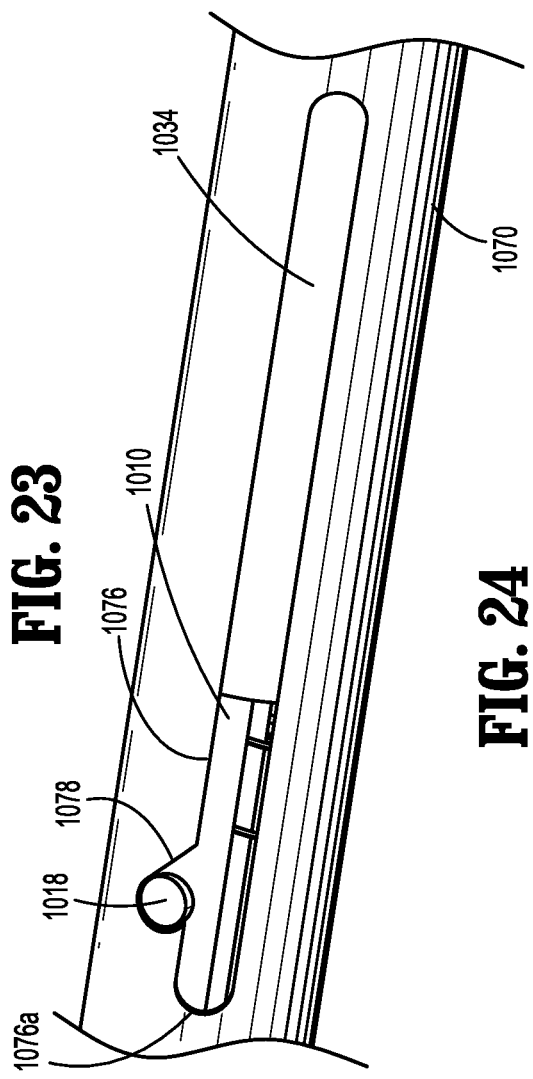

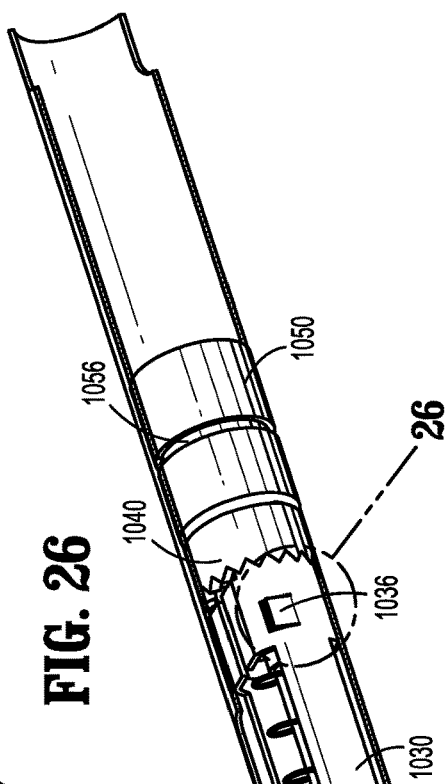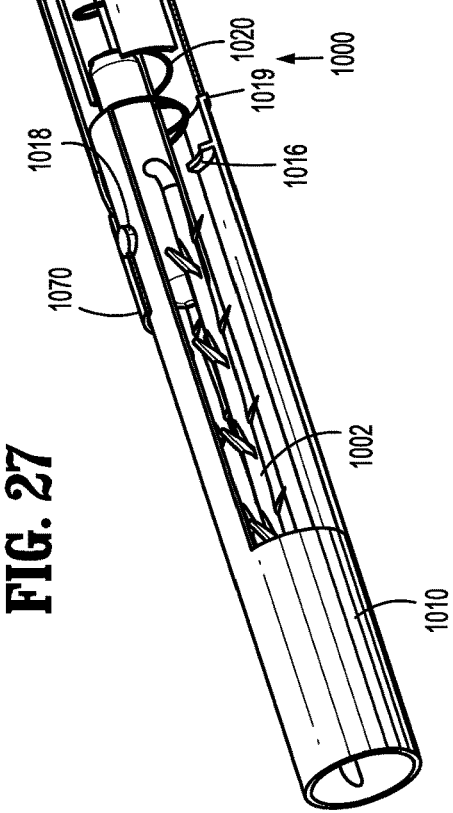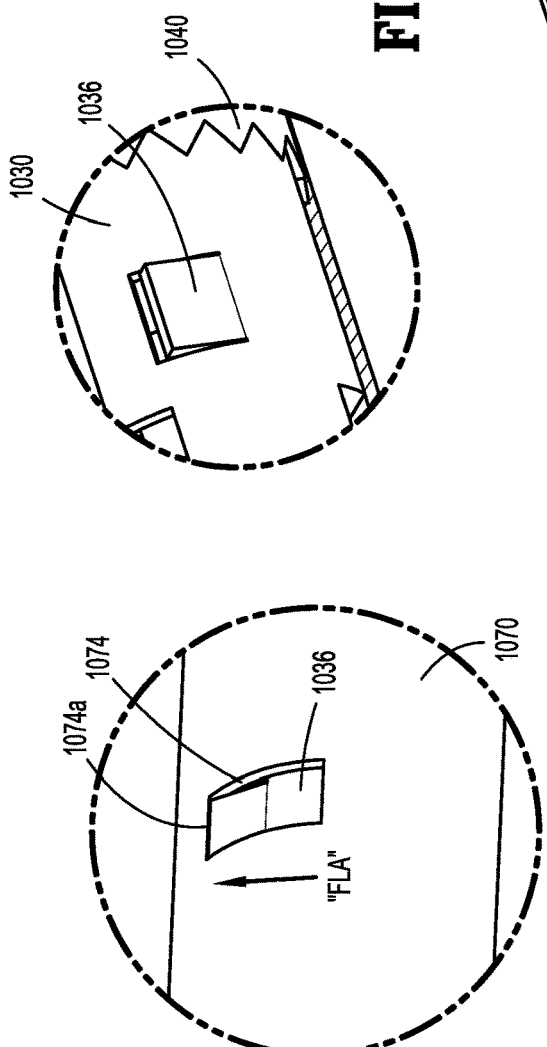

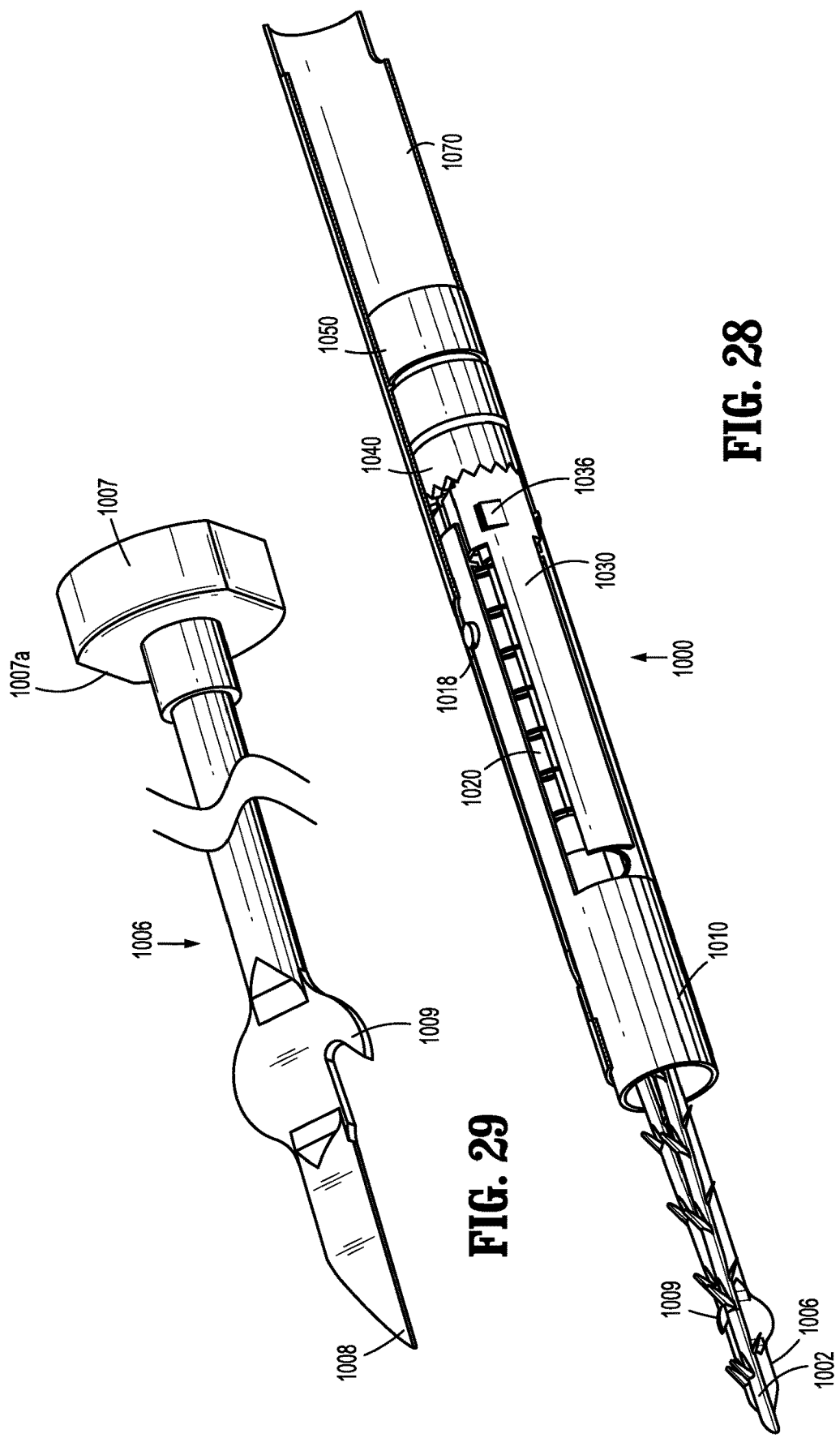

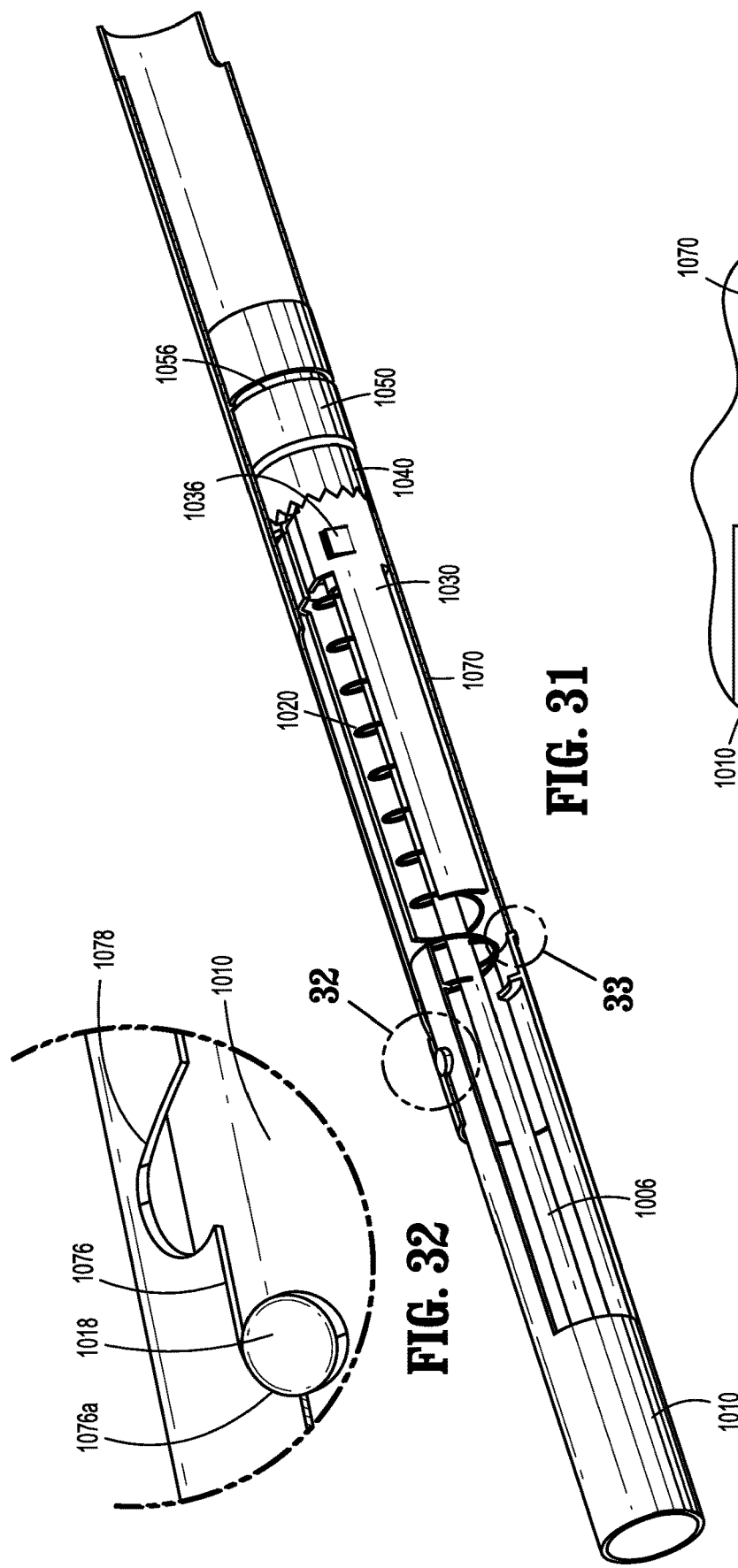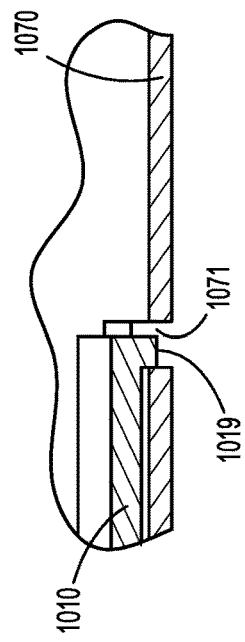

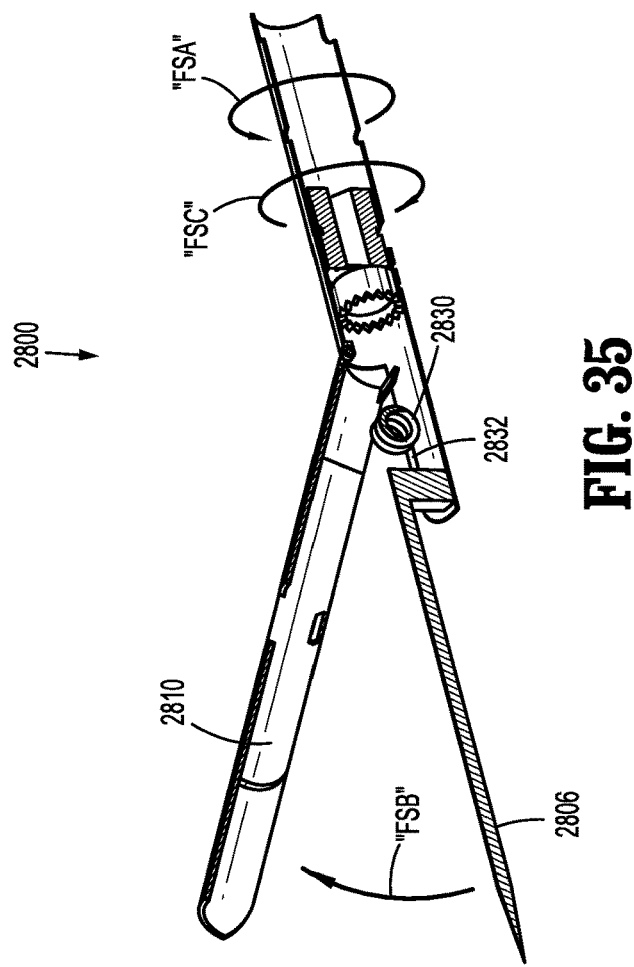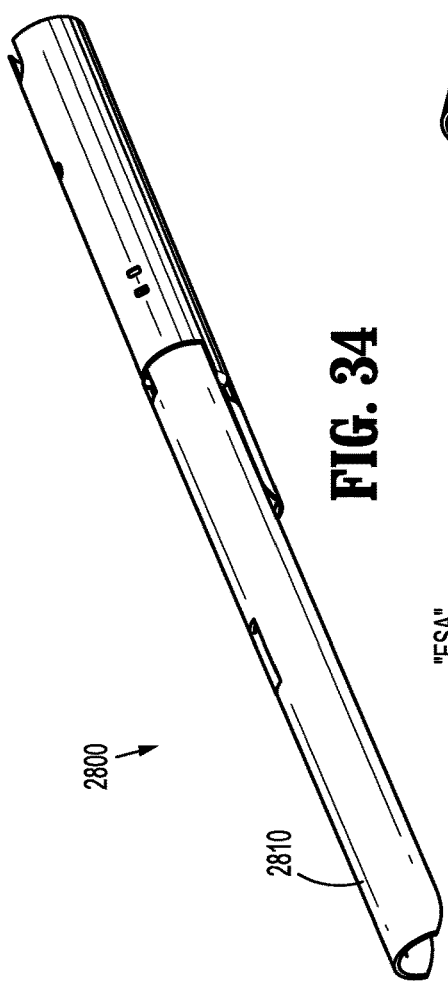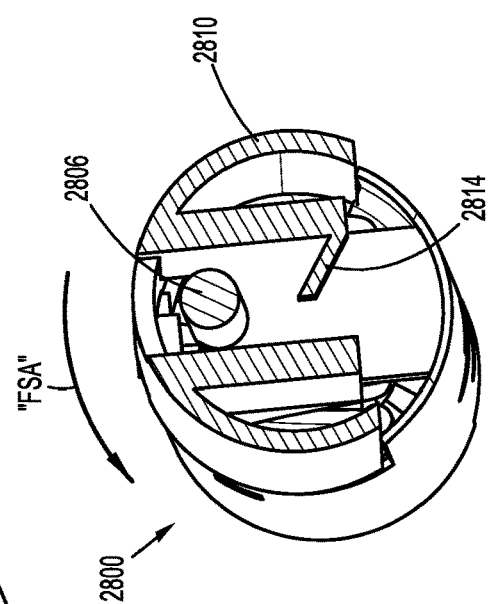

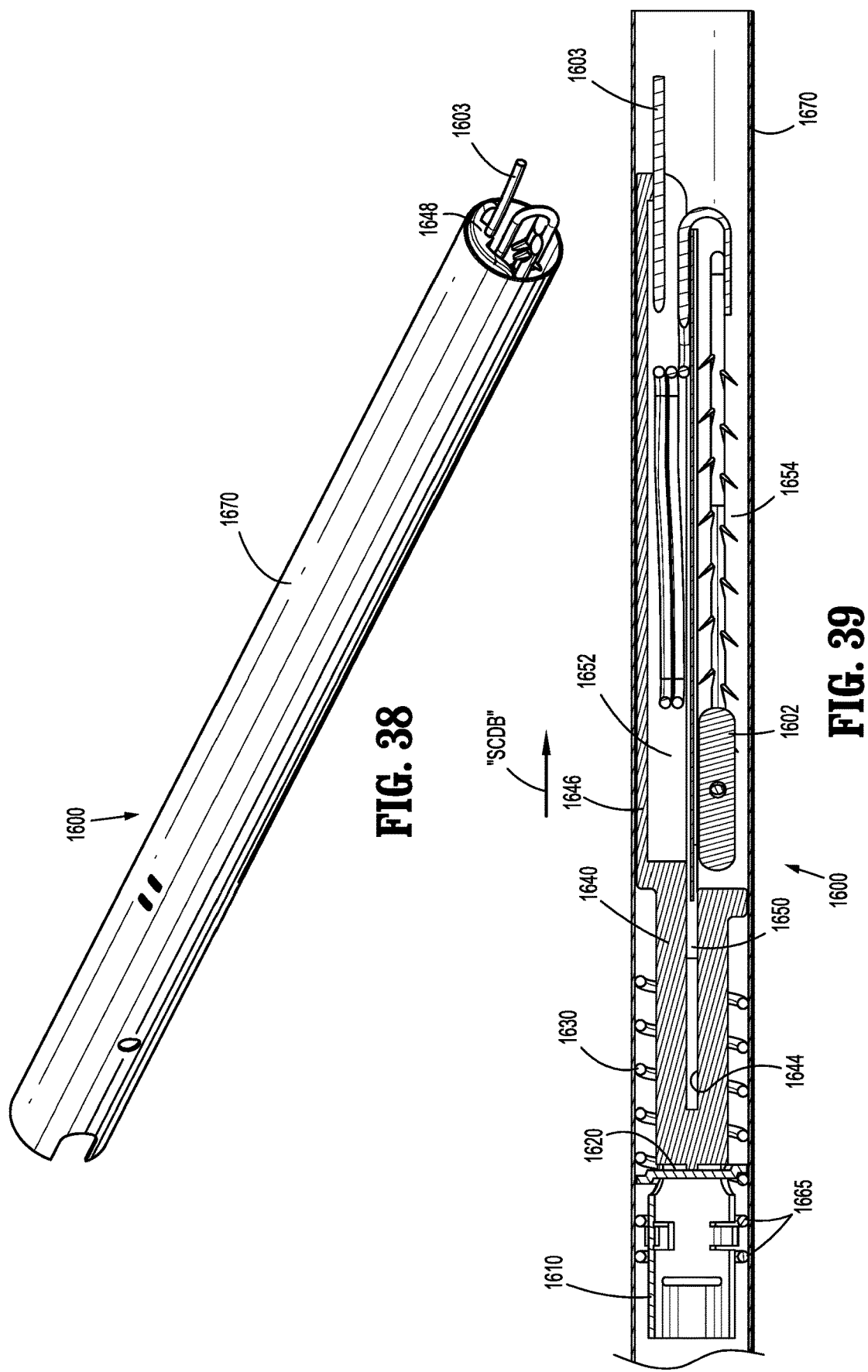

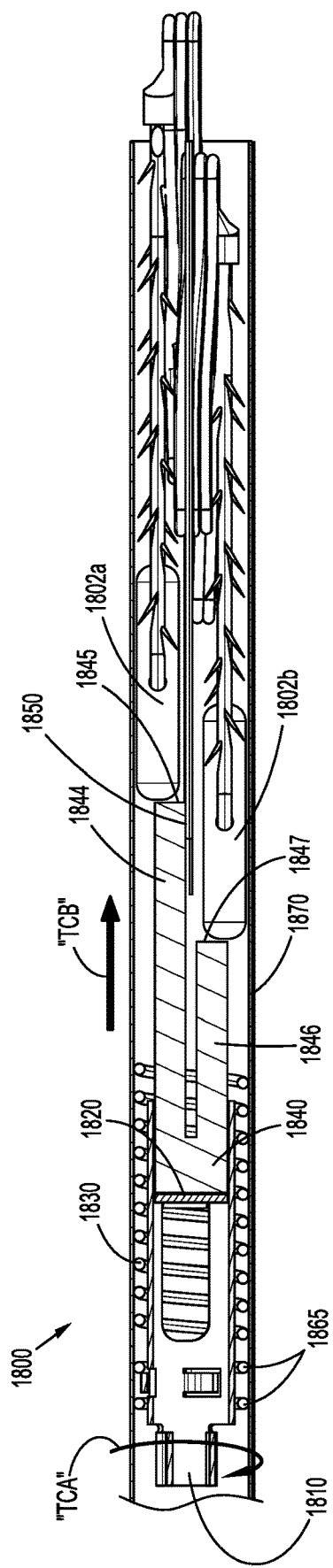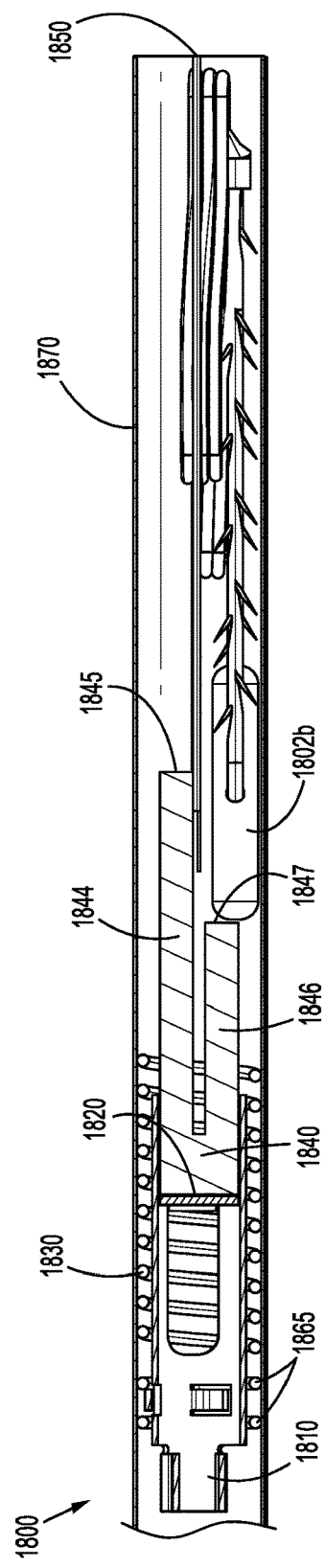

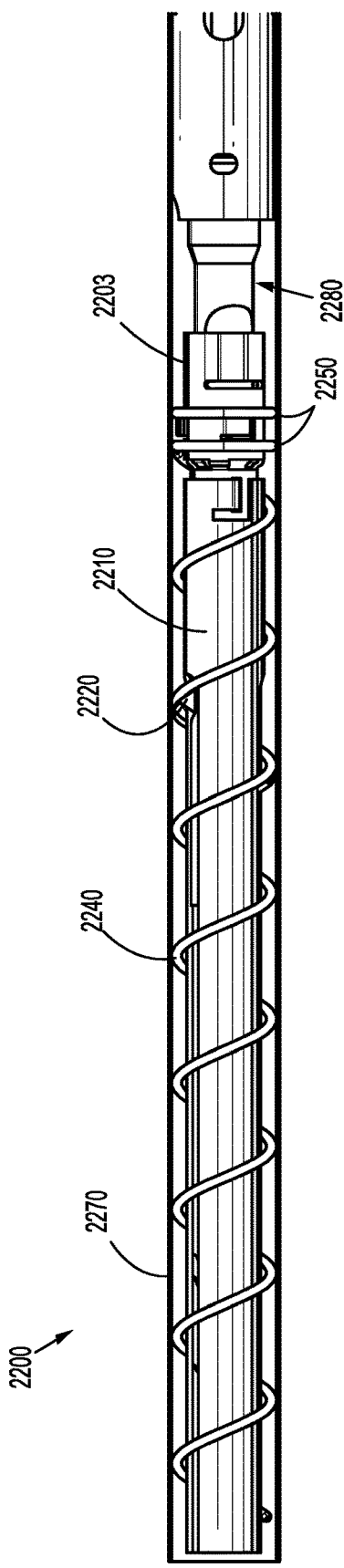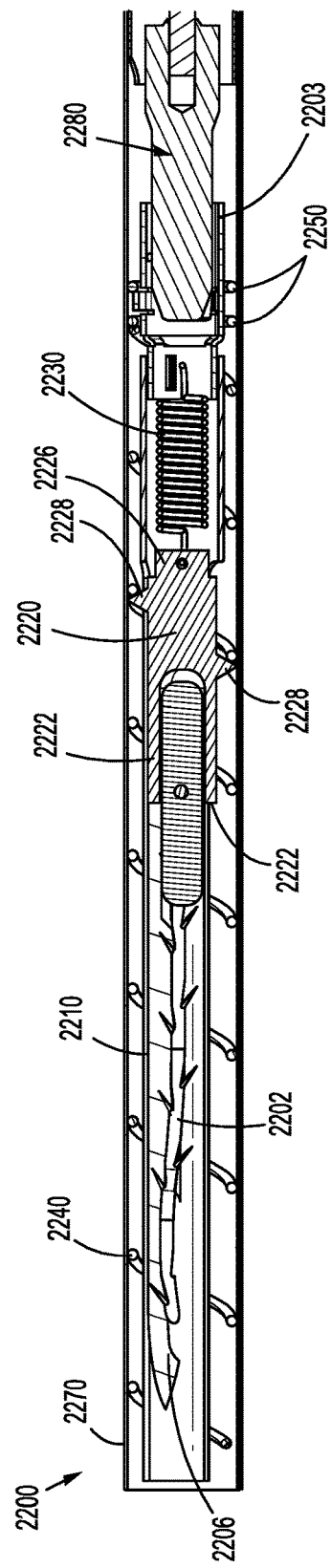
FIG. 54
FIG. 55

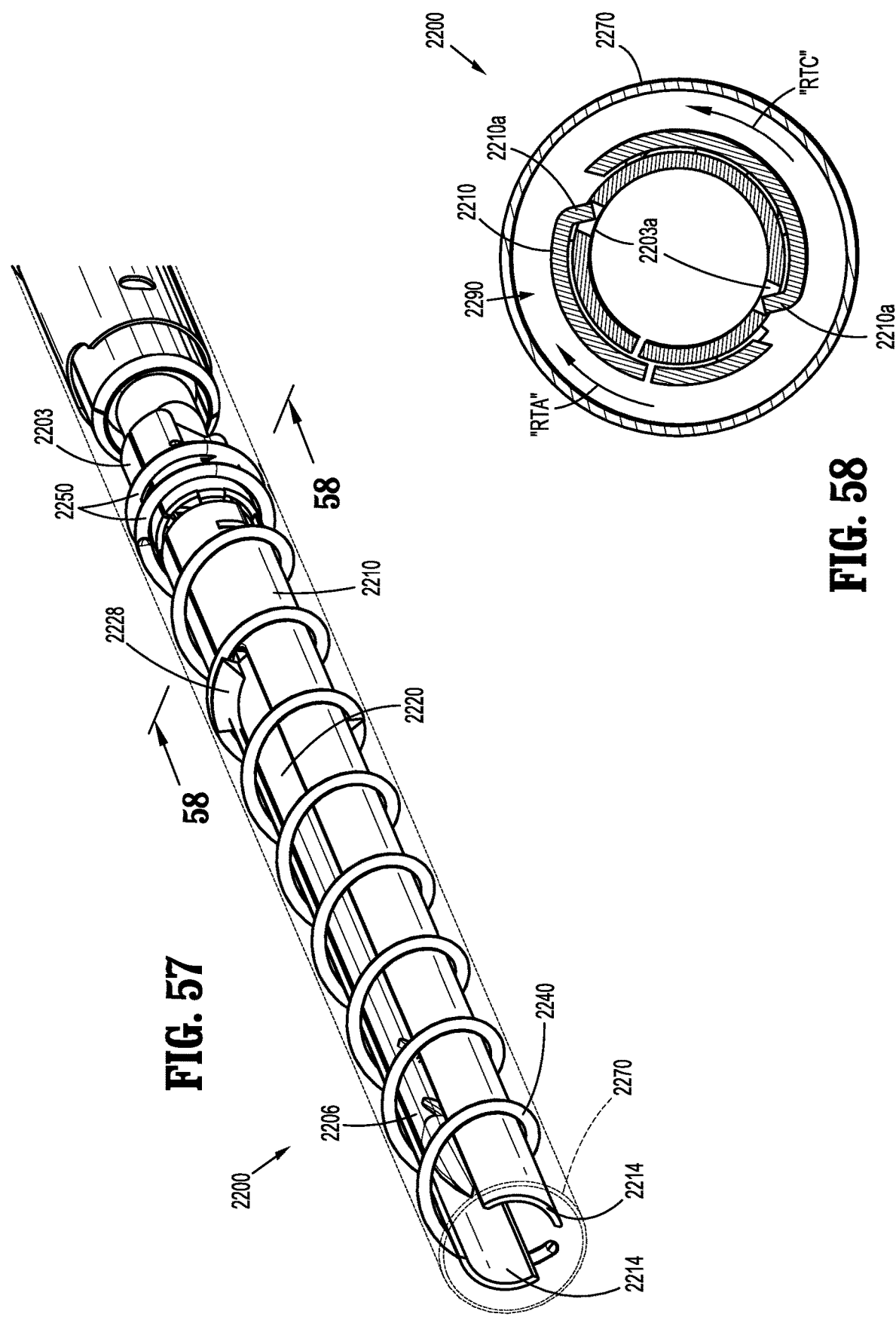

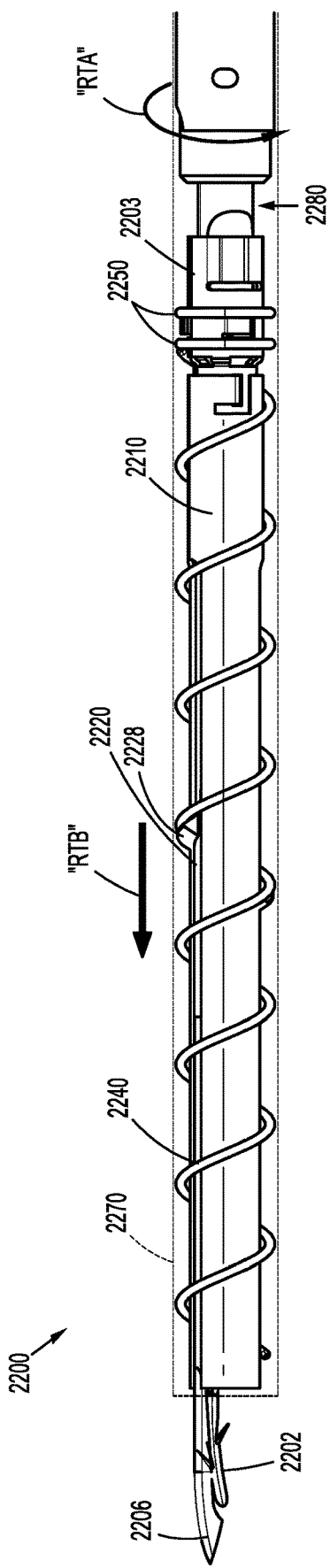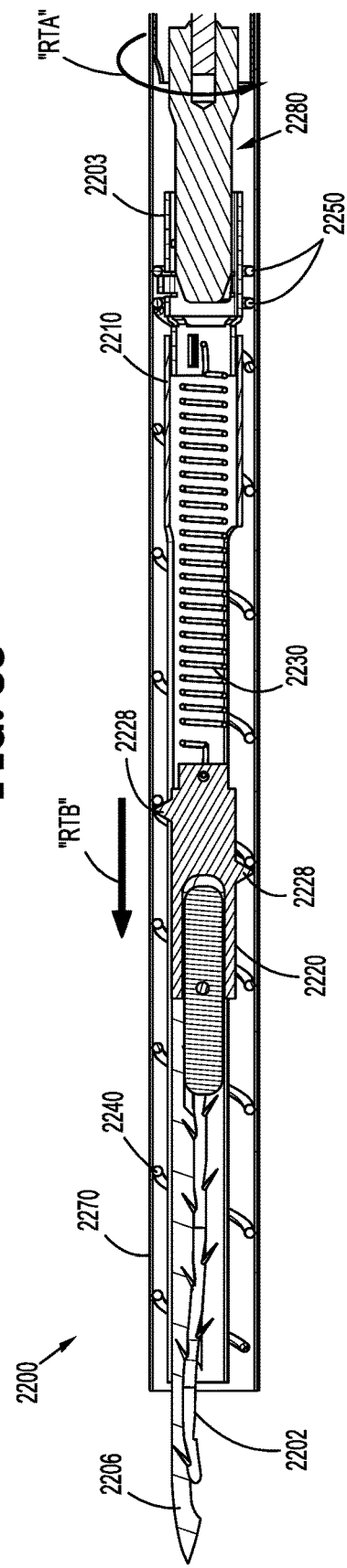
FIG. 59
FIG. 60

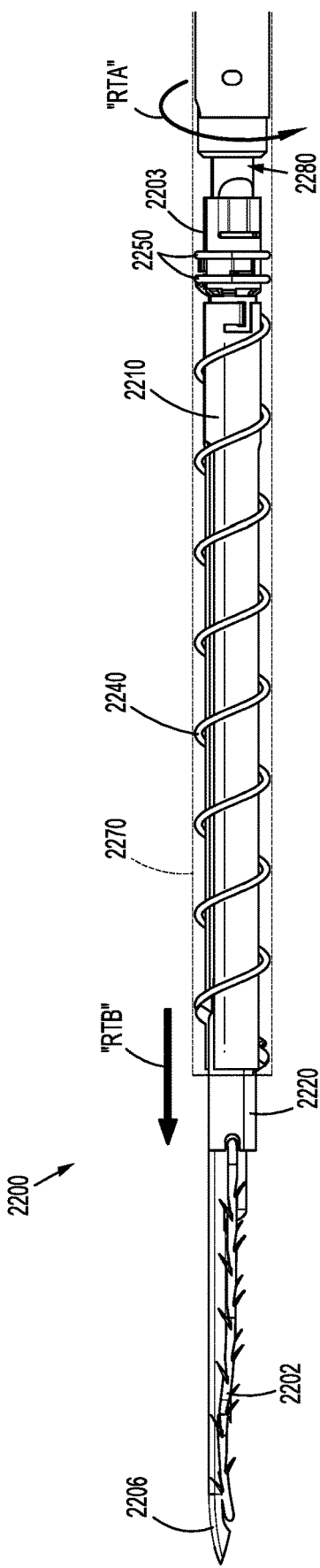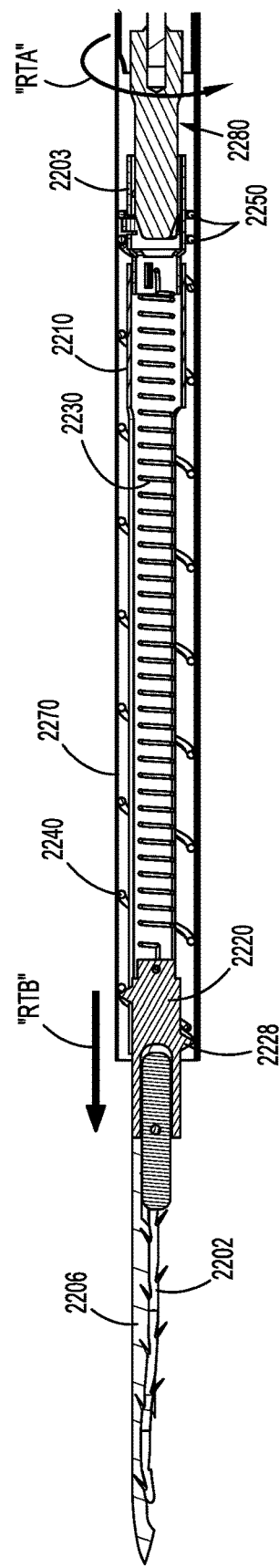
FIG. 61
FIG. 62

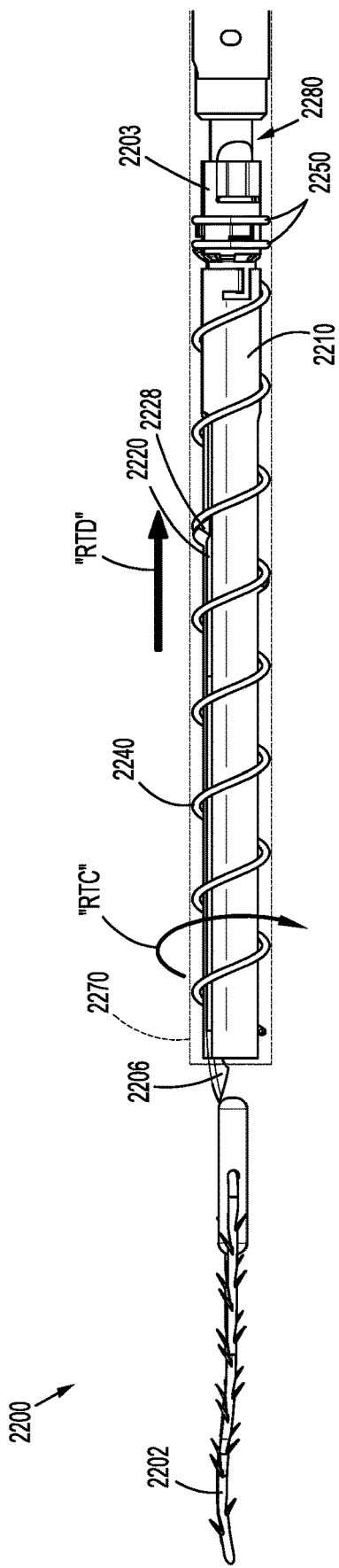
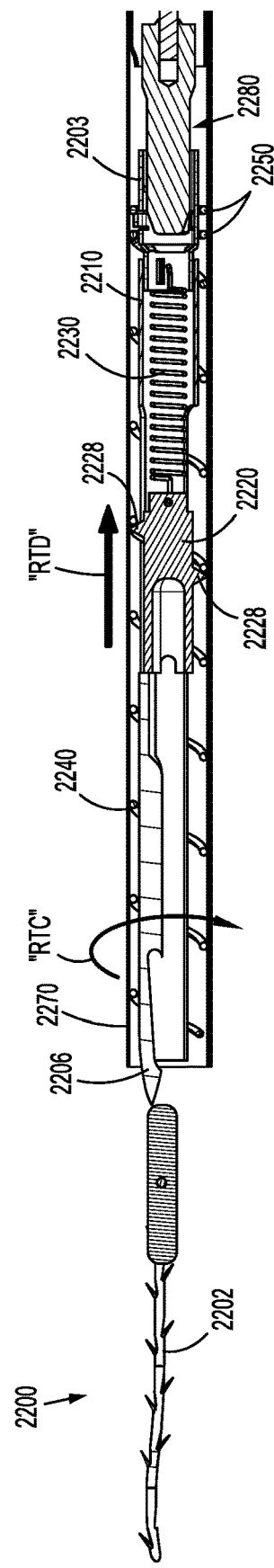
FIG. 63
FIG. 64

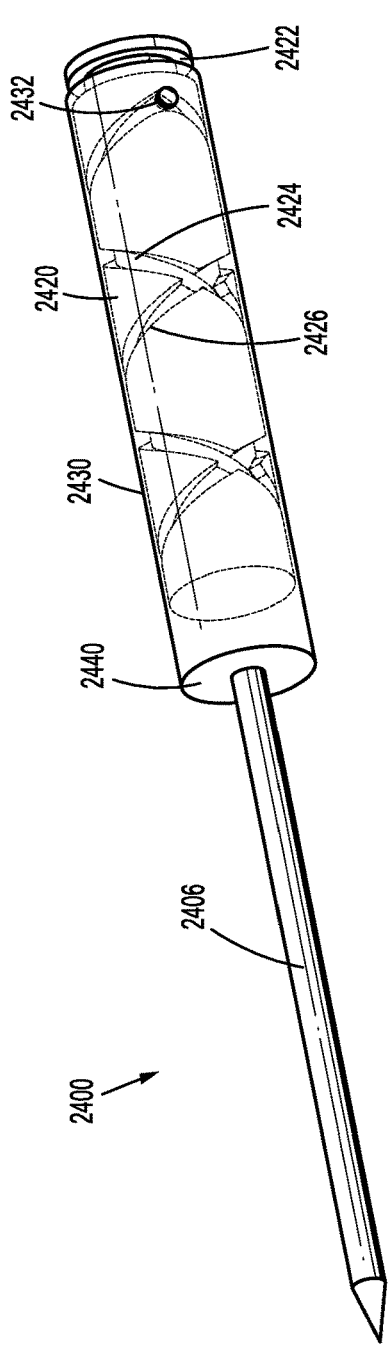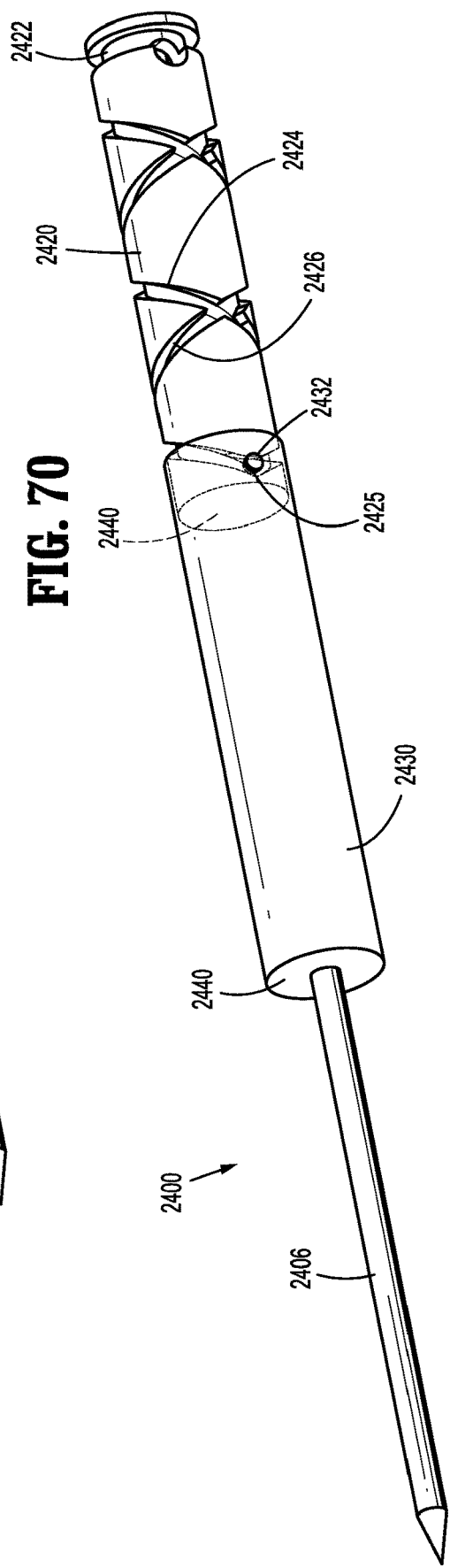

SURGICAL END EFFECTORS

CROSS-REFERENCE TO RELATED APPLICATIONS

This application claims the benefit of and priority to U.S. Provisional Patent Application No. 62/410,879 filed Oct. 21, 2016, the entire disclosure of which is incorporated by reference herein.

TECHNICAL FIELD

The present disclosure relates to end effectors for use with a surgical device for performing endoscopic surgical procedures and methods of use thereof. More specifically, the present disclosure relates to end effectors for advancing at least a portion of a needle into tissue.

BACKGROUND

During laparoscopic or endoscopic surgical procedures, access to a surgical site is achieved through a small incision or through a narrow cannula inserted through a small entrance wound in a patient. Several types of such surgical procedures include advancing at least part of a needle and/or suture into tissue. For example, it may be desired to insert a suture (e.g., a barbed suture) through an implant (e.g., mesh) and into tissue to help secure the implant to tissue. It may also be desired to replace suture that was previously inserted through the implant.

Additionally, after a needle is advanced into tissue, it may be desired to retract the needle in an outer tube of a surgical device or an end effector to prevent or minimize unintended contact between the needle and a physician, for instance.

Accordingly, a need exists for endoscopic surgical devices or end effectors for use therewith including the ability to advance and retract a needle into its outer tube.

SUMMARY

The present disclosure relates to an end effector for use with a surgical device. The end effector includes a drive assembly, a driver, a needle assembly, and a follower. The drive assembly is configured to rotate about a longitudinal axis and includes a first helical groove. The driver is disposed in mechanical cooperation with the drive assembly. Rotation of the drive assembly in a first direction causes distal translation of the driver with respect to the drive assembly. The needle assembly is disposed in mechanical cooperation with the driver. Distal translation of the driver causes a corresponding distal translation of the needle assembly. The follower is configured to engage the first helical groove of the drive assembly. When the follower is engaged with the first helical groove, rotation of the drive assembly in the first direction causes distal translation of the follower with respect to the drive assembly.

According to an aspect of the present disclosure, the drive assembly includes a second helical groove. The first helical groove encircles at least a portion of the drive assembly in a first direction, and the second helical groove encircles at least a portion of the drive assembly in a second direction. The first direction is opposite from the second direction. The follower is configured to engage the second helical groove of the drive assembly. It is disclosed that when the follower is engaged with the second helical groove of the drive assembly, rotation of the drive assembly in the first direction causes proximal translation of the follower with respect to the drive assembly. It is further disclosed that when the follower is engaged with the second helical groove of the drive assembly, rotation of the drive assembly in the first direction causes proximal translation of the needle assembly with respect to the drive assembly.

In disclosed embodiments, a portion of the follower extends through an aperture of the driver.

It is further disclosed that the end effector includes an outer tube disposed radially outward of at least a portion of the drive assembly. The end effector includes a suture disposed in mechanical cooperation with the needle assembly and disposed radially inward of the outer tube. In embodiments, the outer tube includes a longitudinal slot, and a portion of the follower is configured to engage the longitudinal slot of the outer tube.

It is also disclosed that the needle assembly includes a needle that is radially offset from the longitudinal axis.

In disclosed embodiments, the follower is pivotable about a pivot axis. The pivot axis is perpendicular to the longitudinal axis.

In aspects of the present disclosure, the end effector includes a pin disposed distally of the drive assembly. The pin extends through at least one longitudinal slot of the driver.

It is also disclosed that the needle assembly includes a first needle extending distally from a needle block, and second needle extending distally from the needle block. The first needle is parallel to the second needle.

The present disclosure also relates to an end effector for use with a surgical device. The end effector includes a drive assembly having cylindrical body, a first helical groove encircling a portion of the cylindrical body in a first direction, and a second helical groove encircling a portion of the cylindrical body in a second direction. The first direction being opposite from the second direction. The end effector also includes a suture disposed in mechanical cooperation with the drive assembly In embodiments, the proximal end of the first helical groove and the proximal end of the second helical groove are interconnected. Further, in embodiments, the distal end of the first helical groove and the distal end of the second helical groove are interconnected.

In aspects of the present disclosure, the first helical groove and the second helical groove share at least two points of intersection between their proximal ends and their distal ends. In embodiments, the first helical groove and the second helical groove share at least four points of intersection between their proximal ends and their distal ends.

In disclosed embodiments, a follower of the end effector is configured to move to the distal end of the first helical groove and directly into the distal end of the second helical groove.

Further details and aspects of exemplary embodiments of the present disclosure are described in more detail below with reference to the appended figures.

BRIEF DESCRIPTION OF THE DRAWINGS

Embodiments of the present disclosure are described herein with reference to the accompanying drawings, wherein:

FIGS. 1 and 2 are perspective views of a surgical device including an end effector engaged therewith according to embodiments of the present disclosure;

FIG. 3 is an enlarged view of the indicated area of detail of FIG. 2;

FIGS. 5-8 illustrate various types of needles and sutures in accordance with embodiments of the present disclosure;

FIGS. 9-20 illustrate various embodiments showing a needle engaged with a suture in accordance with embodiments of the present disclosure;

FIG. 23 is a cross-sectional view of a portion of the end effector of FIGS. 21 and 22;

FIG. 24 is a perspective view of a portion of the end effector of FIGS. 21-23;

FIG. 25 is a perspective view of portions of the end effector of FIGS. 21-24;

FIG. 26 is an enlarged view of the area of detail indicated in FIG. 25;

FIG. 27 is an enlarged view of the area of detail indicated in FIG. 25;

FIG. 28 is a perspective view of portions of the end effector of FIGS. 21-27;

FIG. 29 is a perspective view of the needle of FIG. 28;

FIG. 31 is a perspective view of portions of the end effector of FIGS. 21-30;

FIG. 32 is an enlarged view of the area of detail indicated in FIG. 31;

FIG. 33 is an enlarged view of the area of detail indicated in FIG. 31;

FIG. 34 is a perspective view of an end effector in accordance with embodiments of the present disclosure;

FIGS. 35 and 36 are cut-away views of portions of the end effector of FIG. 34;

FIG. 38 is a perspective view of an end effector in accordance with embodiments of the present disclosure;

FIG. 39 is a cross-sectional view of the end effector of FIG. 38;

FIG. 46 is a cross-sectional view of the end effector of FIGS. 42-45 illustrating a portion of a first barbed suture in an advanced position;

FIG. 47 is a cross-sectional view of the end effector of FIGS. 42-46 illustrating the first barbed suture ejected from the end effector;

FIG. 54 is a side view of portions of an end effector in accordance with embodiments of the present disclosure;

FIG. 55 is a cross-sectional view of the end effector of FIG. 54;

FIG. 57 is a perspective view of portions of the end effector of FIGS. 54-56;

FIG. 58 is a cross-sectional view of the end effector of FIGS. 54-57 taken along line 58-58 of FIG. 57;

FIG. 59 is a side view of portions of the end effector of FIGS. 54-58 illustrating a portion of a needle in an advanced position;

FIG. 60 is a cross-sectional view of the end effector of FIGS. 54-59 illustrating a portion of the needle in an advanced position;

FIG. 61 is a side view of portions of the end effector of FIGS. 54-60 illustrating a portion of the needle in a further advanced position;

FIG. 62 is a cross-sectional view of the end effector of FIGS. 54-61 illustrating a portion of the needle in the further advanced position of FIG. 61;

FIG. 63 is a side view of portions of the end effector of FIGS. 54-62 illustrating the needle moving toward its retracted position;

FIG. 64 is a cross-sectional view of the end effector of FIGS. 54-63 illustrating the needle moving toward its retracted position;

FIG. 70 is a perspective view of a driver in a proximal position relative to the drive shaft of the end effector of FIGS. 65-69; and FIG. 71 is a perspective view of the driver in a distal position relative to the drive shaft of the end effector of FIGS. 65-70.

DETAILED DESCRIPTION OF EMBODIMENTS

Figure 1:
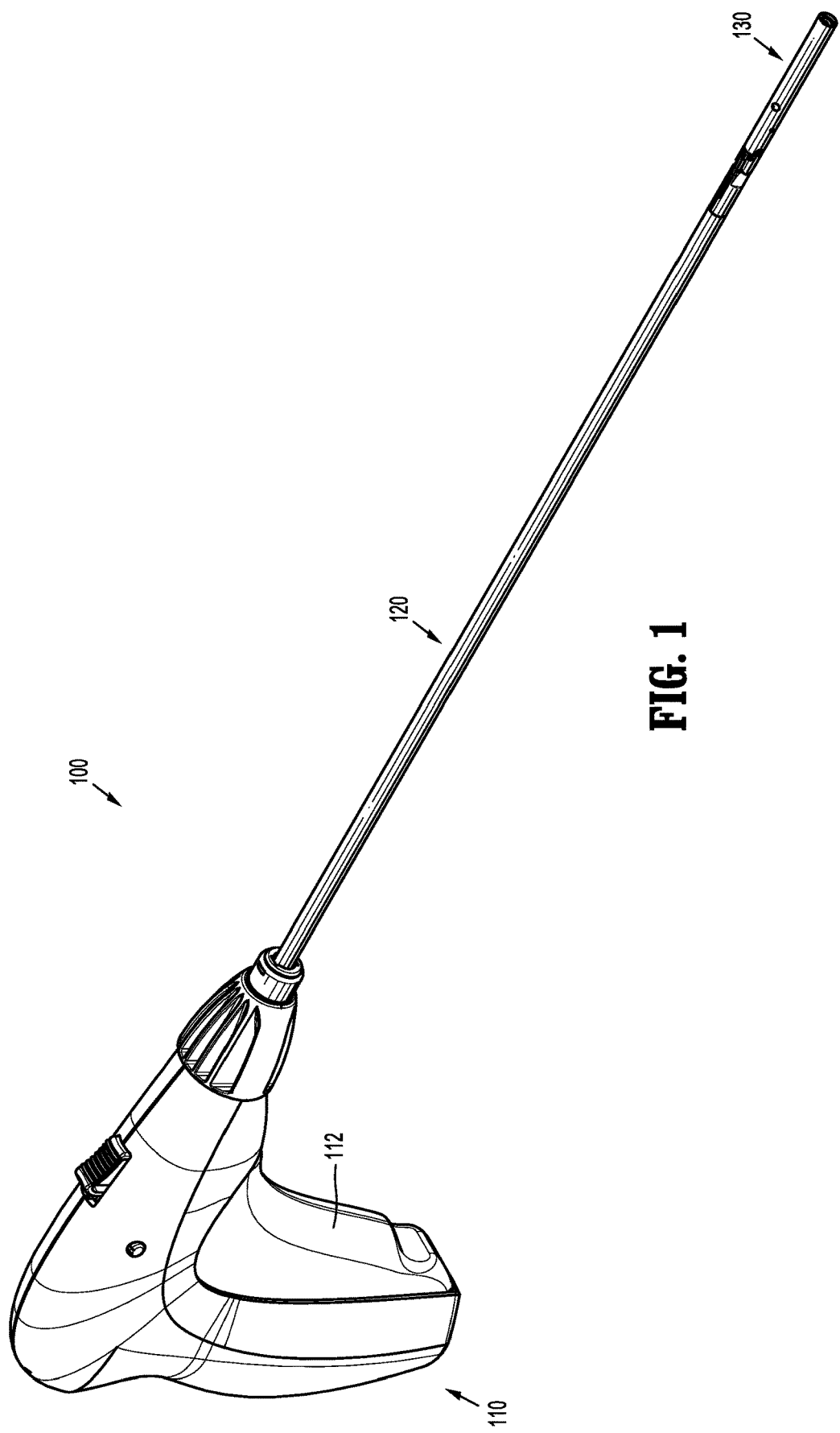
Figure 4:
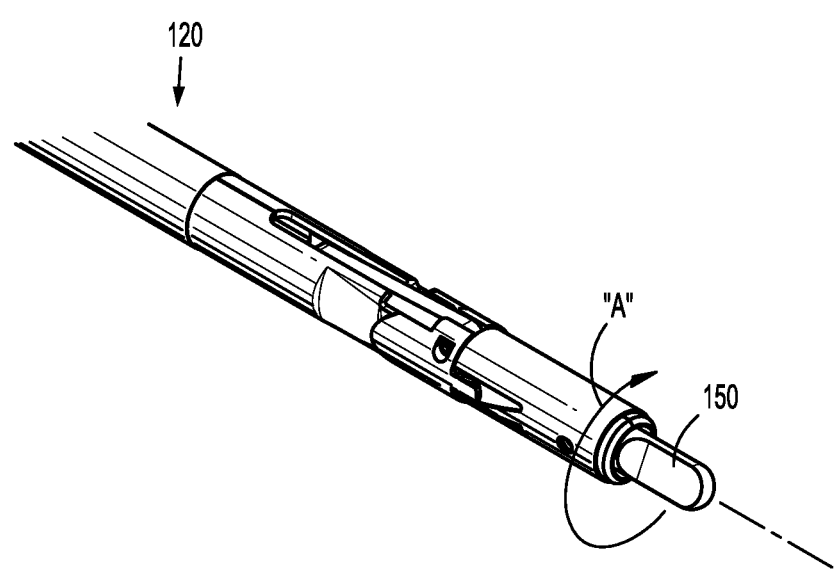
FIG. 4 is a perspective view of a distal portion of an elongated portion of the surgical device of FIGS. 1-3.

Embodiments of the presently disclosed endoscopic surgical device is described in detail with reference to the drawings, in which like reference numerals designate identical or corresponding elements in each of the several views. As used herein the term "distal" refers to that portion of the endoscopic surgical device that is farther from the user, while the term "proximal" refers to that portion of the surgical device that is closer to the user.

Non-limiting examples of surgical devices which may include articulation joints according to the present disclosure include manual, mechanical and/or electromechanical surgical tack appliers (i.e., tackers), clip appliers, surgical forceps, and the like.

Referring initial to FIGS. 1-4, a surgical instrument for use with the various end effectors of the present disclosure is generally designated as surgical device 100. Surgical device 100 includes a handle assembly 110, an elongated portion 120 extending distally from handle assembly 110, an end effector 130 disposed in mechanical cooperation (e.g., releasably engaged) with a distal portion of elongated portion 120, and a drive rod 150 disposed at least partially within elongated portion 120 and configured to engage (e.g., releasably engage) end effector 130. For clarity, FIGS. 1-3 illustrate a general end effector 130; various other end effectors are shown and described throughout this application and are configured for use with surgical device 100. Generally, end effector 130 is a separable component that is able to be used with a surgical instrument (e.g., a surgical fixation device handle). After its use (e.g., after one or more barbed sutures are released therefrom), the end effector 130 can be removed from the remainder of the surgical instrument, and a new or reloaded end effector 130 can then engage the surgical instrument and be used.

Handle assembly 110 includes a trigger or an actuator 112 (e.g., button, switch, etc.) thereon. In general, actuation of actuator 112 results in rotation of drive rod 150, e.g., in the general direction of arrow "A" in FIG. 4. There are a variety of ways surgical device 100 can transfer the movement caused by actuation of actuator 112 to rotation of drive rod 150, such as those disclosed in U.S. patent application Ser. No. 15/049,511, filed on Feb. 22, 2016, the entire contents of which are hereby incorporated by reference herein.

Several of the end effectors of the present disclosure are usable to advance at least a portion of a needle and/or at least a portion of a suture (e.g., a barbed suture) or other fixation device into tissue and/or mesh, for instance. An example of a disclosed use of the end effectors relates to positioning and/or fixation of laparoscopic ventral mesh. In such procedures, stay-sutures are typically tied to the corners and/or cardinal points by surgeons. The mesh and sutures are then rolled and introduced through the trocar and into the laparoscopic working space. The mesh is then unrolled, and positioned into place. If the sutures have needles attached, care must be taken during rolling, insertion, unrolling and positioning to help ensure the needle points do not damage the mesh (especially if the mesh includes an adhesion barrier layer) or to injure the patient or clinician. Once the mesh is properly unrolled and placed against the abdominal wall in the correct location, the stay-sutures are delivered across the abdominal wall (either from the inside toward the outside using an attached needle, or from the outside toward the inside using a suture passer introduced from outside the abdominal wall to grasp and pull the suture from the laparoscopic working space). After the stay-sutures have all been inserted, the clinician can finish fixating the mesh to the abdominal wall with a separate fixation device, such as a surgical tack applier.

The various end effectors disclosed herein help standardize surgical procedures (e.g., positioning and/or fixation of laparoscopic ventral mesh) and reduce the number of steps and time required to fixate the mesh with stay-sutures. The needle assemblies of the present disclosure allow a surgeon to introduce and pass a stay-suture through the implant and abdominal wall without the need to pre-attach the stay-sutures to needles, and without the risk of accidental needle sticks. The disclosed end effectors can used as a reload for use with standard surgical device handles to minimize the number of surgical devices (and the expense) needed for related surgical procedures.

Needle Styles

A variety of different types of needles may be used in combination with various embodiments of the present disclosure. While FIGS. 5-8 illustrate several types of needles, other types of needles may be used with the various end effectors disclosed herein. FIG. 5 illustrates a single needle 3000a extending from a needle block 3002, and a barbed suture 3010a operatively engaged (e.g., releasably engaged) therewith such that needle 3000a and barbed suture 3010a are insertable into an implant/tissue, and barbed suture 3010a remains in engagement with the implant/tissue when needle 3000a is retracted. A pledget 3003a is also included adjacent proximal portions of needle 3000a and barbed suture 3010a, which may releasably hold barbed suture 3010a, and which may act as a stop to help limit the distal advancement of barbed suture 3010a into the implant/tissue. A distal portion of barbed suture 3010a may be bent into a hollow cavity at a distal portion of needle 3000a to help releasably retain barbed suture 3010a in engagement with needle 3000a. FIG. 6 illustrates a pair of needles 3000b disposed in a parallel relationship extending from needle block 3002, and a suture 3010b supported between needles 3000b. Each needle of pair of needles 3000b extends distally from needle block 3002 in a direction that is perpendicular to a distal face 3002b of needle block 3002 (e.g., parallel to a longitudinal axis defined by an elongated portion of surgical device 100 engaged with needle block 3002). Pair of needles 3000b is sufficiently sturdy to support suture 3010b therebetween. A distal portion of suture 3010b may be bent into a hollow cavity at a distal portion of needle 3000b to help releasably retain suture 3010b in engagement with needles 3000b. It is envisioned that an adhesive is used to temporarily retain suture 3010b in the illustrated position. In use, at least a portion of needles 3000b and suture 3010b are inserted into/through an implant/tissue to emplace suture 3010b through the implant, for example. Suture 3010b remains emplaced through the implant up retraction of needles 3000b. Another suture 3010b can then be positioned between needles of pair of needles 3000b to allow for repeated use of pair of needles 3000b. FIG. 7 illustrates a pair of needles 3000c disposed in a bowed relationship extending from needle block 3002, and a suture 3010c supported between needles 3000c. Needles 3000c extend radially outward from each other, such that distal ends 3002c of needles 3000c are farther apart than proximal ends 3004c of needles 3000c. Pair of needles 3000c is sufficiently sturdy to support suture 3010c therebetween. A distal portion of suture 3010c may be bent into a hollow cavity at a distal portion of needle 3000c to help releasably retain suture 3010c in engagement with needles 3000c. It is envisioned that an adhesive is used to temporarily retain suture 3010c in the illustrated position. FIG. 8 illustrates a pair of needles 3000d extending in an arcuate manner from needle block 3002, and supporting a suture 3010d at least partially therebetween. Further, distal portions of suture 3010d are engaged with distal portions of needles 3000d. A distal portion of suture 3010d may be bent into a hollow cavity at a distal portion of needle 3000d to help releasably retain suture 3010d in engagement with needles 3000d. It is envisioned that an adhesive is used to temporarily retain suture 3010d in the illustrated position. Pair of needles 3000d may be used when a clinician desires to secure a relatively wide portion of an implant or tissue, as the distal tips of needles 3000d are positioned far away from each other, with respect to pair of needles 3000b and 3000c. It is envisioned that needles 3000a, 3000b, 3000c and 3000d are made from a shape memory material, such as nitinol.

Needle Tip Attachment

Figure 9:
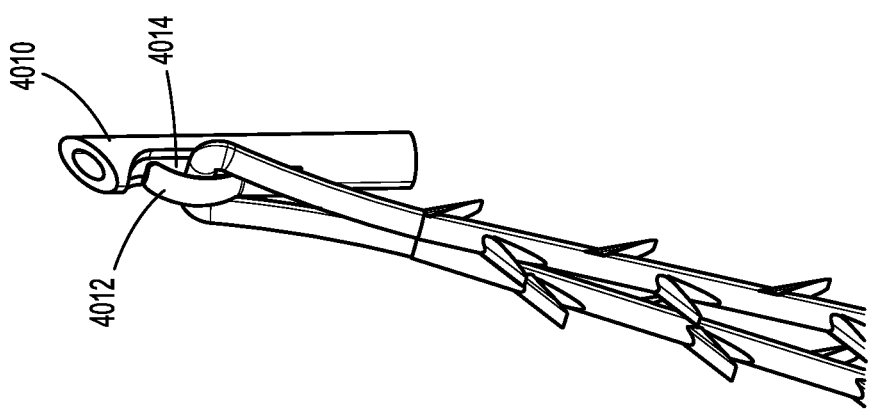

Several different ways of coupling needles with suture are usable with embodiments of end effectors disclosed herein and are illustrated in FIGS. 9-20. In FIG. 9, a needle 4010 is shown including a flange 4012 projecting from a recess 4014 within a shaft of needle 4010. A distal end of flange 4012 may be able to move, flex or pivot away from recess 4014. A barbed suture 4000 is releasably held by flange 4012. In use, distal advancement of needle 4010 towards (e.g., into) tissue causes a corresponding distal advancement of barbed suture 4000. When needle 4010 is moved proximally or retracted, flange 4012 moves over or releases barbed suture 4000, thus leaving barbed suture 4000 within tissue, for example.

Figure 11:
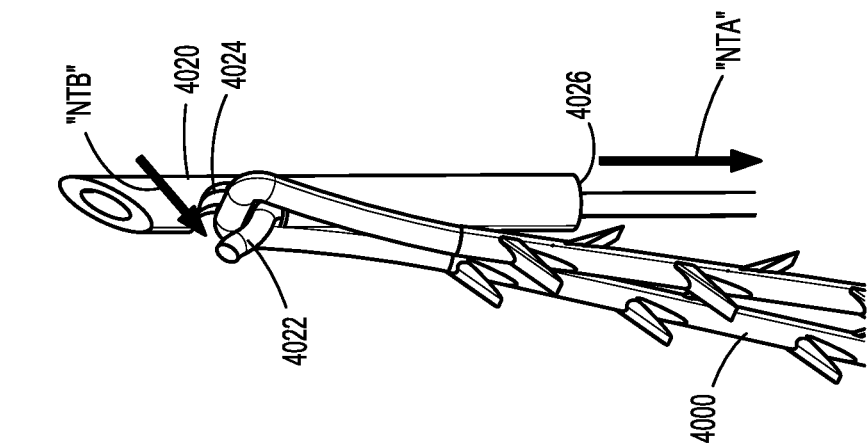
Figure 10:
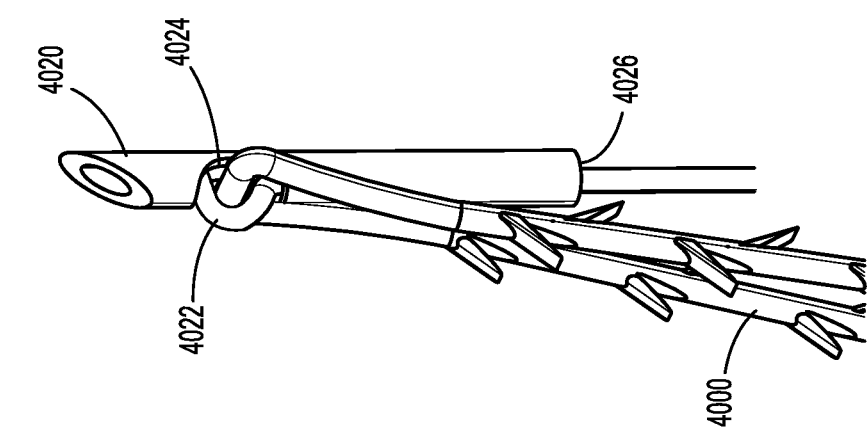

In FIGS. 10-11, a needle 4020 is shown including an actuation suture 4022 extending through needle 4020 between a recess 4024 within a shaft of needle 4020 and a proximal opening 4026 of needle 4020. A distal portion of actuation suture 4022 releasably holds barbed suture 4000. In use, distal advancement of needle 4020 towards (e.g., into) tissue causes a corresponding distal advancement of barbed suture 4000. When actuation suture 4022 is moved proximally or retracted in the general direction of arrow "NTA," distal portion of actuation suture 4022 moves in the general direction of arrow "NTB" or releases barbed suture 4000, thus leaving barbed suture 4000 within tissue, for example. It is envisioned that a proximal portion of actuation suture 4022 is engaged with an appropriate anchor portion of an end effector such that advancement of needle 4020 moves needle 4020 away from the anchor portion of the end effector, which causes a relative retraction of actuation suture 4022.

In FIGS. 12-13, a needle 4030 is shown including a suture 4002 engaged with a cavity 4032 of needle 4030. Cavity 4032 of needle 4030 includes a first, proximal portion 4032a and a second, distal portion 4032b. As shown, distal portion 4032b of cavity 4032 is deeper than proximal portion 4032a of cavity 4032. Distal portion 4032b of cavity 4032 is configured to releasably engage an enlarged or ball portion 4002a of suture 4002, and proximal portion 4032a of cavity 4032 is configured to releasably engage a body portion 4002b of suture 4002. In use, distal advancement of needle 4030 towards (e.g., into) tissue causes a corresponding distal advancement of suture 4002. When needle 4030 is moved proximally or retracted, suture 4002 is able to slide in the general direction of arrow "NTA" relative to needle 4030, thus leaving suture 4002 within tissue, for example.

Figure 15:
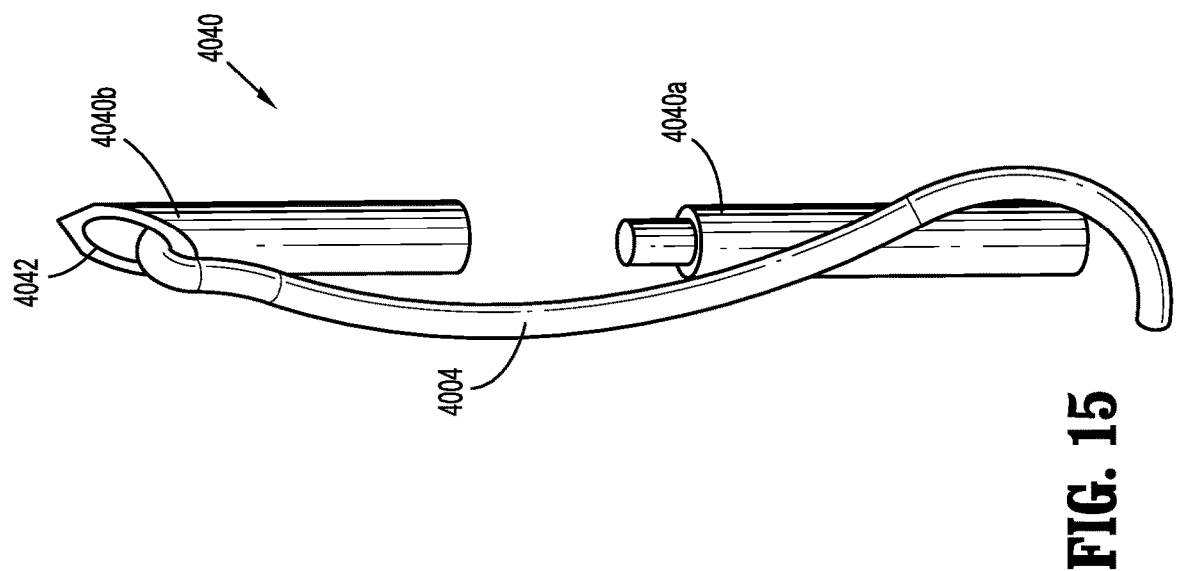
Figure 14:
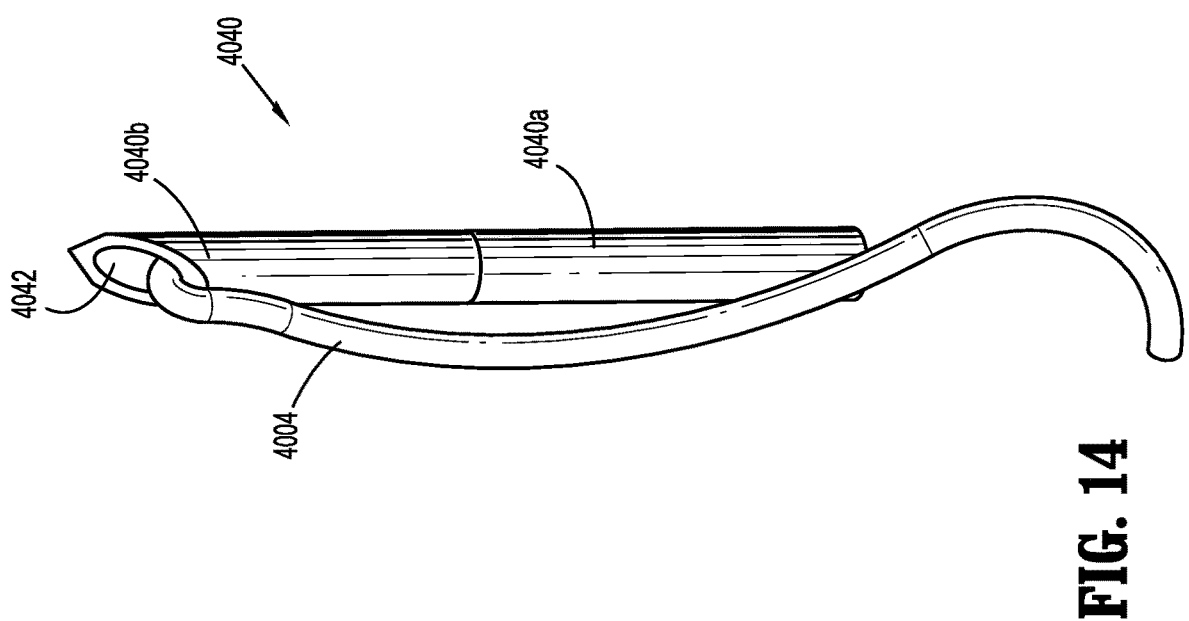

In FIGS. 14-15, a needle 4040 is shown including a proximal portion 4040a and a distal portion 4040b. Proximal portion 4040a and distal portion 4040b of needle 4040 are releasably engaged with each other. Accordingly, moving proximal portion 4040a proximally with respect to distal portion 4040b, for example, can separate the two portions of needle 4040. A suture 4004 is engaged with a distal part of distal portion 4040b of needle 4040. For example, a portion of suture 4004 is disposed within a cavity 4042 of distal portion 4040b of needle 4040. In use, distal advancement of needle 4040 towards (e.g., into) tissue causes a corresponding distal advancement of suture 4004. When proximal portion 4040a of needle 4040 is moved proximally or retracted, distal portion 4040b of needle 4040 separates from proximal portion 4040a, which results in distal portion 4040b of needle 4040 and portions of suture 4004 remaining in tissue.

Figure 16:
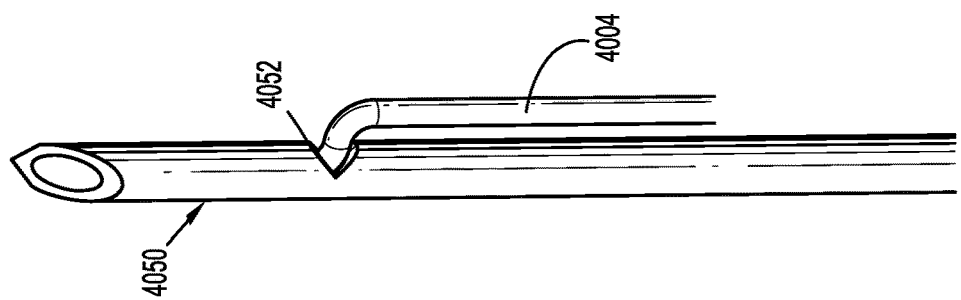

In FIG. 16, a needle 4050 is shown including an angled axial cut 4052 disposed therein. Angled axial cut 4052 of needle 4050 is configured to frictionally and releasably hold a portion of suture 4004 therein. In use, distal advancement of needle 4050 towards (e.g., into) tissue causes a corresponding distal advancement of suture 4004. When needle 4050 is moved proximally or retracted, portions of suture 4004 release from angled axial cut 4052 and remain within tissue, for example. It is envisioned that needle 4050 may be manufactured using an angled mill.

Figure 17:
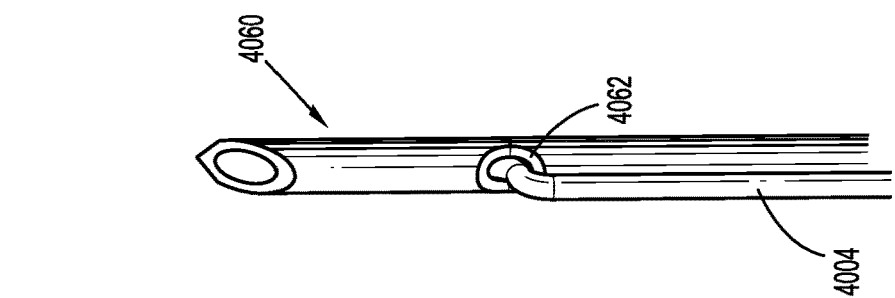

In FIG. 17, a needle 4060 is shown including a perpendicular axial cut 4062 disposed therein. Perpendicular axial cut 4062 of needle 4060 is configured to frictionally and releasably hold a portion of suture 4004 therein. In use, distal advancement of needle 4060 towards (e.g., into) tissue causes a corresponding distal advancement of suture 4004. When needle 4060 is moved proximally or retracted, portions of suture 4004 release from perpendicular axial cut 4062 and remain within tissue, for example. It is envisioned that needle 4060 may be manufactured using a cut off wheel.

Figure 18:
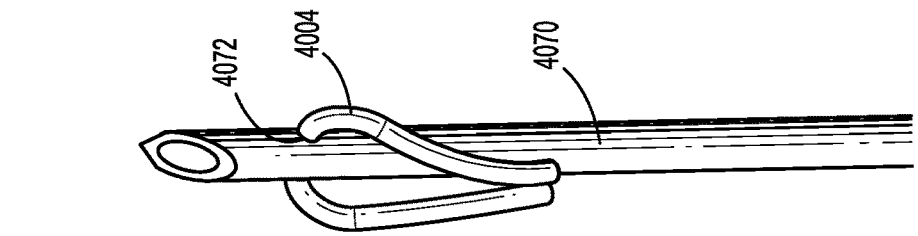

In FIG. 18, a needle 4070 is shown including a lateral aperture 4072 disposed therethrough. Lateral aperture 4072 of needle 4070 is configured to allow a portion of suture 4004 to be threaded therethrough. In use, distal advancement of needle 4070 towards (e.g., into) tissue causes a corresponding distal advancement of suture 4004. When needle 4070 is moved proximally or retracted, portions of suture 4004 are removed from lateral aperture 4072 and remain within tissue, for example. It is envisioned that a pin or wire travels through needle 4070 to sever suture 4004.

Figure 20:
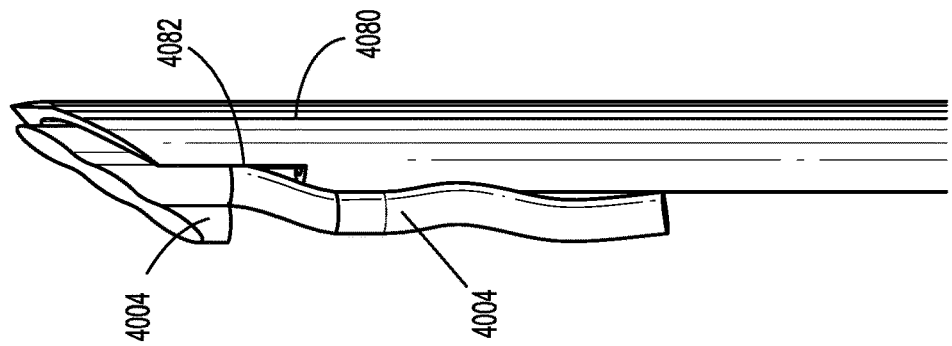
Figure 19:
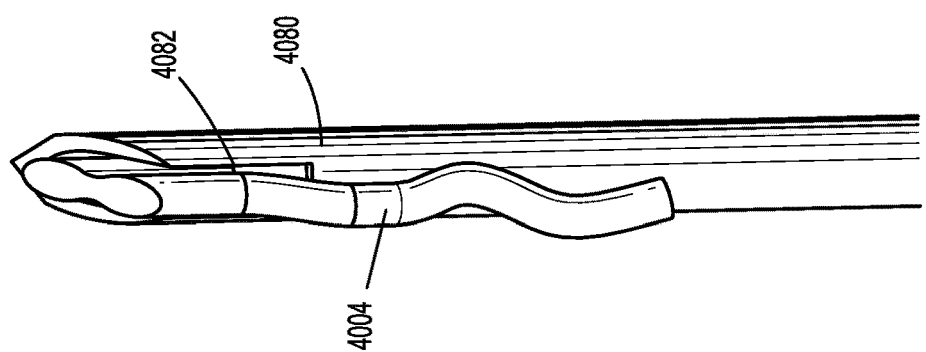

In FIGS. 19 and 20, a needle 4080 is shown including a slotted tip 4082. Slotted tip 4082 of needle 4080 is configured to frictionally and releasably hold a portion of suture 4004 (FIG. 19) or multiple sutures (FIG. 20) therein. In use, distal advancement of needle 4080 towards (e.g., into) tissue causes a corresponding distal advancement of suture(s) 4004. When needle 4080 is moved proximally or retracted, portions of suture(s) 4004 are removed from slotted tip 4082 and remain within tissue, for example.

Spring Loaded Safety Cover

Referring now to FIGS. 21-33, an embodiment of an end effector 1000 including a spring-loaded safety cover assembly is shown. End effector 1000 is configured for use in connection with surgical device 100. Generally, end effector 1000 is configured to prevent unintentional contact with a needle and/or a barbed suture within or extending distally from its outer tube. While FIGS. 21-33 illustrate a particular type of barbed suture 1002 and a particular type of needle 1006, end effector 1000 may be used with different types of sutures and/or needles.

Figure 21:
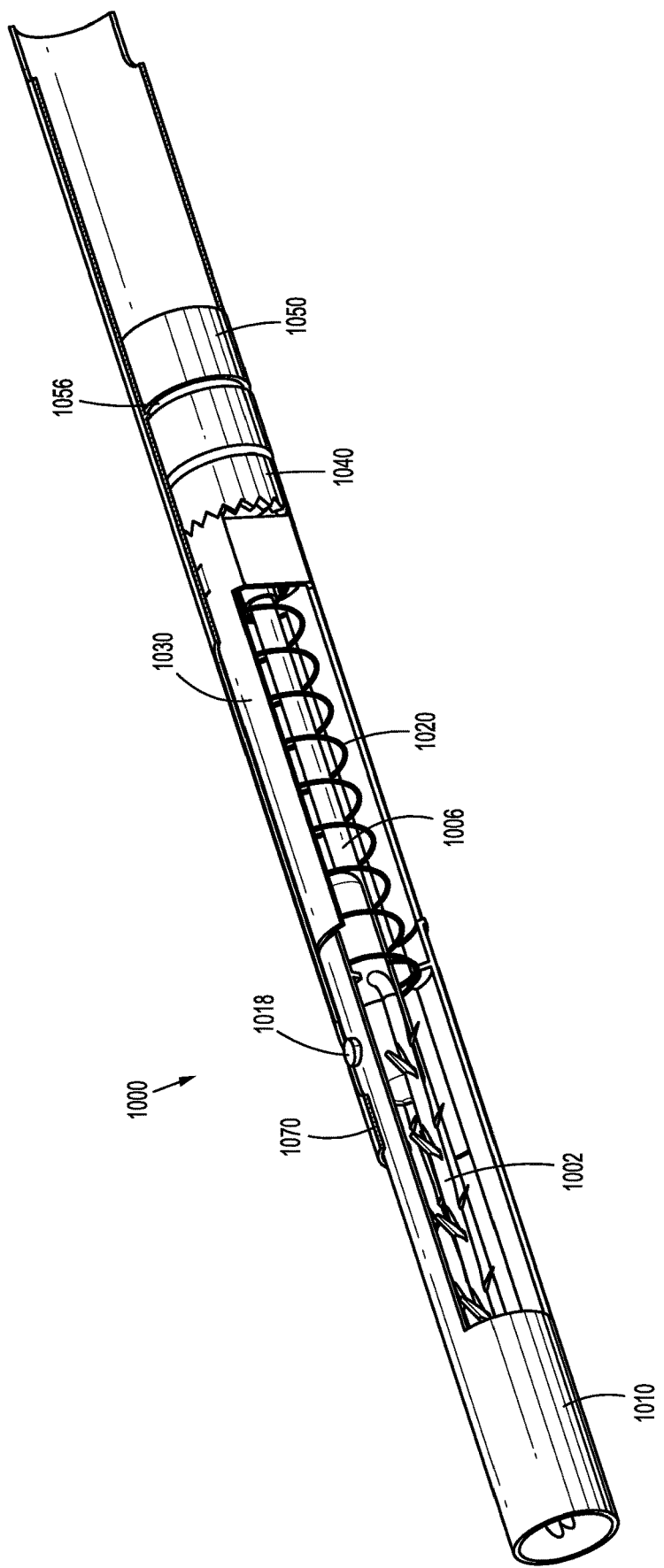
FIG. 21 is a perspective view of portions of an end effector in accordance with embodiments of the present disclosure.
Figure 22:
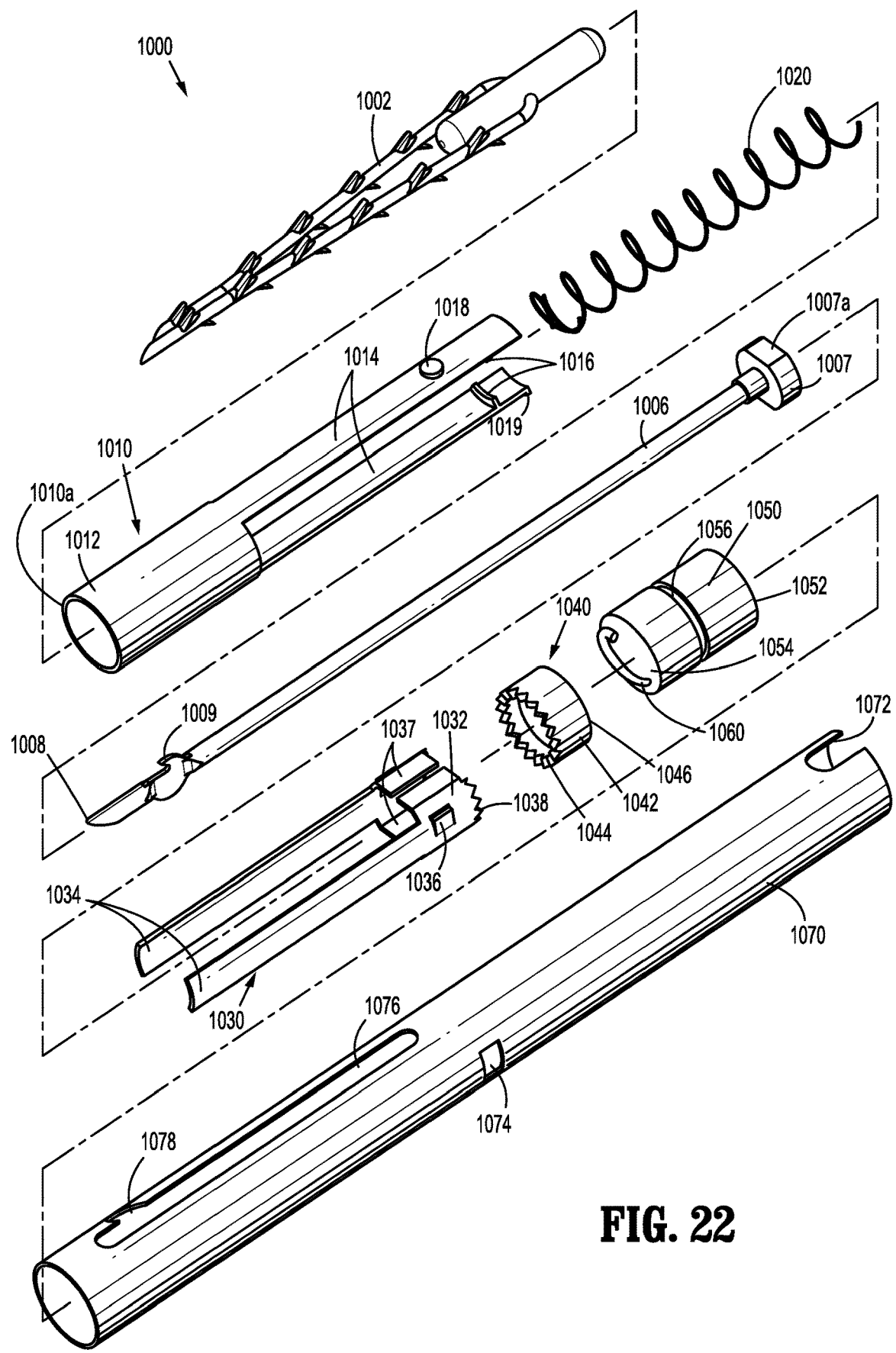
FIG. 22 is an assembly view of the end effector of FIG. 21.
Figure 30:
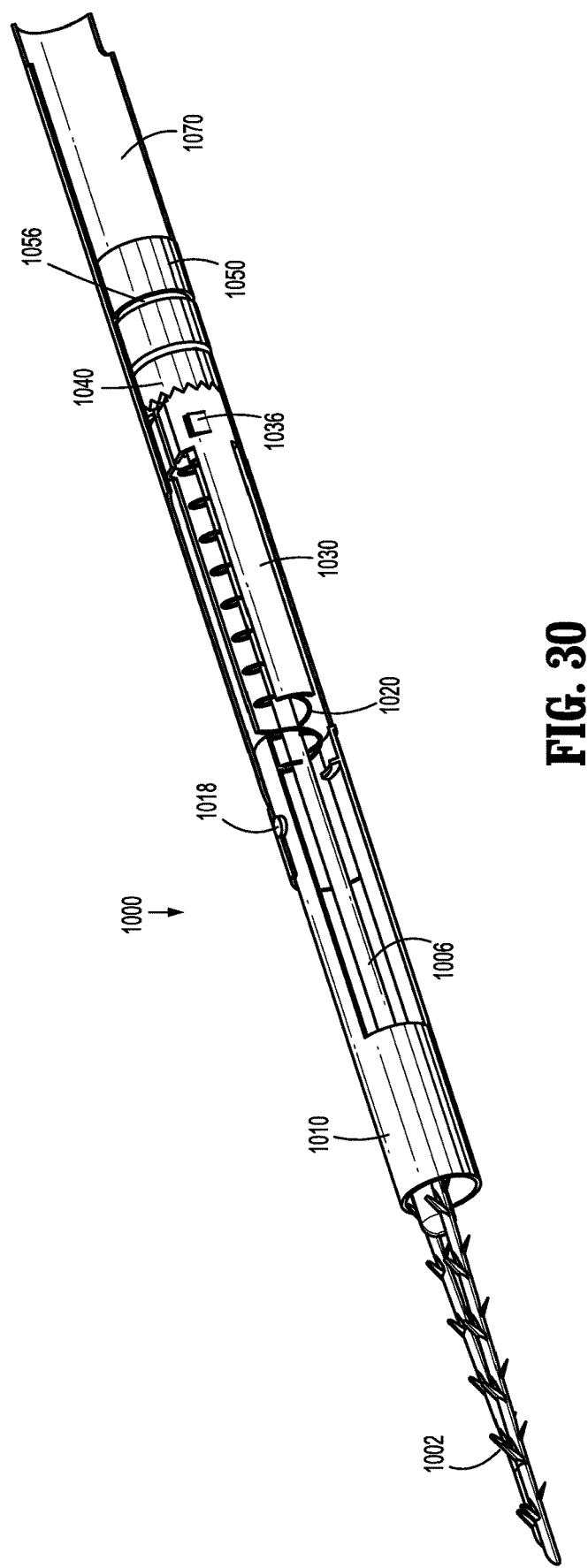
FIG. 30 is a perspective view of portions of the end effector of FIGS. 21-27 and with a needle in an advanced position.

With particular reference to FIGS. 21 and 22, end effector 1000 includes a cover 1010, a first biasing element or spring 1020, a clevis 1030, a clutch 1040, a drive element 1050, a second biasing element or spring 1060 (FIG. 22), and an outer tube 1070.

Cover 1010 of end effector 1000 includes a cylindrical body portion 1012, a pair of arms 1014 extending proximally from body portion 1012, a lip 1016 extending radially inward from a proximal portion of each arm 1014, and a tab 1018 extending radially outward from a proximal portion of one the arms 1014.

Clevis 1030 of end effector 1000 includes a body portion 1032, a pair of arms 1034 extending distally from body portion 1032, a flange 1036 extending radially outward from body portion 1032, and a plurality of teeth 1038 disposed on a proximal end of body portion 1032. First biasing element 1020 is positioned between arms 1034 of clevis 1030 and arms 1014 of cover 1010. Body portion 1032 of clevis 1030 engages a proximal end of first biasing element 1020; lips 1016 of cover 1010 engage a distal end of first biasing element 1020.

A proximal portion 1007 of needle 1006 is positioned radially inward of body portion 1032 of clevis 1030. Further, flat portions 1007*a* (see FIG. 28) of proximal portion 1007 of needle 1006 engage corresponding flat portions 1037 of body portion 1032 of clevis 1030, thus limiting or preventing rotation therebetween. Needle 1006 also includes a distal tip 1008 and a hook 1009. Distal tip 1008 of needle 1006 is configured to pierce tissue, and hook 1009 of needle 1006 is configured to engage a portion of barbed suture 1002.

Clutch 1040 of end effector 1000 includes a body portion 1042, a plurality of teeth 1044 disposed on a distal end of body portion 1042, and a proximal surface 1046. Teeth 1044 of clutch 1040 are configured to engage teeth 1038 of clevis 1030.

Drive element 1050 of end effector 1000 is mechanically engaged (e.g., operatively coupled, directly affixed, etc.) to drive rod 150 of surgical device 100 of the present disclosure. Drive element 1050 includes a proximal end 1052, a distal end 1054, and a groove 1056. Groove 1056 of drive element 1050 is configured to engage a shipping wedge (not shown) to help lock drive element 1050 in place with respect to outer tube 1070, for example. Proximal end 1052 of drive element 1050 is configured to engage the drive rod. Distal end 1054 of drive element 1050 is mechanically engaged with second biasing element 1060. Proximal surface 1046 of clutch 1040 is positioned to engage second biasing element 1060. That is, second biasing element 1060 is positioned between proximal surface 1046 of clutch 1040 and distal end 1054 of drive element 1050.

Outer tube 1070 of end effector 1000 includes a proximal notch 1072, a cutout 1074, and a longitudinal groove 1076 having an angled slot 1078 extending therefrom. Outer tube 1070 is configured for positioning radially outward of, and to at least partially contain, at least portions of barbed suture 1002, needle 1006, cover 1010, first biasing element 1020, clevis 1030, clutch 1040, drive element 1050, and second biasing element 1060.

As shown in FIG. 23, prior to use, a portion of proximal notch 1072 is longitudinally aligned with groove 1056 of drive element 1050 such that a shipping wedge (not shown) can extend through proximal notch 1072 and into engagement with groove 1056. The engagement between drive element 1050, second biasing element 1060, clutch 1040, and clevis 1030 is also shown in FIG. 23. As shown, second biasing element 1060 is disposed between drive element 1050 and clutch 1040, thus transferring rotational movement from drive element 1050 (and drive rod 150, as discussed above) to clutch 1040. Additionally, second biasing element 1060 enacts a distal force onto clutch 1040 to help maintain engagement between teeth 1044 of clutch 1040 and teeth 1038 of clevis 1030. Accordingly, rotation of clutch 1040 results in a corresponding rotation of clevis 1030.

With particular reference to FIG. 24, prior to use, tab 1018 of cover 1010 of end effector 1000 is disposed within angled slot 1078 of longitudinal groove 1076 of outer tube 1070. The engagement between tab 1018 and angled slot 1078 prevents cover 1010 from distally advancing with respect to outer tube 1070. In this position, cover 1010 is in its distal-most position where it radially surrounds distal tip 1008 of needle 1006 and barbed suture 1002.

In use, in response to at least a partial actuation of the trigger, the drive rod 150 rotates, as discussed above. Rotation of the drive rod results in a corresponding rotation of drive element 1050, clutch 1040, and clevis 1030. A predetermined amount of rotation (e.g., about) 90°) of clevis 1030 causes flange 1036 of clevis 1030 to rotate in the general direction of arrow "FLA" from a first position within cutout 1074 of outer tube 1070, to a second position where flange 1036 engages a lateral wall 1074*a* of cutout 1074 of outer tube 1070 (see FIG. 27). Engagement between flange 1036 and lateral wall 1074*a* prevents continued rotation of clevis 1030 with respect to outer tube 1070 in the direction of arrow "FLA." Accordingly, when clevis 1030 continues to rotate in the direction of arrow "FLA" (e.g., in response to continued or additional actuation of the trigger), outer tube 1070 also rotates in the direction of arrow "FLA" with respect to cover 1010.

Rotation of outer tube 1070 in the direction of arrow "FLA" with respect to cover 1010 causes angled slot 1078 of outer tube 1070 to disengage from tab 1018 of cover 1010, which causes tab 1018 of cover 1010 to be within longitudinal groove 1076 of outer tube 1070. When tab 1018 of cover 1010 is within longitudinal groove 1076 of outer tube 1070, cover 1010 is in an unlocked position.

Next, a user presses a distal tip of surgical device 100 against tissue and/or mesh to emplace barbed suture 1002 at least partially therein and/or therethrough. More particularly, the user pushes a distal edge 1010*a* of cover 1010 against the tissue/mesh, which causes cover 1010 to move proximally with respect to outer tube 1070 against the bias of first biasing element 1020. As cover 1010 moves proximally, tab 1018 of cover 1010 travels proximally within longitudinal groove 1076 of outer tube 1070. The proximal movement of cover 1010 exposes barbed suture 1002 and distal tip 1008 of needle 1006, at least portions of which extend distally beyond outer tube 1070, and enables barbed suture 1002 and distal tip 1008 to penetrate the tissue/mesh.

As the user moves the surgical device 100 proximally (e.g., after barbed suture 1002 has been emplaced in tissue/mesh), first biasing element 1020 urges cover 1010 distally with respect to outer tube 1070. Cover 1010 continues to move distally while tab 1018 of cover 1010 travels within longitudinal groove 1076 of outer tube 1070 until tab 1018 contacts a distal edge 1076*a* of longitudinal groove 1076, preventing further distal movement of cover 1010 with respect to outer tube 1070 (see FIGS. 31 and 32). Further, as tab 1018 of cover 1010 contacts distal edge 1076*a* of longitudinal groove 1076, at least one proximal finger 1019 of cover 1010 enters an aperture 1071 of outer tube 1070 (e.g., in response to a radial outward bias of arms 1014), thus effectively locking the longitudinal position of cover 1010 with respect to outer tube 1070 (see FIGS. 31 and 33).

Folding Safety Cover

With reference to FIGS. 34-37, a safety cover assembly 2800 for use with various end effectors disclosed herein is shown. A cover 2810 of safety cover assembly 2800 is configured to pivot between a first position where safety cover 2800 helps prevent unintentional contact with a needle 2806 (FIG. 34), and a second position where safety cover 2800 allows needle 2806 to be driven into tissue (FIG. 35).

Figure 37:
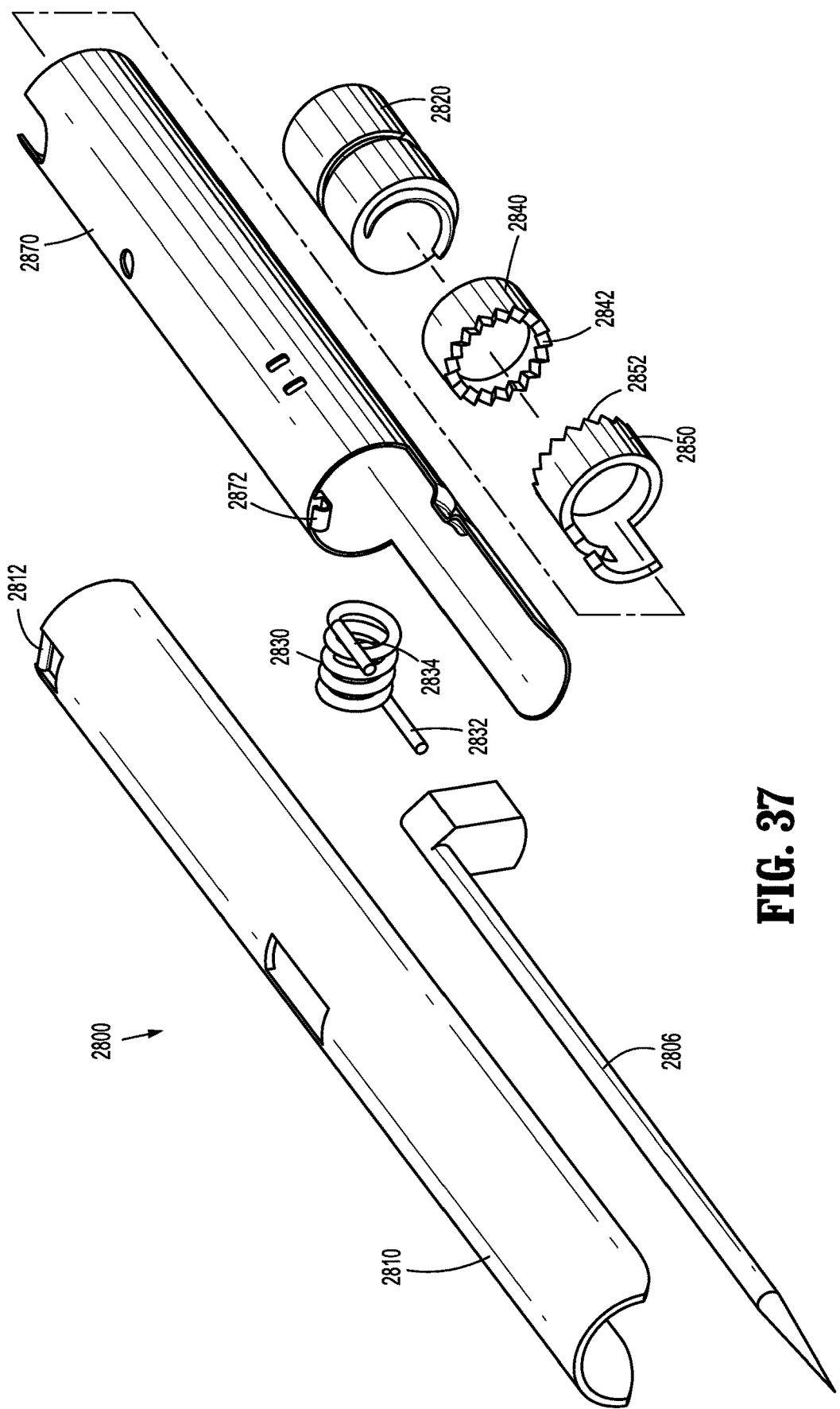
FIG. 37 is an assembly view of the end effector of FIGS. 34-36.

With particular reference to FIG. 37, safety cover assembly 2800 includes cover 2810, a drive member 2820, a biasing member 2830, a gear 2840, a clutch 2850, and an outer tube 2870. Cover 2810 includes a proximal lip 2812, and an angled blocking portion 2814 (FIG. 36). Proximal lip 2812 is configured to pivotably engage a distal finger 2872 of outer tube 2870 to facilitate pivotal movement therebetween. Blocking portion 2814 of cover 2810 is configured to selectively engage a portion of needle 2806 and/or clutch 2850. The engagement between blocking portion 2814 and needle 2806 and/or clutch 2850 restricts the biasing force supplied by biasing member 2830.

Biasing member 2830 of cover assembly 2800 includes a first portion 2832 engaged with (e.g., affixed to) a proximal portion of needle 2086, and a second portion 2834 engaged with (e.g., affixed to) a proximal portion of cover 2810. Biasing member 2830 is configured to bias cover 2810 away from needle 2806 toward its second position (FIG. 35). As noted above, the engagement between blocking portion 2814 of cover 2810 and needle 2806 and/or clutch 2850 resists the biasing force supplied by biasing member 2830.

Drive member 2820, gear 2840, and clutch 2850 of cover assembly 2800 are disposed radially within outer tube 2870. Drive member 2820 is mechanically engaged (e.g., operatively coupled, directly affixed, etc.) to drive rod 150 of surgical device 100 of the present disclosure. Accordingly, rotation of the drive rod 150 in the general direction of arrow "FSA" results in a corresponding rotation of drive member 2820. Additionally, drive member 2820 is configured to engage gear 2840 such that rotation of drive member 2820 in the general direction of arrow "FSA" causes a corresponding rotation of gear 2840 in the general direction of arrow "FSA." Further, gear 2840 is configured to engage clutch 2850 such that rotation of gear 2840 in the general direction of arrow "FSA" causes a corresponding rotation of clutch 2850.

With reference to FIGS. 35-37, clutch 2850 of cover assembly 2800 is configured to engage a portion of cover 2810, such that rotation of clutch 2850 in the general direction of arrow "FSA" causes a corresponding rotation of cover 2810 in the general direction of arrow "FSA." With particular reference to FIG. 36, rotation of cover 2810 in the general direction of arrow "FSA" causes blocking portion 2814 of cover 2810 to rotate with respect to needle 2806, such that blocking portion 2814 no longer resists the force exerted by biasing member 2830 onto cover 2810. Accordingly, rotation of drive rod 150 in the general direction of arrow "FSA" causes a corresponding rotation of drive member 2820, gear 2840, clutch 2850 and cover 2810, thus causing cover 2810 to pivot in the general direction of arrow "FSB" (FIG. 35) toward its second position, since blocking portion 2814 no longer resists the force exerted by biasing member 2830 onto cover 2810. Additionally, proximal teeth 2852 of clutch 2850, which mate with distal teeth 2842 of gear 2840, are configured to skip following additional rotation of gear 2840 after cover 2810 moves toward its second position.

When cover 2810 is in its second position, needle 2806 is exposed and is able to be driven into tissue, for example. If a user desires to move cover 2810 back toward its first position, the user may use a secondary instrument or the user's hand, to pivot cover 2810 toward its first position against the bias of biasing member 2830. The cover 2810 can be rotated in the general direction of arrow "FSC" (FIG. 35) such that blocking portion 2814 engages needle 2806 and resists the force exerted by biasing member 2830.

Single Cartridge Design

Referring now to FIGS. 38-41, an embodiment of an end effector 1600 is shown. End effector 1600 includes a barbed suture 1602 at least partially therein, and is configured for use in connection with surgical device 100. Additionally, end effector 1600 is configured for use with a separate instrument (e.g., a needle suture passer) to drive and/or implant the suture in tissue. Generally, end effector 1600 is configured to advance barbed suture 1602 distally, such that a suture 1603 of barbed suture 1602 is graspable by a user.

While FIGS. 38-41 illustrate a particular type of barbed suture 1602, end effector 1600 may be used with different types of sutures.

Figure 40:
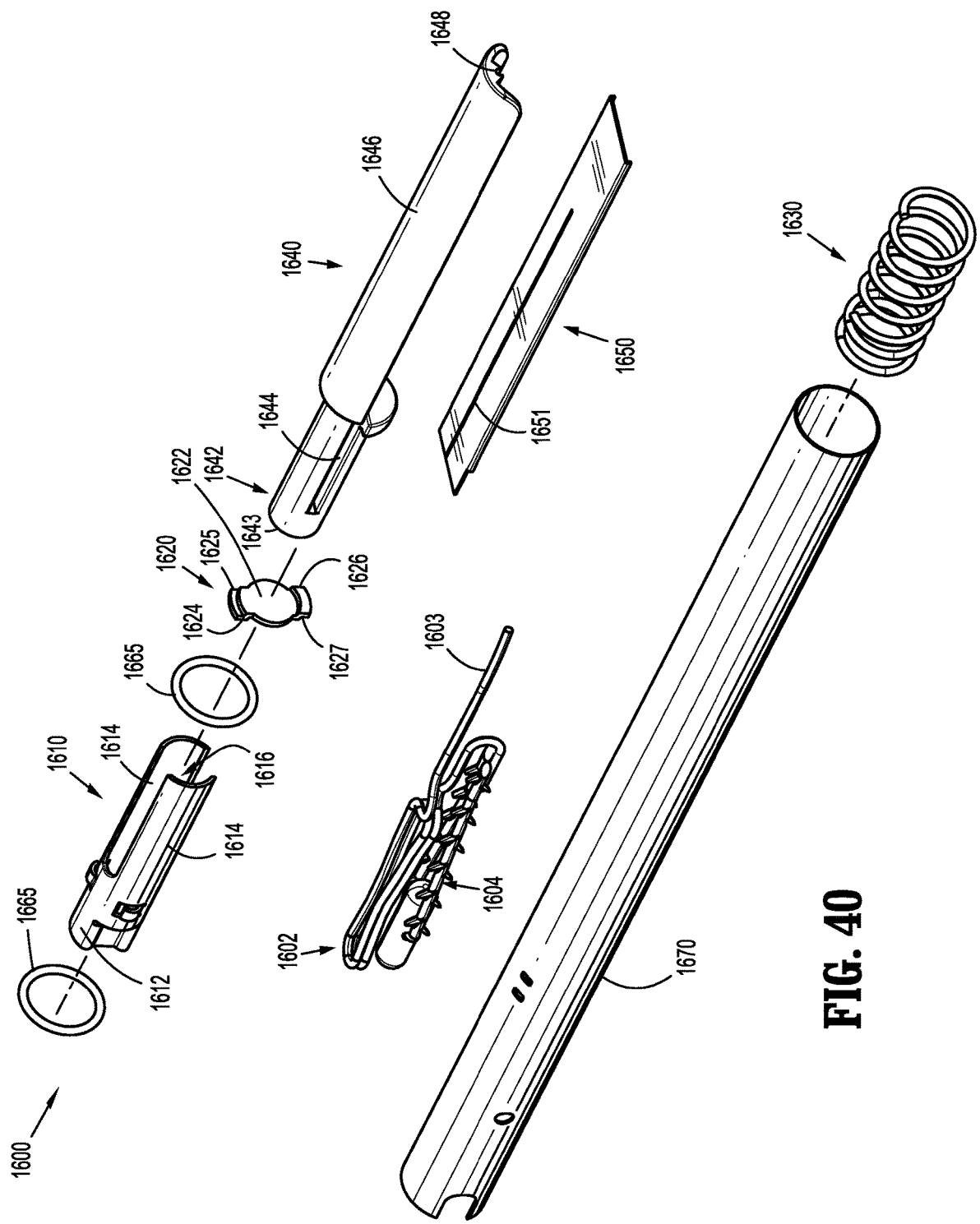
FIG. 40 is an assembly view of the end effector of FIGS. 38-39.

With particular reference to FIG. 40, end effector 1600 includes a drive assembly 1610, a drive plate 1620, a helix or coil assembly 1630, an ejector 1640, a divider 1650, a pair of rings 1665, and an outer tube 1670.

Drive assembly 1610 of end effector 1600 is mechanically engaged (e.g., operatively coupled, directly affixed, etc.) to drive rod 150 of surgical device 100 of the present disclosure. Drive assembly 1610 includes a body portion 1612, and a pair of arms 1614 extending distally from body portion 1612 and defining a cavity 1616 therebetween.

Drive plate 1620 of end effector 1600 includes a disc-like body 1622, a first flange 1624 extending radially outward from body 1622, and a second flange 1626 extending radially outward from body 1622. First flange 1624 of drive plate 1620 includes a distally-facing ledge 1625 configured for engaging helix or coil assembly 1630. Second flange 1626 of drive plate 1620 includes a proximally-facing ledge 1627 configured for engaging helix or coil assembly 1630 of end effector 1600. Body 1622 of drive plate 1620 is positioned within cavity 1616 of drive assembly 1610, and portions of first flange 1624 and second flange 1626 extend between arms 1614 of drive assembly 1610.

Helix or coil assembly 1630 of end effector 1600 is disposed radially within outer tube 1670, and radially outward of arms 1614 of drive assembly 1610. Helix or coil assembly 1630 is stationary with respect to outer tube 1670, and is configured to engage drive plate 1620, such that drive plate 1620 can move longitudinally and rotationally within outer tube 1670 and with respect to outer tube 1670.

Ejector 1640 of end effector 1600 is disposed within outer tube 1670 and is longitudinally translatable with respect to outer tube 1670. Ejector 1640 includes a proximal portion 1642 having a slit 1644 extending partially therethrough, and an arm 1646 extending from proximal portion 1642. A proximal face 1643 of proximal portion 1642 of ejector 1640 is positioned for engagement by drive plate 1620. It is envisioned that proximal face 1643 includes a finger extending proximally therefrom for engagement with a detent or aperture within a distal face of drive plate 1620. Arm 1646 of ejector 1640 is configured to help prevent suture 1603 disposed adjacent thereto from engaging outer tube 1670 and possibly getting stuck thereon. A distal end of arm 1646 includes a suture guide 1648 configured to help guide and/or position suture 1603.

Divider 1650 of end effector 1600 includes a longitudinal slot 1651 extending partially along a length of divider 1650. A proximal portion of divider 1650 is positioned within slit 1644 of ejector 1640. Divider 1650 is configured to create two cavities—a first cavity 1652 disposed between arm 1646 of ejector 1640 and divider 1650, and a second cavity 1654 disposed between outer tube 1670 and divider 1650 (see FIGS. 39 and 41). First cavity 1652 is configured to releasably house a portion (e.g. a majority) of suture 1603, and second cavity 1654 is configured to releasably house a barbed portion 1604 of barbed suture 1602 therein.

Rings 1665 (e.g., O-rings) of end effector 1600 are positioned radially outward of body portion 1612 of drive assembly 1610. Rings 1665 help maintain appropriate spacing between drive assembly 1610 and outer tube 1670, and help facilitate rotation of drive assembly 1610 with respect to outer tube 1670.

Outer tube 1670 of end effector 1600 is positioned radially outward of at least portions of barbed suture 1602, drive assembly 1610, drive plate 1620, helix or coil assembly 1630, ejector 1640, divider 1650, and rings 1665.

Figure 41:
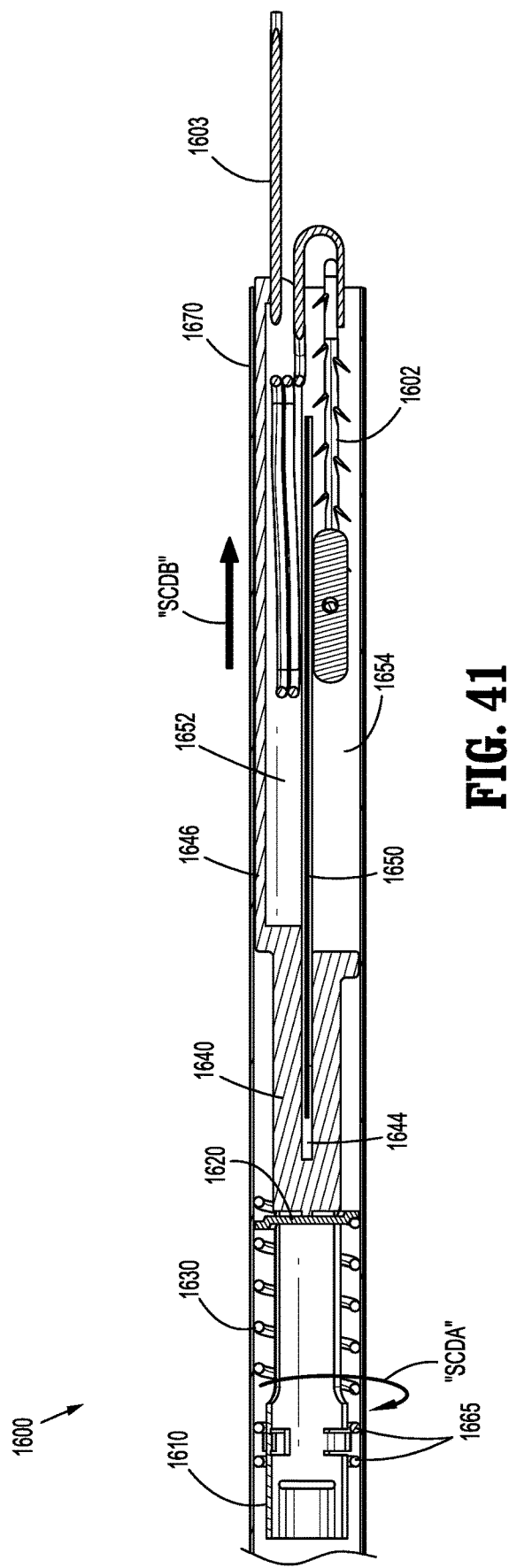
FIG. 41 is a cross-sectional view of the end effector of FIGS. 38-40 illustrating a portion of a suture in an advanced position.
Figure 42:
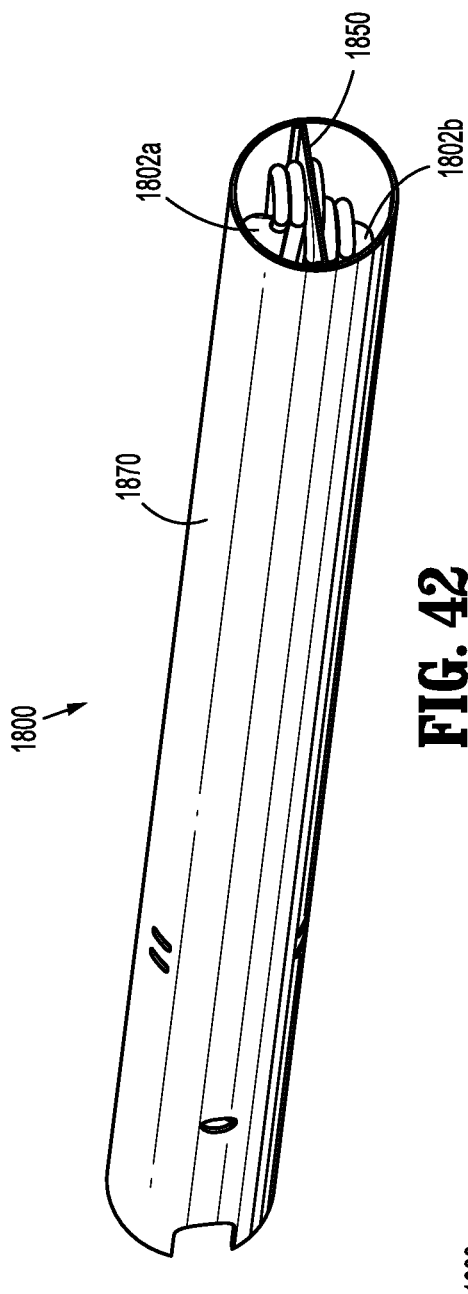
FIG. 42 is a perspective view of an end effector in accordance with embodiments of the present disclosure.
Figure 43:
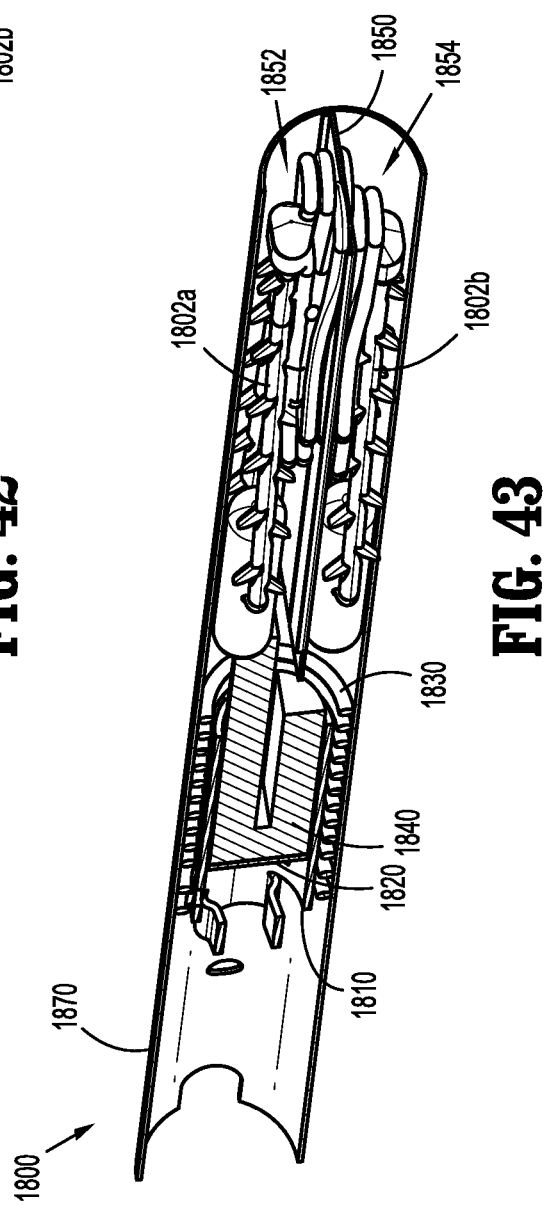
FIG. 43 is a cut-away view of a portion of the end effector of FIG. 42.

In use, in response to at least a partial actuation of the trigger of surgical device 100, drive rod 150 rotates, as discussed above. With reference to FIGS. 39 and 41, rotation of the drive rod 150 results in a corresponding rotation of drive assembly 1610 in the general direction of arrow "SCDA" (FIG. 41) with respect to outer tube 1670. Rotation of drive assembly 1610 results in a corresponding rotation of drive plate 1620 due to the engagement between arms 1614 of drive assembly 1610, and first flange 1624 and second flange 1626 of drive plate 1620. Further, the engagement between ledge 1625 of first flange 1624 and helix or coil assembly 1630, and between ledge 1627 of second flange 1626 and helix or coil assembly 1630, results in drive plate 1620 moving longitudinally in the general direction of arrow "SCDB" (FIG. 41) with respect to outer tube 1670. The distal longitudinal movement of drive plate 1620 causes a corresponding distal translation of ejector 1640 due to the engagement between drive plate 1620 and proximal face 1643 of ejector 1640. As ejector 1640 translates distally, a portion of suture 1603 is moved distally beyond a distal end of outer tube 1670 and is thus graspable by a user. As noted above, end effector 1600 is configured for use with a separate instrument (e.g., a needle suture passer) to drive and/or implant suture 1603 in tissue.

Two Cartridge Design

Referring now to FIGS. 42-48, an embodiment of an end effector 1800 is shown. End effector 1800 includes two barbed sutures 1802a, 1802b at least partially therein, and is configured for use in connection with surgical device 100. Additionally, end effector 1800 is configured for use with a separate instrument (e.g., a needle suture passer) to drive and/or implant the sutures in tissue. Generally, end effector 1800 is configured to advance barbed sutures 1802a, 1802b distally, such that portions of a suture 1803a, 1803b of barbed sutures 1802a, 1802b, respectively, are graspable by a user. While FIGS. 42-48 illustrate a particular type of barbed suture 1802a, 1802b, end effector 1800 may be used with different types of sutures.

Figure 44:
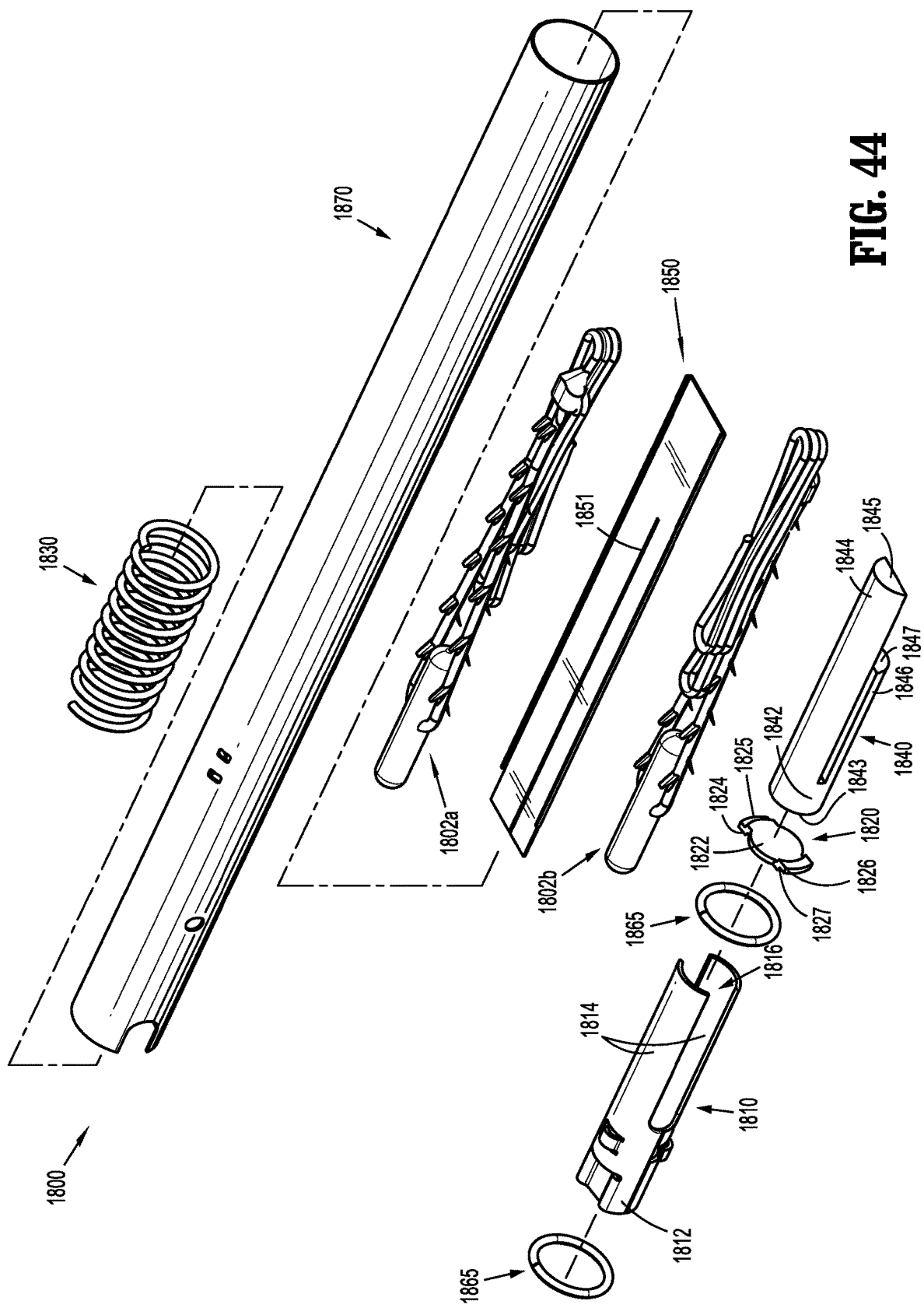
FIG. 44 is an assembly view of the end effector of FIGS. 42-43.
Figure 45:
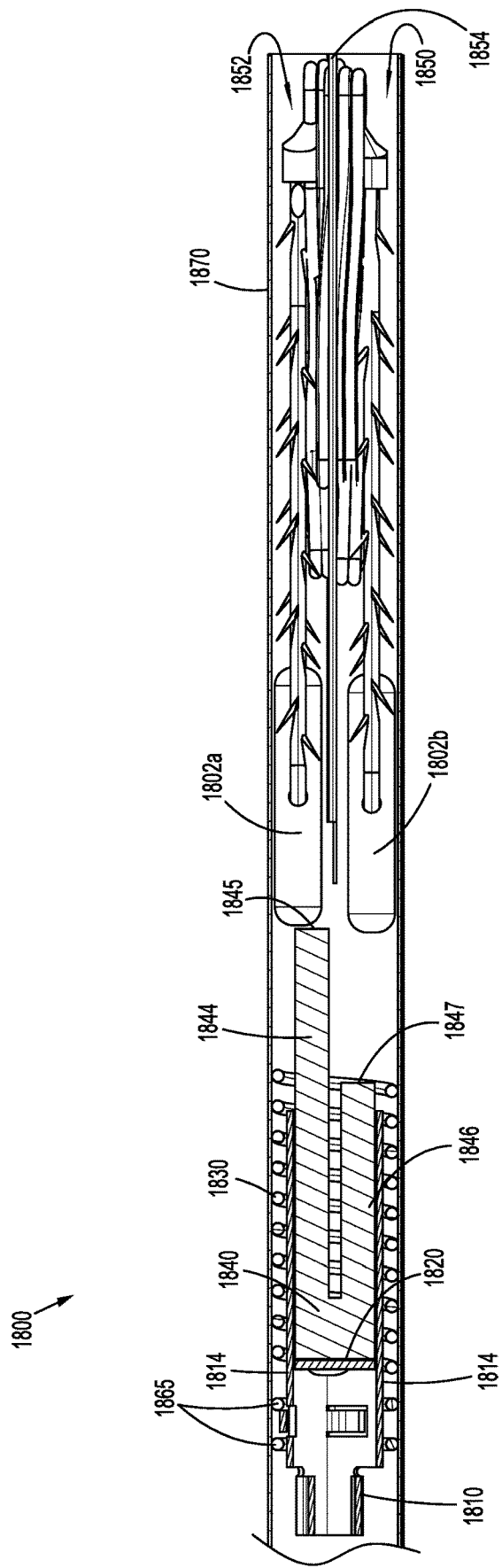
FIG. 45 is a cross-sectional view of the end effector of FIGS. 42-44.

With particular reference to FIG. 44, end effector 1800 includes a drive assembly 1810, a drive plate 1820, a helix or coil assembly 1830, an ejector 1840, a divider 1850, a pair of rings 1865, and an outer tube 1870.

Drive assembly 1810 of end effector 1800 is mechanically engaged (e.g., operatively coupled, directly affixed, etc.) to drive rod 150 of surgical device 100 of the present disclosure. Drive assembly 1810 includes a body portion 1812, and a pair of arms 1814 extending distally from body portion 1812 and defining a cavity 1816 therebetween.

Drive plate 1820 of end effector 1800 includes a disc-like body 1822, a first flange 1824 extending radially outward from body 1822, and a second flange 1826 extending radially outward from body 1822. First flange 1824 of drive plate 1820 includes a distally-facing ledge 1825 configured for engaging helix or coil assembly 1830. Second flange 1826 of drive plate 1820 includes a proximally-facing ledge 1827 configured for engaging helix or coil assembly 1830. Body 1822 of drive plate 1820 is positioned within cavity 1816 of drive assembly 1810, and portions of first flange 1824 and second flange 1826 extend between arms 1814 of drive assembly 1810.

Helix or coil assembly 1830 of end effector 1800 is disposed radially within outer tube 1870, and radially outward of arms 1814 of drive assembly 1810. Helix or coil assembly 1830 is stationary with respect to outer tube 1870, and is configured to engage drive plate 1820, such that drive plate 1820 can move longitudinally and rotationally within outer tube 1870 and with respect to outer tube 1870.

Ejector 1840 of end effector 1800 is disposed within outer tube 1870 and is longitudinally translatable with respect to outer tube 1870. Ejector 1840 includes a proximal portion 1842, a first arm 1844 extending distally from proximal portion 1842, and a second arm 1846 extending distally from proximal portion 1842. First arm 1844 of ejector 1840 extends farther distally than second arm 1846. A proximal face 1843 of proximal portion 1842 of ejector 1840 is positioned for engagement by drive plate 1820. It is envisioned that proximal face 1843 includes a finger extending proximally therefrom for engagement with a detent or aperture within a distal face of drive plate 1820. A distal face 1845 of first arm 1844 of ejector 1840 is configured to move into engagement with a proximal portion of barbed suture 1802a, and a distal face 1847 of second arm 1846 is configured to move into engagement with a proximal portion of barbed suture 1802b.

Divider 1850 of end effector 1800 includes a longitudinal slot 1851 extending partially along a length of divider 1850. Divider 1850 is positioned within a distal portion of outer tube 1870, and is frictionally engaged with outer tube 1870, which prevents or minimizes movement of divider 1850 with respect to outer tube 1870. Divider 1850 is configured to create two cavities—a first cavity 1852 disposed distally of first arm 1844 of ejector 1840 and between divider 1850 and outer tube 1870, and a second cavity 1854 disposed distally of second arm 1846 of ejector 1840 and between divider 1850 and outer tube 1870 (see FIGS. 43 and 45). First cavity 1852 of divider 1850 is configured to releasably house barbed suture 1802a therein, and second cavity 1854 of divider 1850 is configured to releasably house barbed suture 1802b therein.

Rings 1865 (e.g., O-rings) of end effector 1800 are positioned radially outward of body portion 1812 of drive assembly 1810. Rings 1865 help maintain appropriate spacing between drive assembly 1810 and outer tube 1870, and help facilitate rotation of drive assembly 1810 with respect to outer tube 1870.

Outer tube 1870 of end effector 1800 is positioned radially outward of at least portions of barbed sutures 1802a, 1802b, drive assembly 1810, drive plate 1820, helix or coil assembly 1830, ejector 1840, divider 1850, and rings 1865.

Figure 48:
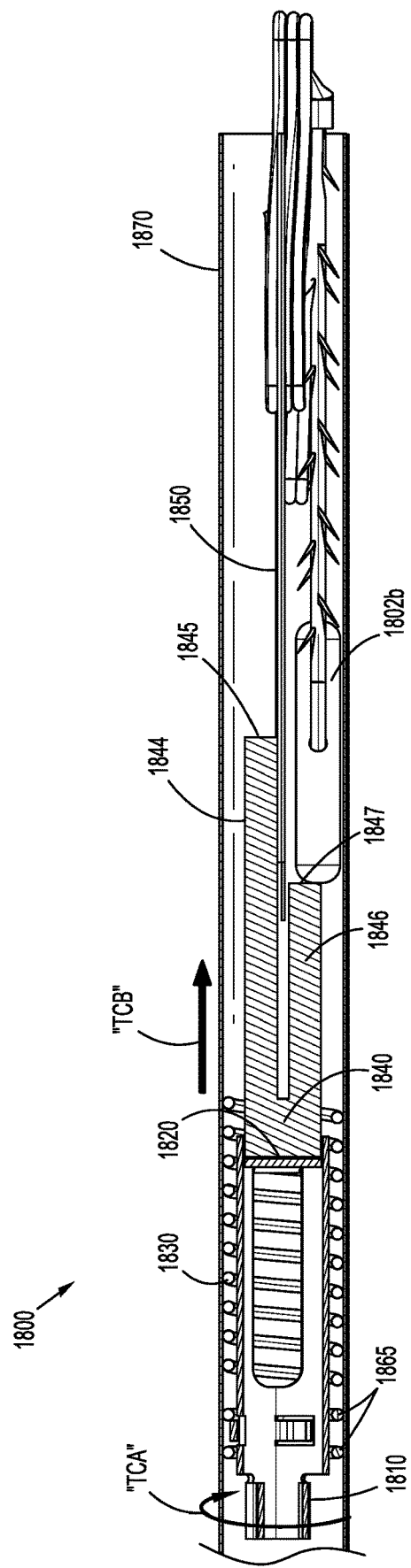
FIG. 48 is a cross-sectional view of the end effector of FIGS. 42-47 illustrating a portion of a second barbed suture in an advanced position.

In use, in response to at least a partial actuation of the trigger (e.g., a first complete actuation) of surgical device 100, drive rod 150 rotates, as discussed above. With reference to FIGS. 46-48, rotation of the drive rod 150 results in a corresponding rotation of drive assembly 1810 in the general direction of arrow "TCA" (FIG. 46) with respect to outer tube 1870. Rotation of drive assembly 1810 results in a corresponding rotation of drive plate 1820 due to the engagement between arms 1814 of drive assembly 1810, and first flange 1824 and second flange 1826 of drive plate 1820. Further, the engagement between ledge 1825 of first flange 1824 and helix or coil assembly 1830, and between ledge 1827 of second flange 1826 and helix or coil assembly 1830, results in drive plate 1820 moving longitudinally in the general direction of arrow "TCB" (FIG. 46) with respect to outer tube 1870. The distal longitudinal movement of drive plate 1820 causes a corresponding distal translation of ejector 1840 due to the engagement between drive plate 1820 and proximal face 1843 of ejector 1840. As ejector 1840 translates distally, ejector 1840 pushes barbed suture 1802a distally such that a portion of suture 1803a is moved distally beyond a distal end of outer tube 1870 and is thus graspable by a user (see FIGS. 46 and 47).

In response to an additional actuation of the trigger (e.g., a second complete actuation) of surgical device 100, drive rod 150 rotates again. Rotation of the drive rod 150 results in an additional rotation of drive assembly 1810 in the general direction of arrow "TCA," a corresponding rotation of drive plate 1820, distal longitudinal movement of drive plate 1820, and a corresponding distal longitudinal movement of ejector 1840 in the general direction of "TCB" (FIG. 48). As ejector 1840 moves distally, ejector 1840 pushes barbed suture 1802b such that a portion of suture 1803b is moved distally beyond a distal end of outer tube 1870 and is thus graspable by a user (see FIG. 48). As noted above, end effector 1800 is configured for use with a separate instrument (e.g., a needle suture passer) to drive and/or implant sutures 1803a, 1803b in tissue.

Double Helix Barrel Cam

Referring now to FIGS. 49-53, an embodiment of an end effector 1900 is shown. End effector 1900 includes a barbed suture 1902 and a needle 1906 at least partially therein, and is configured for use in connection with surgical device 100. Generally, end effector 1900 is configured to advance needle 1906 and to eject barbed suture 1902 towards tissue. While FIGS. 49-53 illustrate a particular type of barbed suture 1902 and needle 1906, end effector 1900 may be used with different types of sutures and needles.

Figure 50:
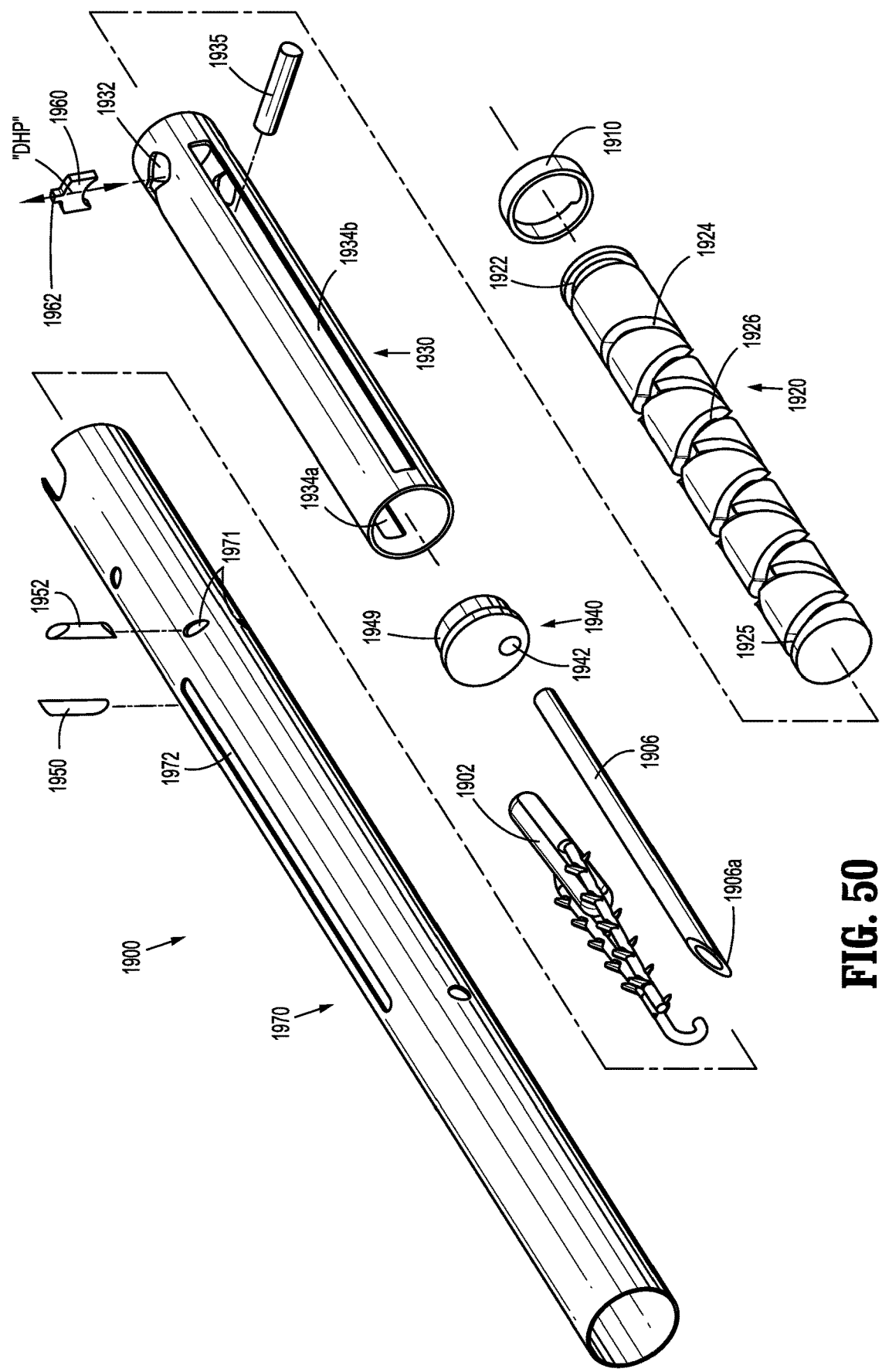
FIG. 50 is an assembly view of the end effector of FIG. 49.
Figure 51:
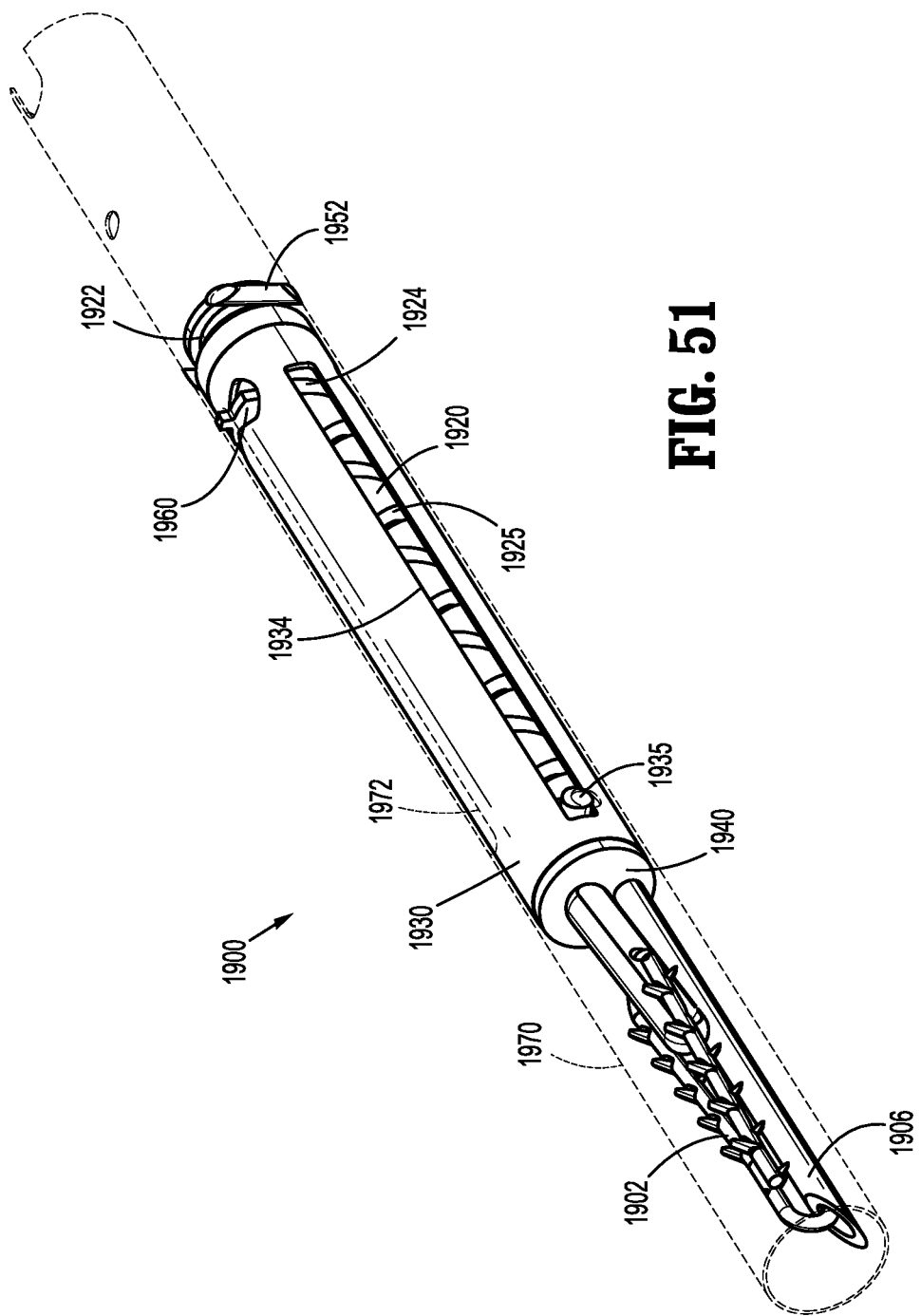
FIG. 51 is a perspective view of portions of the end effector of FIGS. 49-50.

With particular reference to FIG. 50, end effector 1900 includes a drive ring 1910, a drive assembly or drive shaft 1920, a driver 1930, a needle assembly or cap 1940, and an outer tube 1970.

Drive ring 1910 of end effector 1900 is mechanically engaged (e.g., operatively coupled, directly affixed, etc.) to drive rod 150 of surgical device 100 of the present disclosure. Drive ring 1910 is ring-like and is configured to non-rotationally engage a proximal portion of drive shaft 1920, such that rotation of drive ring 1910 causes a corresponding rotation of drive shaft 1920.

Drive shaft 1920 of end effector 1900 includes an elongated cylindrical body portion and is disposed in mechanical engagement with drive ring 1910. Drive shaft 1920 includes a proximal groove 1922, a first helical groove 1924 and a second helical groove 1926. First helical groove 1924 and second helical groove 1926 encircle at least a portion of drive shaft 1920, and are interconnected at their proximal ends and their distal ends. Proximal groove 1922 is configured to rotatably engage a first pin 1950 and a second pin 1952, such that drive shaft 1920 is rotatable with respect to first pin 1950 and second pin 1952. Drive shaft 1920 is fixed from longitudinal movement with respect to first pin 1950 and second pin 1952. As discussed below, first pin 1950 and second pin 1952 extend at least partially through apertures 1971 in outer tube 1970. Accordingly, drive shaft 1920 is fixed from longitudinal movement with respect to outer tube 1970. First helical groove 1924 and second helical groove 1926 of drive shaft 1920 are each configured to rotatably engage a follower 1960. More particularly, follower 1960 engages or fits at least partially within a portion of first helical groove 1924 to cause follower 1960 to move distally with respect to drive shaft 1920 when drive shaft 1920 rotates in a first direction (e.g., upon initial actuation of a trigger). Further, follower 1960 engages or fits at least partially within a portion of second helical groove 1926 to cause follower 1960 to move proximally with respect to drive shaft 1920 when drive shaft 1920 rotates in a second direction (e.g., upon a subsequent actuation of the trigger).

Figure 52:
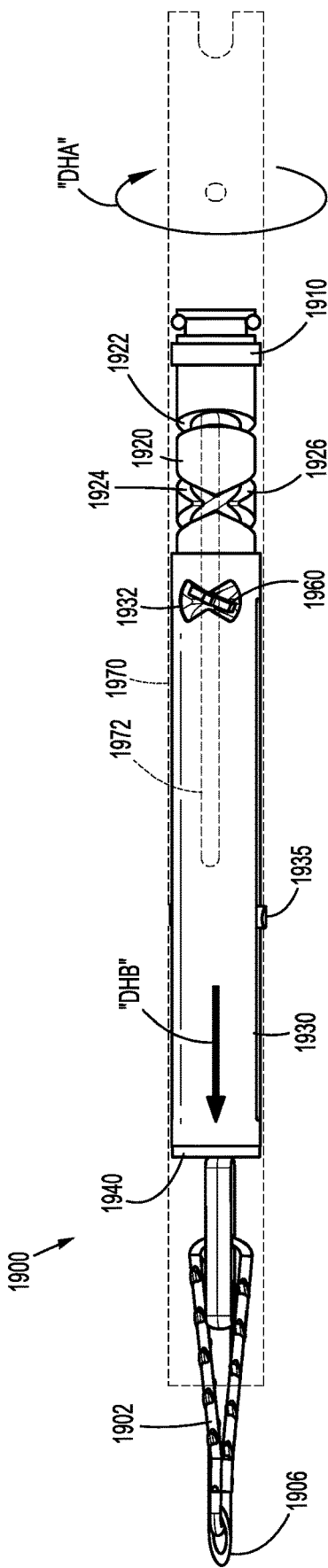
FIG. 52 is a side view of the end effector of FIGS. 49-51 illustrating a follower moving distally.
Figure 53:
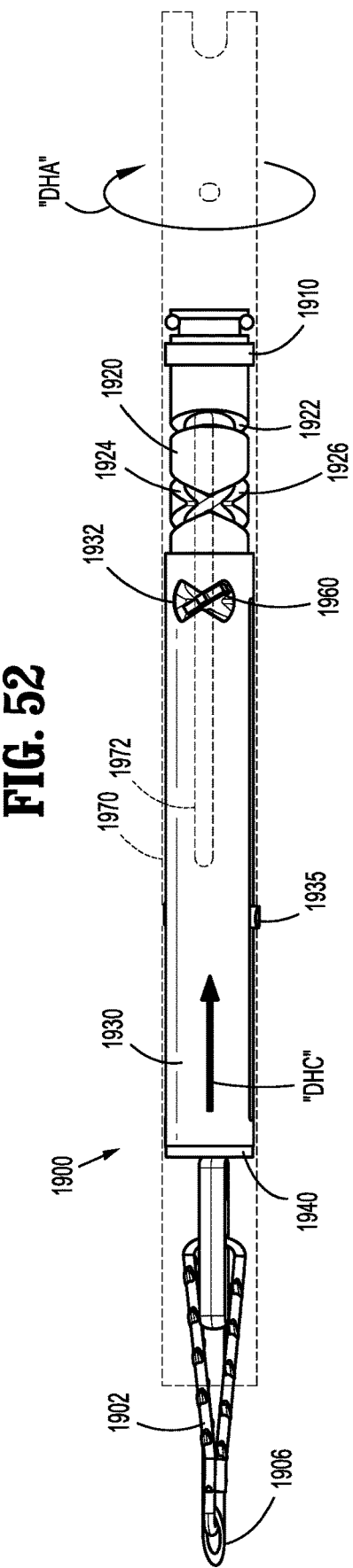
FIG. 53 is a side view of the end effector of FIGS. 49-52 illustrating the follower moving proximally.

Driver 1930 of end effector 1900 is a hollow cylinder and is configured to be positioned radially outward of at least portions of drive shaft 1920. Driver 1930 includes a proximal aperture 1932, and a pair of longitudinal slots 1934 extending along a majority of a length of driver 1930. Proximal aperture 1932 of driver 1930 is configured to allow follower 1960 to pass at least partially therethrough. Additionally, as shown in FIGS. 52 and 53, proximal aperture 1932 is generally bow-tie shaped, which allows follower 1960 to rotate about an axis "DHP" defined therethrough, with respect to aperture 1932. Longitudinal slots 1934 are configured to allow a third pin 1935 to pass therethrough, such that third pin 1935 extends from a first longitudinal slot 1934a, through the hollow center of driver 1930, and through a second longitudinal slot 1934b. Third pin 1935 is positioned distally of drive shaft 1920.

Cap 1940 of end effector 1900 is configured to engage (e.g., is affixed to) a distal end of driver 1930 and is configured to engage (e.g., is affixed to) a proximal end of needle 1906. Cap 1940 includes a needle-securing portion 1942 to help engage needle 1906. Needle-securing portion 1942 of cap 1940 is offset from a radial center of cap 1940. Additionally, cap 1940 includes a proximal flange 1944, which is configured to fit radially within driver 1930, to help secure the connection therebetween.

Outer tube 1970 of end effector 1900 is positioned radially outward of at least portions of barbed suture 1902, needle 1906, drive ring 1910, drive shaft 1920, driver 1930, and cap 1940. Outer tube 1970 includes a longitudinal slot 1972 extending along a portion of its length. Longitudinal slot 1972 of outer tube 1970 is configured to allow a pin portion 1962 of follower 1960 to extend therethrough, which allows follower 1960 and driver 1930 to longitudinally translate with respect to outer tube 1970.

Figure 49:
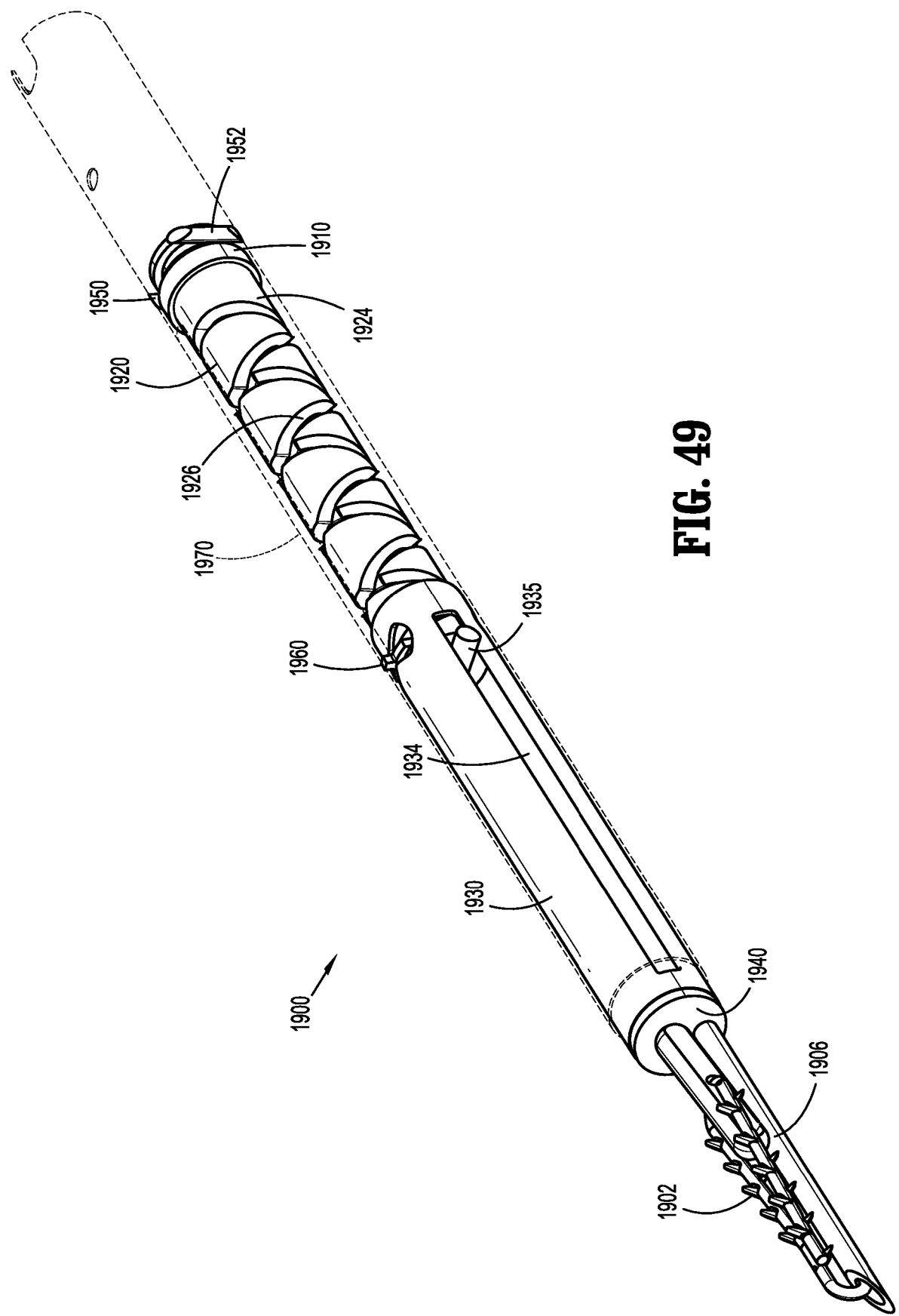
FIG. 49 is a perspective view of an end effector in accordance with embodiments of the present disclosure.

In use, in response to at least a partial actuation of the trigger of surgical device 100, drive rod 150 rotates, as discussed above. With reference to FIGS. 49-50, rotation of the drive rod 150 results in a corresponding rotation of drive ring 1910 in the general direction of arrow "DHA" (FIG. 52) with respect to outer tube 1970. Rotation of drive ring 1910 results in a corresponding rotation of drive shaft 1920 due to the engagement therebetween. The engagement between proximal groove 1922 of drive shaft 1920 with first pin 1950 and second pin 1952 facilitates rotation of drive shaft 1920 with respect to outer tube 1970, and restricts drive shaft 1920 from moving longitudinally with respect to outer tube 1970.

Further, the engagement between follower 1960 and first helical groove 1924 of drive shaft 1920 causes follower 1960 to move distally in the general direction of arrow "DHB" in response to rotation of drive ring 1910 in the general direction of arrow "DHA." The engagement between pin portion 1962 of follower 1960 and longitudinal slot 1972 of outer tube 1970 allows follower 1960 to move longitudinally with respect to outer tube 1970, and restricts follower 1960 from moving rotationally with respect to outer tube 1970.

Additionally, the distal translation of follower 1960 causes a corresponding distal translation of driver 1930 with respect to outer rube 1970 due to the engagement between follower 1960 and driver 1930. The engagement between third pin 1935 and longitudinal slots 1934 of driver 1930 help guide the longitudinal travel of driver 1930 with respect to outer tube 1970. As driver 1930 translates distally, cap 1940, needle 1906 and barbed suture 1902 are pushed distally with respect to outer tube 1970. As needle 1906 travels distally, a distal portion of needle 1906 (e.g., a distal tip 1906a) and barbed suture 1902 distally exit outer tube 1970, and engages tissue/mesh, for instance.

When drive shaft 1920 has rotated a predetermined amount, follower 1960 continues its movement within first helical groove 1924, and moves into a transition portion 1925 (FIG. 50), which interconnects first helical groove 1924 and second helical groove 1926. Continued rotation of drive shaft 1920 causes follower 1960 to move from transition portion 1925 and into second helical groove 1926. The movement of follower 1960 from first helical groove 1924, into transition portion 1925, and into second helical groove 1926 causes follower 1960 to rotate or pivot about axis "DHP" which extends through pin portion 1962, and which is perpendicular to longitudinal axis "DHA," such that follower 1960 aligns with second helical groove 1926.

In response to continued actuation or an additional actuation of the trigger of surgical device 100, drive ring 1910 and drive shaft 1920 continue to rotate in the general direction of arrow "DHA." Due to the engagement between follower 1960 and second helical groove 1926, the rotation of drive shaft 1920 causes follower 1960 to move proximally in the general direction of arrow "DHC" (FIG. 53). Proximal movement of follower 1960 results in a corresponding proximal movement of driver 1930, and thus proximal movement of needle 1906. Needle 1906 is movable proximally until its distal tip 1906*a* is longitudinally aligned with or proximal of a distal end of outer tube 1970, thereby reducing the possibility of a user unintentionally contacting needle 1906.

It is envisioned that one complete actuation of the trigger of surgical device 100 causes drive shaft 1920 to rotate a particular number of times (e.g., five) corresponding to follower 1960 and driver 1930 moving from their proximal-most positions to their distal-most positions (corresponding to the first two and one half rotations), and back to their proximal-most positions (corresponding to the second two and one half rotations). It is also envisioned that one complete actuation of the trigger of surgical device 100 causes drive shaft 1920 to rotate a particular number of time (e.g., five) corresponding to follower 1960 and driver 1930 moving from their proximal-most positions to their distal-most positions, and that a second complete actuation of the trigger of surgical device 100 causes drive shaft 1920 to rotate a particular number of time (e.g., five) corresponding to follower 1960 and driver 1930 moving from their distal-most positions to their proximal-most positions.

Reversible Thread Pitch

Referring now to FIGS. 54-64, an embodiment of an end effector 2200 is shown. End effector 2200 is configured for use in connection with surgical device 100. Generally, end effector 2200 is configured to advance a needle 2206 towards tissue and to eject a barbed suture 2202 towards tissue. While FIGS. 54-64 illustrate a particular type of barbed suture 2202 and a particular type of needle 2206, end effector 2200 may be used with different types of sutures and/or needles.

Figure 56:
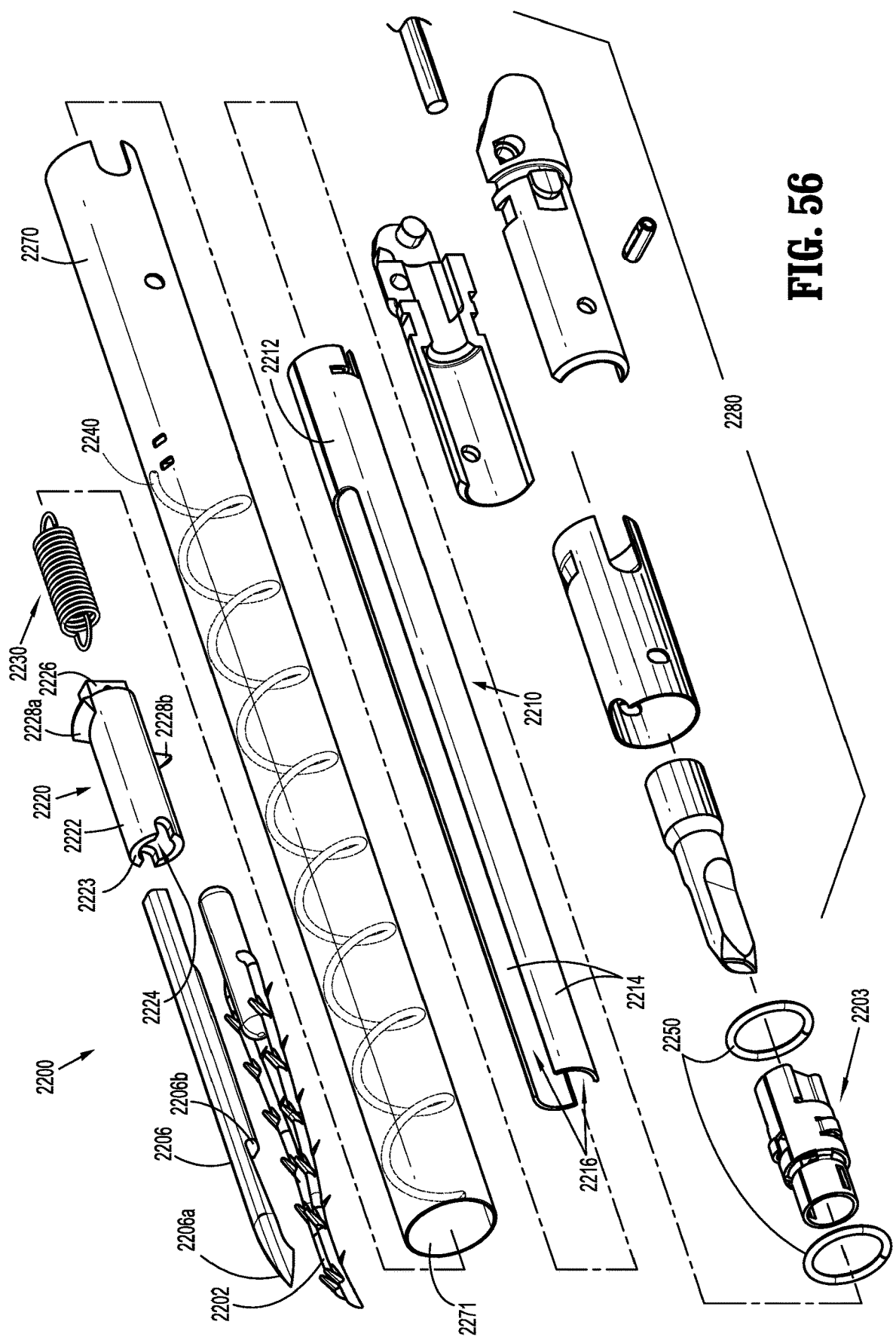
FIG. 56 is an assembly view of the end effector of FIGS. 54-55.
Figure 65:
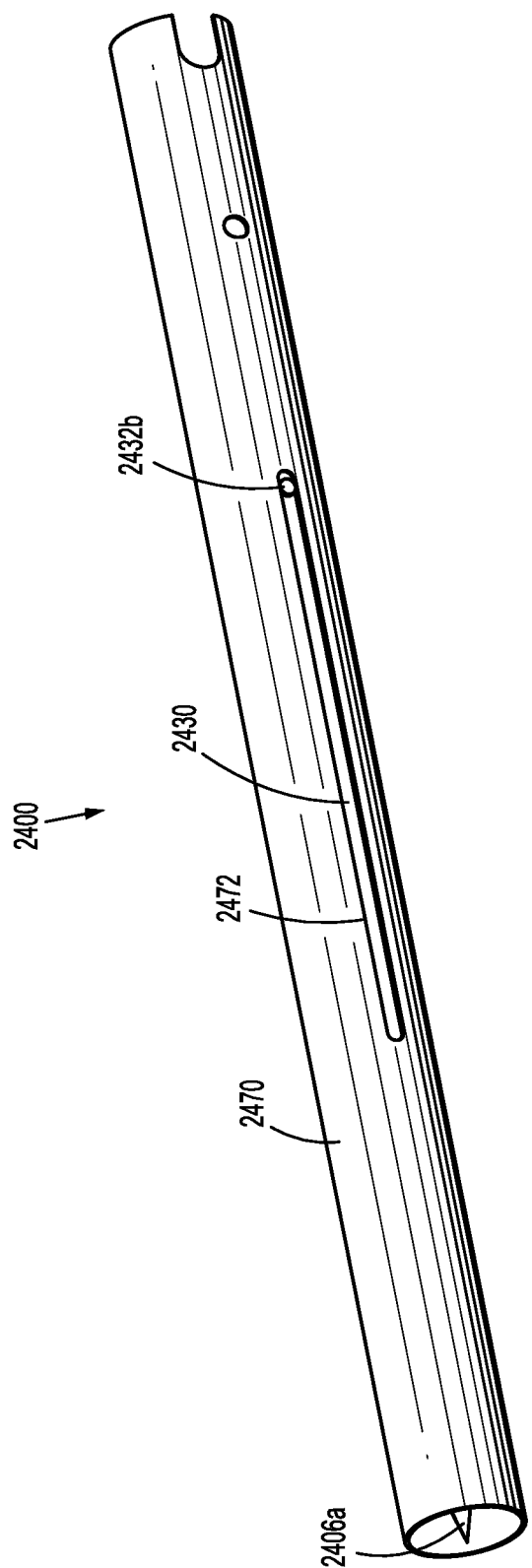
FIG. 65 is a perspective view of an end effector in accordance with embodiments of the present disclosure.

With particular reference to FIG. 56, end effector 2200 includes an activation sleeve 2203, a drive assembly 2210, a driver 2220, a retraction spring 2230, a helix or coil assembly 2240, a pair of rings 2250, and an outer tube 2270.

Activation sleeve 2203 of end effector 2200 is mechanically engaged (e.g., operatively coupled, directly affixed, etc.) to a drive rod assembly 2280 of the handle assembly of the surgical device 100 of the present disclosure. Rotation of drive rod assembly 2280 in the general direction of arrow "RTA" in FIG. 56 results in a corresponding rotation of activation sleeve 2203.

Drive assembly 2210 of end effector 2200 is mechanically and selectively engaged with activation sleeve 2203, as discussed in further detail below. When engaged, rotation of activation sleeve 2203 in the general direction of arrow "RTA" results in a corresponding rotation of drive assembly 2210. Drive assembly 2210 includes a body portion 2212 and a pair of arms 2214 extending therefrom. Arms 2214 of drive assembly 2210 define a pair of slots 2216 therebetween. Slots 2216 of arms 2214 are configured to slidingly receive portions of driver 2220 of end effector 2200.

Needle 2206 includes a distal tip 2206*a* and a hook 2206*b*. Distal tip 2206*a* of needle 2206 is configured to pierce tissue, and hook 2206*b* is configured to engage a portion of barbed suture 2202.

Driver 2220 of end effector 2200 includes a body portion 2222 defining a cavity 2224 therein, a proximal portion 2226, and a threaded portion 2228 including at least one thread. A distal end 2223 of body portion 2222 of driver 2220 is configured to contact a proximal portion of needle 2206. Cavity 2224 of driver 2220 is configured to releasably house a portion of barbed suture 2002 therein. Proximal portion 2226 of driver 2220 is configured to engage a distal portion of retraction spring 2230. A first thread 2228*a* and a second thread 2228*b* of threaded portion 2228 of driver 2220 are configured to extend through respective slots 2216 of drive assembly 2210 to engage helix or coil assembly 2240, which extends radially inward from an inner wall 2271 of outer tube 2270.

A distal portion of retraction spring 2230 of end effector 2200 is engaged with proximal portion 2226 of driver 2220, and a proximal portion of retraction spring 2230 is engaged with a portion of activation sleeve 2203. Retraction spring 2230 is configured to bias driver 2220 proximally.

Helix or coil assembly 2240 of end effector 2200 extends radially inward from inner wall 2271 of outer tube 2270, and is stationary with respect to outer tube 2270. Helix or coil assembly 2240 is configured to engage thread portion 2228 of driver 2220 such that driver 2220 can move longitudinally and rotationally within outer tube 2270 and with respect to outer tube 2270.

Rings 2250 (e.g., O-rings) of end effector 2200 are positioned radially outward of portions of activation sleeve 2230. Rings 2250 help maintain appropriate spacing between activation sleeve 2230 and outer tube 2270, and help facilitate rotation of activation sleeve 2230 with respect to outer tube 2270.

Outer tube 2270 of end effector 2200 is configured for positioning radially outward of at least portions of barbed suture 2202, needle 2206, activation sleeve 2203, drive assembly 2210, driver 2220, retraction spring 2230 and rings 2250.

End effector 2200 also includes a ratchet mechanism 2290. Ratchet mechanism 2290 includes a pair of tabs 2292*a*, 2292*b*, which extend radially inwardly from a proximal portion of drive assembly 2210, and a pair of engagement features 2294*a*, 2294*b* disposed on activation sleeve 2203. Tabs 2292*a*, 2292*b* of ratchet mechanism 2290 are configured to selectively engage engagement features 2294*a*, 2294*b*, respectively, as discussed in further detail below.

In use, in response to at least a partial actuation of the trigger of surgical device 100, drive rod 150 rotates, as discussed above. With reference to FIGS. 59-60, initial rotation of the drive rod 150 results in a corresponding rotation of activation sleeve 2203, drive assembly 2210 and driver 2220 with respect to outer tube 2270 in the general direction of arrow "RTA" in FIGS. 59 and 60. With reference to FIG. 58, the engagement between tabs 2210*a* of drive assembly 2210 and recesses 2203*a* of activation sleeve 2203 causes rotation of drive assembly 2210 in the direction of arrow "RTA" in response to rotation of activation sleeve 2203 in the direction of arrow "RTA."

Further, the engagement between arms 2214 of drive assembly 2210 and threaded portion 2228 of driver 2220 causes rotation of driver 2220 in the direction of arrow "RTA" in response to rotation of drive assembly 2210 in the direction of arrow "RTA." The rotation of driver 2220 in the direction of arrow "RTA" causes at least a distal portion of retraction spring 2230 to rotate or wind in a corresponding fashion due to the engagement between the distal portion of retraction spring 2230 and driver 2220.

Additionally, due to the engagement between helix or coil assembly 2240 and threaded portion 2228 of driver 2220, rotation of driver 2220 in the general direction of arrow "RTA" results in distal translation of driver 2200 with respect to outer tube 2270 in the general direction of arrow "RTB" in FIGS. 59 and 60. Distal translation of driver 2220 causes a corresponding distal translation of needle 2206. Further, distal translation of driver 2220 also causes a corresponding distal translation of barbed suture 2202 due to the engagement between barbed suture 2202 and distal end 2223 of driver 2220 and/or between barbed suture 2202 and needle 2206.

With reference to FIGS. 61 and 62 continued rotation of drive assembly 2210 in the general direction of arrow "RTA" causes continued distal advancement of driver 2220 and needle 2206 until distal tip 2206a of needle 2206 extends a sufficient distance distally beyond a distal end of outer tube 2270. Thus, to insert needle 2206 and/or barbed suture 2202 into tissue, a distal end of end effector 2200 is positioned adjacent or in contact with tissue, and the trigger of surgical device 100 is at least partially actuated, thus distally advancing a portion of needle 2206 and/or barbed suture 2202 into tissue.

With particular reference to FIGS. 63 and 64, after a predetermined amount of rotation of drive assembly 2210 and distal travel of needle 2206 (e.g., corresponding to when distal tip 2206a is sufficiently advanced within tissue), threaded portion 2228 of driver 2220 are advanced distally beyond helix or coil assembly 2240. In this position, and when the force applied to the trigger of surgical device 100 is released and thus the force maintaining retraction spring 2230 in its rotation and longitudinal position is removed or decreased, retraction spring 2230 unwinds in the direction of arrow "RTC" in FIGS. 58, 63 and 64, thus causing driver 2220 to rotate in the same direction (e.g., due to the engagement between threaded portion 2228 and helix or coil assembly 2240) and move proximally in the direction of arrow "RTD" in FIGS. 63 and 64. The rotation of driver 2220 in the direction of arrow "RTC" causes a corresponding rotation of driver assembly 2210, which results in tabs 2210a thereof disengaging from recesses 2203a activation sleeve 2203 (FIG. 58), and which allows activation sleeve 2203 to return to its original position with respect to drive assembly 2210.

Reciprocating Lead Screw

Referring now to FIGS. 65-71, an embodiment of an end effector 2400 is shown. End effector 2400 includes a barbed suture 2402 and a needle 2406 at least partially therein, and is configured for use in connection with surgical device 100. Generally, end effector 2400 is configured to advance needle 2406 and to eject barbed suture 2402 towards tissue. While FIGS. 65-71 illustrate a particular type of barbed suture 2402 and needle 2406, end effector 2400 may be used with different types of sutures and needles.

Figure 66:
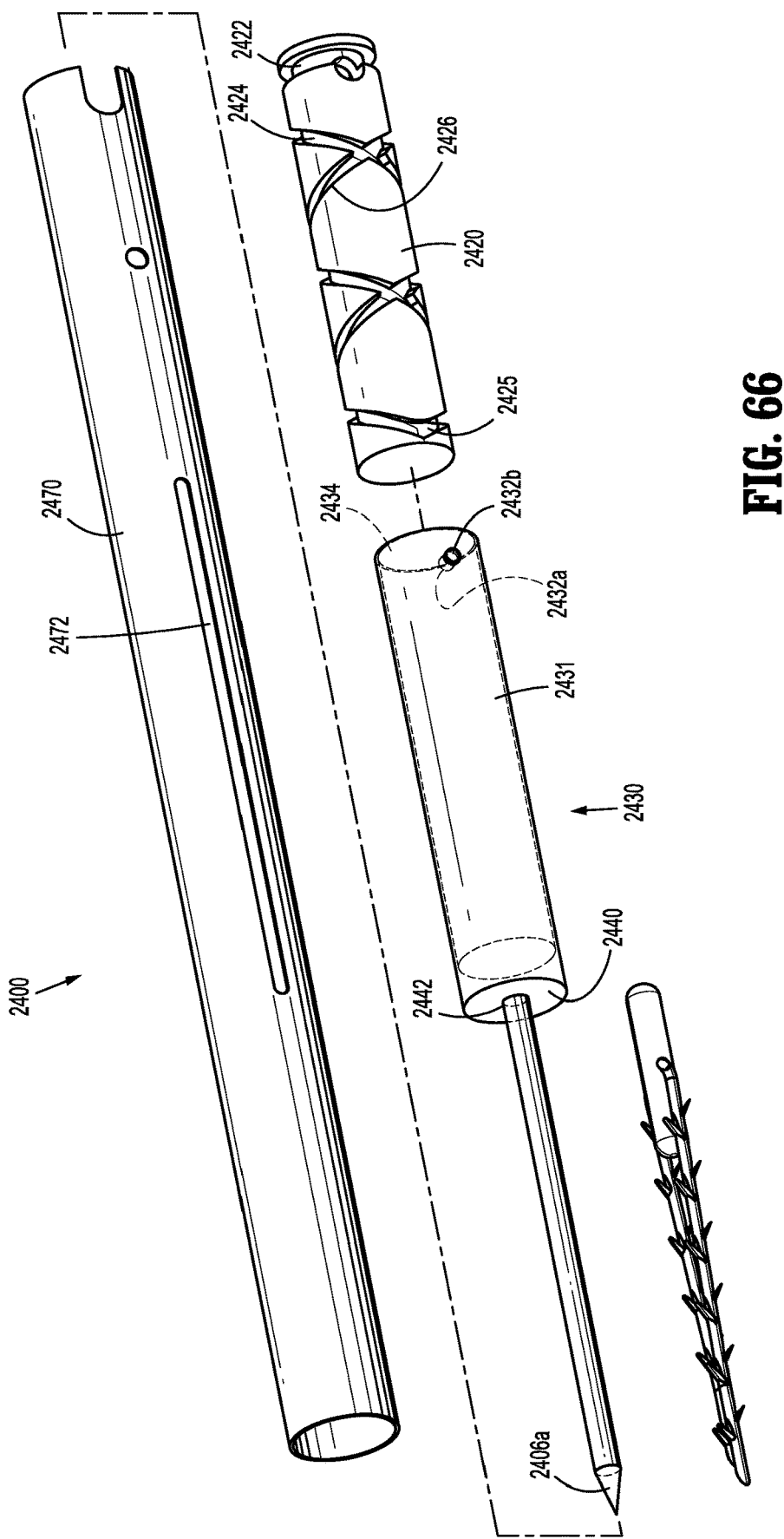
FIG. 66 is an assembly view of the end effector of FIG. 65.
Figure 67:
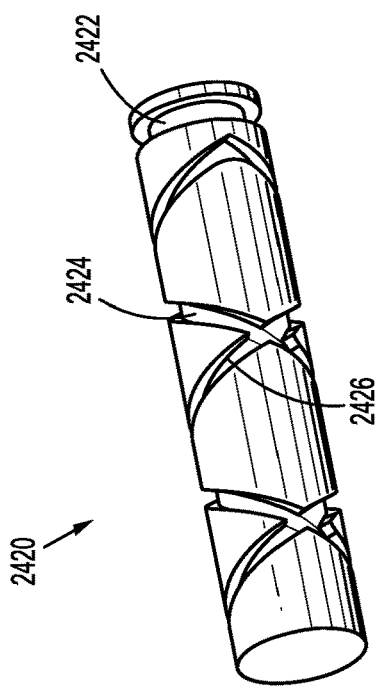
FIG. 67 is a perspective view of a portion of a drive shaft of the end effector of FIGS. 65-66.

With particular reference to FIG. 66, end effector 2400 includes a drive shaft 2420, a driver 2430, a cap 2440, and an outer tube 2470.

Drive shaft 2420 of end effector 2400 is mechanically engaged (e.g., operatively coupled, directly affixed, etc.) to drive rod 150 of surgical device 100 of the present disclosure. Drive shaft 2420 is an elongated cylinder and includes a proximal groove 2422, a first helical groove 2424 and a second helical groove 2426. Proximal groove 2422 of drive shaft 2420 is configured to rotatably engage at least one pin (not explicitly shown) that extends at least partially through outer tube 2470, such that drive shaft 2420 is rotatable with respect to outer tube 2470 and drive shaft 2420 is fixed from longitudinal movement with respect to outer tube 2470. First helical groove 2424 and second helical groove 2426 of drive shaft 2420 are each configured to rotatably engage a first portion 2432a of a follower 2432 of driver 2430. More particularly, first portion 2432a of follower 2432 engages or fits at least partially within a portion of first helical groove 2424 to cause follower 2432 to move distally with respect to drive shaft 2420 when drive shaft 2420 rotates in the general direction of arrow "RLA" in FIG. 68 (e.g., upon initial actuation of a trigger). Further, first portion 2432a of follower 2432 engages or fits at least partially within a portion of second helical groove 2426 to cause follower 2432 to move proximally with respect to drive shaft 2420 when drive shaft 2420 rotates in the general direction of arrow "RLB" in FIG. 69 (e.g., upon a subsequent actuation of the trigger).

Driver 2430 of end effector 2400 is a generally a hollow cylinder and is configured to be positioned radially outward of at least portions of drive shaft 2420. Driver 2430 includes a body portion 2431, follower 2432 disposed adjacent a proximal end thereof, and a proximal aperture 2434. Follower 2432 of driver 2430 is a pin-like structure including first portion 2432a extending radially inward from body portion 2431, and a second portion 2432b extending radially outward from body portion 2431. First portion 2432a of follower 2432 is configured to engage first helical groove 2424 and second helical groove 2426. Second portion 2432b of follower 2432 is configured to extend at least partially through a longitudinal slot 2472 of outer tube 2470. Proximal aperture 2434 of driver 2430 is configured to allow drive shaft 2420 to pass at least partially therethrough.

Cap 2440 of end effector 2400 is configured to engage (e.g., is affixed to) a distal end of driver 2430 and is configured to engage (e.g., is affixed to) a proximal end of needle 2406. Cap 2440 includes a needle-securing portion 2442 to help engage needle 2406.

Outer tube 2470 of end effector 2400 is positioned radially outward of at least portions of barbed suture 2402, needle 2406, drive shaft 2420, driver 2430, and cap 2440. Outer tube 2470 includes longitudinal slot 2472 extending along a portion of its length. Longitudinal slot 2472 of outer tube 2470 is configured to allow second portion 2432b of follower 2432 to extend at least partially therethrough, which allows follower 2432 and driver 2430 to longitudinally translate with respect to outer tube 2470.

Figure 68:
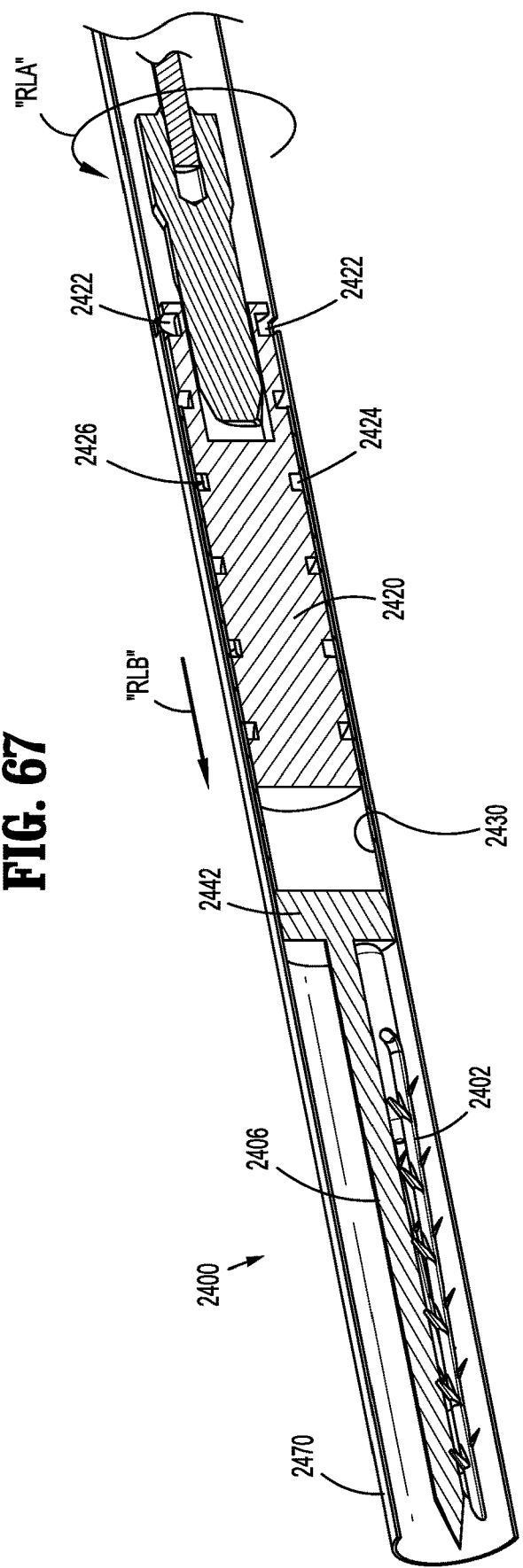
FIG. 68 is a cross-sectional view of portions of the end effector of FIGS. 65-67.

In use, in response to at least a partial actuation of the trigger of surgical device 100, drive rod 150 rotates, as discussed above. With reference to FIG. 68, rotation of the drive rod 150 results in a corresponding rotation of drive shaft 2420 in the general direction of arrow "RLA" (FIG. 68) with respect to outer tube 2470. The engagement between proximal groove 2422 of drive shaft 2420 with the at least one pin (not explicitly shown) facilitates rotation of drive shaft 2420 with respect to outer tube 2470, and restricts drive shaft 2420 from moving longitudinally with respect to outer tube 2470.

Further, the engagement between first portion 2432*a* of follower 2432 and first helical groove 2424 of drive shaft 2420 causes follower 2432 and driver 2430 to move distally in the general direction of arrow "RLB" in response to rotation of drive shaft 2420 in the general direction of arrow "RLA." The engagement between second portion 2432*b* of follower 2432 and longitudinal slot 2472 of outer tube 2470 allows follower 2432 and driver 2430 to move longitudinally with respect to outer tube 2470, and restricts follower 2432 and driver 2430 from moving rotationally with respect to outer tube 2470.

As driver 2430 translates distally, cap 2440, needle 2406 and barbed suture 2402 are pushed distally with respect to outer tube 2470. As needle 2406 travels distally, a distal portion of needle 2406 (e.g., a distal tip 2406*a*) and barbed suture 2402 distally exit outer tube 2470, and engage tissue/mesh, for instance.

When drive shaft 2420 has rotated a predetermined amount, first portion 2432*a* of follower 2432 continues its movement within first helical groove 2424, and moves into a transition groove 2425 (FIGS. 66 and 71), which interconnects first helical groove 2424 and second helical groove 2426. Continued rotation of drive shaft 2420 causes first portion 2432*a* of follower 2432 to move from transition groove 2425 and into second helical groove 2426.

Figure 69:
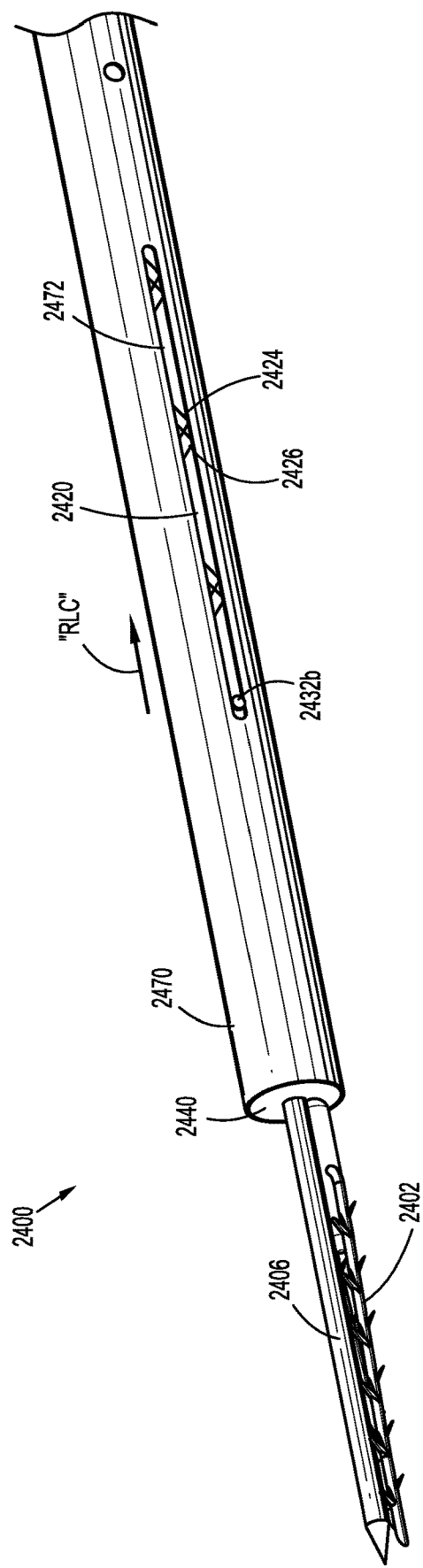
FIG. 69 is a perspective view of the end effector of FIGS. 65-68 illustrating a needle in an advanced position.

In response to continued actuation or an additional actuation of the trigger of surgical device 100, drive shaft 2420 continues to rotate in the general direction of arrow "RLA." Due to the engagement between first portion 2432*a* of follower 2432 and second helical groove 2426, the rotation of drive shaft 2420 causes follower 2432 and driver 2430 to move proximally in the general direction of arrow "RLC" (FIG. 69). Proximal movement driver 2430 results in a corresponding proximal movement of needle 2406. Needle 2406 is movable proximally until its distal tip 2406*a* is longitudinally aligned with or proximal of a distal end of outer tube 2470, thereby reducing the possibility of a user unintentionally contacting needle 2406.

It is envisioned that one complete actuation of the trigger of surgical device 100 causes drive shaft 2420 to rotate a particular number of times (e.g., five) corresponding to follower 2432 and driver 2430 moving from their proximal-most positions to their distal-most positions (corresponding to the first two and one half rotations), and back to their proximal-most positions (corresponding to the second two and one half rotations). It is also envisioned that one complete actuation of the trigger of surgical device 100 causes drive shaft 2420 to rotate a particular number of time (e.g., five) corresponding to follower 2432 and driver 2430 moving from their proximal-most positions to their distal-most positions, and that a second complete actuation of the trigger of surgical device 100 causes drive shaft 2420 to rotate a particular number of time (e.g., five) corresponding to follower 2432 and driver 2430 moving from their distal-most positions to their proximal-most positions.

While some embodiments of end effectors described herein have been described as being re-usable, it is contemplated that any of the end effectors described herein are configured for release, reloading and/or reuse.

In accordance with the present disclosure, it is contemplated that an electromechanical control module may replace handle assembly 110 to actuate the surgical device 100. The electromechanical control module may include at least one microprocessor, at least one drive motor controllable by the at least one microprocessor, and a source of power for energizing the at least one microprocessor and the at least one drive motor.

As can be appreciated, securement of any of the components of the presently disclosed devices can be effectuated using known fastening techniques such welding, crimping, gluing, etc.

Additionally, the present disclosure includes methods of using the disclosed end effectors, and methods of performing a surgical procedure utilizing the disclosed end effectors. An example of a disclosed method includes using a disclosed end effector to advance stay-sutures (e.g., four stay-sutures) through an implant (e.g., mesh) to hold the implant in a desired position, removing the end effector from the handle portion of a surgical instrument, engaging a second end effector with the same handle portion of the surgical instrument used to advance stay-sutures through the implant, and advancing tacks from the second end effector through the implant.

The present disclosure also includes surgical systems. A disclosed surgical system includes a surgical device, a first end effector and a second end effector. The surgical device includes a handle assembly and an elongated portion extending distally from the handle assembly. The first end effector is configured to releasably engage a distal portion of the elongated portion, and includes a drive assembly and a needle assembly. The drive assembly is configured to advance and retract the needle assembly upon at least a partial actuation of the handle assembly of the surgical device. The second end effector is configured to releasably engage the distal portion of the elongated portion, includes a plurality of tacks therein, and is configured to distally advance the plurality of tacks upon at least a partial actuation of the handle assembly of the surgical device.

The present disclosure also includes surgical kits including a plurality of first end effectors (e.g., pre-loaded with stay-sutures, barbed sutures, etc.), a plurality of second end effectors (e.g., pre-loaded with a plurality of tacks), and a surgical device. The surgical device includes a handle assembly and an elongated portion extending distally from the handle assembly. Each of the first end effectors and second end effectors is configured to releasably engage a distal portion of the elongated portion of the surgical device.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prepare the patient for surgery and configure the robotic surgical system with one or more of the surgical instruments disclosed herein while another surgeon (or group of surgeons) remotely controls the instrument(s) via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

What is claimed is:

1. An end effector for use with a surgical device, the end effector comprising:
   a drive assembly configured for rotation about a longitudinal axis and including a first helical groove and a second helical groove, the first helical groove encircling at least a portion of the drive assembly in a first direction, the second helical groove encircling at least a portion of the drive assembly in a second direction, the first direction is opposite from the second direction;
   an outer tube disposed radially outward of at least a portion of the drive assembly and including a longitudinal slot;
   a driver disposed in mechanical cooperation with the drive assembly, wherein rotation of the drive assembly in a first direction causes distal translation of the driver with respect to the drive assembly;
   a needle assembly disposed in mechanical cooperation with the driver, wherein distal translation of the driver causes a corresponding distal translation of the needle assembly; and
   a follower configured to engage the first helical groove of the drive assembly, wherein a portion of the follower is configured to engage the longitudinal slot of the outer tube, and wherein when the follower is engaged with the first helical groove, rotation of the drive assembly in the first direction causes distal translation of the follower with respect to the drive assembly.

2. The end effector according to claim 1, further comprising a transition groove interconnecting the first helical groove and the second helical groove.

3. The end effector according to claim 1, wherein the follower is configured to engage the second helical groove of the drive assembly.

4. The end effector according to claim 3, wherein when the follower is engaged with the second helical groove of the drive assembly, rotation of the drive assembly in the first direction causes proximal translation of the needle assembly with respect to the drive assembly.

5. The end effector according to claim 1, wherein a portion of the follower extends through an aperture of the driver.

6. The end effector according to claim 1, further comprising a suture disposed in mechanical cooperation with the needle assembly and disposed radially inward of the outer tube.

7. The end effector according to claim 1, wherein the needle assembly includes a needle, the needle being radially offset from the longitudinal axis.

8. The end effector according to claim 1, wherein the follower is pivotable about a pivot axis, the pivot axis being perpendicular to the longitudinal axis.

9. The end effector according to claim 1, further comprising a pin disposed distally of the drive assembly, the pin extending through at least one longitudinal slot of the driver.

10. The end effector according to claim 1, wherein the needle assembly includes a first needle extending distally from a needle block, and a second needle extending distally from the needle block, the first needle being parallel to the second needle.

11. An end effector for use with a surgical device, the end effector comprising:
    a drive assembly including a cylindrical body, a first helical groove encircling a portion of the cylindrical body in a first direction, and a second helical groove encircling a portion of the cylindrical body in a second direction, the first direction being opposite from the second direction;
    a driver disposed in mechanical cooperation with the drive assembly and including a longitudinal slot, wherein rotation of the drive assembly in a first direction causes distal translation of the driver relative to the drive assembly;
    a pin extending through the longitudinal slot in the driver; and
    a suture disposed in mechanical cooperation with the drive assembly.

12. The end effector according to claim 11, wherein the first helical groove includes a proximal end, wherein the second helical groove includes a proximal end, and wherein the proximal end of the first helical groove and the proximal end of the second helical groove are interconnected.

13. The end effector according to claim 11, wherein the first helical groove includes a distal end, wherein the second helical groove includes a distal end, and wherein the distal end of the first helical groove and the distal end of the second helical groove are interconnected.

14. The end effector according to claim 12, wherein the first helical groove includes a distal end, wherein the second helical groove includes a distal end, and wherein the distal end of the first helical groove and the distal end of the second helical groove are interconnected.

15. The end effector according to claim 14, wherein the first helical groove and the second helical groove share at least two points of intersection between their proximal ends and their distal ends.

16. The end effector according to claim 14, wherein the first helical groove and the second helical groove share at least four points of intersection between their proximal ends and their distal ends.

17. The end effector according to claim 13, further comprising a follower configured to move to the distal end of the first helical groove, into a transition groove, and into the distal end of the second helical groove.

18. The end effector according to claim 11, wherein the pin is disposed distally of the drive assembly.

19. An end effector for use with a surgical device, the end effector comprising:

a drive assembly configured for rotation about a longitudinal axis and including a first helical groove and a second helical groove, the first helical groove encircling at least a portion of the drive assembly in a first direction, the second helical groove encircling at least a portion of the drive assembly in a second direction, the first direction being opposite from the second direction;

a driver disposed in mechanical cooperation with the drive assembly, wherein rotation of the drive assembly in a first direction causes distal translation of the driver with respect to the drive assembly;

a pin disposed distally of the drive assembly, the pin extending through at least one longitudinal slot of the driver;

a needle assembly disposed in mechanical cooperation with the driver and including a first needle extending distally from a needle block and a second needle extending distally from the needle block, the first needle being parallel to the second needle, wherein distal translation of the driver causes a corresponding distal translation of the needle assembly; and a follower configured to engage the first helical groove of the drive assembly, wherein when the follower is engaged with the first helical groove, rotation of the drive assembly in the first direction causes distal translation of the follower with respect to the drive assembly.

* * * * *